(12) United States Patent
Fist

(10) Patent No.: US 10,760,090 B2
(45) Date of Patent: *Sep. 1, 2020

(54) PAPAVER SOMNIFERUM STRAIN WITH HIGH CONCENTRATION OF THEBAINE

(71) Applicant: Tasmanian Alkaloids Pty. Ltd., Westbury (AU)

(72) Inventor: Anthony J. Fist, Norwood (AU)

(73) Assignee: Tasmanian Alkaloids Pty. Ltd., Westbury (AU)

( * ) Notice: Subject to any disclaimer, the term of this patent is extended or adjusted under 35 U.S.C. 154(b) by 105 days.

This patent is subject to a terminal disclaimer.

(21) Appl. No.: 15/893,202

(22) Filed: Feb. 9, 2018

(65) Prior Publication Data

US 2018/0327769 A1 Nov. 15, 2018

Related U.S. Application Data

(60) Continuation of application No. 14/816,639, filed on Aug. 3, 2015, now Pat. No. 9,909,137, which is a division of application No. 12/398,245, filed on Mar. 5, 2009, now Pat. No. 9,131,649.

(60) Provisional application No. 61/034,583, filed on Mar. 7, 2008, provisional application No. 61/088,903, filed on Aug. 14, 2008, provisional application No. 61/089,163, filed on Aug. 15, 2008.

(51) Int. Cl.
| | | |
|---|---|---|
| *C12N 15/82* | (2006.01) | |
| *A01H 5/00* | (2018.01) | |
| *A01H 1/06* | (2006.01) | |
| *A01H 5/02* | (2018.01) | |
| *C07D 489/02* | (2006.01) | |
| *A01H 6/64* | (2018.01) | |

(52) U.S. Cl.
CPC ........... *C12N 15/8257* (2013.01); *A01H 1/06* (2013.01); *A01H 5/00* (2013.01); *A01H 5/02* (2013.01); *A01H 6/64* (2018.05); *C07D 489/02* (2013.01)

(58) Field of Classification Search
CPC .............................. C12N 15/8257; A01H 6/64
See application file for complete search history.

(56) References Cited

U.S. PATENT DOCUMENTS

| | | |
|---|---|---|
| 3,812,132 A | 5/1974 | Grew et al. |
| 4,277,604 A | 7/1981 | Dauben et al. |
| 4,613,668 A | 9/1986 | Rice |
| 4,795,813 A | 1/1989 | Schwartz |
| 6,067,749 A * | 5/2000 | Fist ........................ A01H 4/001 47/58.1 R |
| 6,376,221 B1 | 4/2002 | Fist et al. |
| 6,723,894 B2 | 4/2004 | Fist et al. |
| 8,067,213 B2 | 11/2011 | Fist et al. |
| 9,131,649 B2 * | 9/2015 | Fist .......................... A01H 5/02 |
| 9,909,137 B2 * | 3/2018 | Fist .......................... A01H 5/02 |

FOREIGN PATENT DOCUMENTS

| | | |
|---|---|---|
| AU | 646074 B | 3/1992 |
| AU | 2005201353 | 4/2005 |
| AU | 2003204625 | 12/2006 |
| BE | 864539 A | 4/1978 |
| DE | 112648 A1 | 4/1975 |
| EP | 164290 A1 | 5/1985 |
| EP | 1525789 | 4/2005 |
| GB | 1586626 A | 3/1981 |
| NZ | 587685 | 3/2009 |
| WO | 1998002033 | 1/1998 |
| WO | 1999011765 | 3/1999 |
| WO | 1999035902 | 7/1999 |
| WO | 2000058333 | 10/2000 |
| WO | 2005107436 | 11/2005 |
| WO | 2007022561 | 3/2007 |
| WO | 2009092134 | 7/2009 |
| WO | 2009109012 | 9/2009 |

OTHER PUBLICATIONS

Observations by Third Party submission dated Sep. 18, 2012 filed on behalf of Francopia s.a.r.l.
Supplementary European Search Report dated Feb. 17, 2011 and Search Opinion.
Official communication (Examiners Report) dated Feb. 27, 2012.
I.3: Alkaloid contents for mutated Papaver Somniferum (SFm) obtained in 1990.
II.1: Characteristics and alkaloid contents for mutated Papaver Somniferum obtained in 1993.
III.1: Geographical location of R 1 trials carried out in 1994.
III.4: General characteristics of Papaver Somniferum cultivated in 1994.
III.5: Assay of alkaloids present in Papaver Somniferum cultivated in 1995.
Jensema, E. & Archer, G., "Feasibility study on opium licensing in Afghanistan for the production of morphine and other essential medicines," General Executive Summary. The Senlis Council. 2005 pp. 130, 168-179.
Annual Press review of the GISME, Centre d'Addictologie. 2005, referring to VSD 6/1/205 (in French).
L"Humanite, Feb. 12, 1994" Un tribunal ccondamne un utilisateur de methadone (in French).

(Continued)

*Primary Examiner* — Russell Kallis

(74) *Attorney, Agent, or Firm* — Fitch, Even, Tabin & Flannery LLP

(57) ABSTRACT

The present invention is directed to an improved poppy straw, concentrate of poppy straw and opium of *Papaver somniferum* for the production of thebaine containing little or no oripavine, codeine or morphine. The present invention also provides plants, stands and seeds of *Papaver somniferum* and methods for the production of thebaine.

28 Claims, 2 Drawing Sheets

(56) References Cited

OTHER PUBLICATIONS

Brochmann-Hanssen, E., Planta Med., 50, 343-345 (1984).
Filippetti, A. et al., "Improvement of Seed Yield in Vicia Faba L. by Using Experimental Mutagenesis II Comparison of Gamma-Radiation and Ethyl-Methane-Sulphonate (EMS) in Production of Morphological Mutants", Euphytica 35 (1986) 49-59.
Henikoff, S., Till, B.J. And Comai, L. (2004) "Tilling. Traditional mutagenesis meets functional genomics". Plant Physiology 135, 630-636.
Kodym and Afza (2003), Physical and Chemical Mutagenesis, in Methods in Molecular Biology, vol. 236: Plant Functional Genomics: Methods and Protocols (Ed. E. Grotewold), Humana Press Inc, Totowa, NJ, pp. 189-203.
Koomneef, M., Dellaert, L.W.M. and van der Veen, J.H. (1982) "EMS—and radiationinduced mutation frequencies at individual loci in *Arabidopsis thaliana*(L.) Heynh". Mutat. Res. 93, 109-123.
Li, X. et al., "A fast neutron deletion mutagenesis-based reverse genetics system for plants", The Plant Journal 27(3), 235-242(2001).
Millgate et al., Nature, vol. 431, 413-414, 2004.
Palevitch, D and Levy, A 1992 Acta Horticulturae 306,33-52.
Parker, H.I., J. Am. Chem. Soc., 94, 1276-1282 (1972).
Jonsson B, and Jonsson R, Sveriges Utsadesforenings Tidskrift, "Foradling av vallmo Ipapaver somniferum" 96, 1986 p. 243 249 (poppy breeding summary p. 248).
Nyman, U. And Hall, O., "Some varieties of Papaver somniferum L. with changed morphinane alkaloid content" Hereditas (1976) 84:69-76.
Nyman, U. et al., Hereditas (1978) vol. 88; pp. 17-26.
Nyman U., Hereditas (1978) vol. 89; pp. 43-50.
Nyman, U., "Selection for high thebaine/low morphine content in Papaver somniferum L.",Hereditas (1980) vol. 93; pp. 121-124.
Extract from Wikipedia http://fr.wikipedia.org/wiki/Pavot de Californie (In French).
Extract from Wikipedia http://fr.wikipedia.org/wiki/Pavot (In French).
C.H., "Opium-free poppy under study as a codeine source", Science 190 (1975) pg. 1274.
Szymanowska, E., Liersch, J., Krzymanski, J. (Low Morphine poppy Przemko) Makniskomortinowy Prezemko. In Oilseed crops. XVlth Polish research conference, Apr. 19-20, 1994, Rosliny Oleiste, 15. (1) pp. 171-172.
Shukla, Sudhir, Khanne, K.R. and S.P. Singh, "Alkaloid Spectrum of Opium of a Cross Between Papaver Somniferum and P. Setigerum", International Journal of Pharmacognosy 1995, vol. 33, No. 3, pp. 228-231.
Nielsen, B. et al., "Oripavine—A New Alkaloid", Planta Medica, vol. 46, No. 4 (1983) pp. 205-206.
Nielsen, B. et al., "Oripavine—A New Opium Alkaloid", Dept. of Pharmaceutical Chemistry, vol. 48 (1983) pp. 205-206.
Shafiee, A. et al., "Alkaloids of Papaver Orientale L.", Journal of Pharmaceutical Sciences, vol. 66, No. 7, 1977, pp. 1050-1052.
XP-002111402 EL Kheir, Y. "The alkaloids of the stamens of Papaver somniferum" Planta Medica vol. 27, No. 3, May 1975, pp. 275-280, Figure 2; Table 2.
XP-002111403 Nash M. "Studies on the compositional changes in poppy capsule components during maturation and drying" J. Stored Prod. Res., vol. 16, No. 3-4, 1980, pp. 133-141, Table 4.
United Nations publication, Narcotic Drugs: Estimated World Requirements for 2007; Statistics for 2005 (E/ INCB/2006/2).
Nyman, U. Selection for high thebaine/low morphine content (cpv. Morph:The) in Papaver somniferum L., Hereditas 89: 43-50 (1978).
Staba, et al.; "Alkaloid Production from Papaver Tissue Cultures", Journal of Natural Products, 1982 vol. 43, pp. 256-262.
Chung, B., Effects of Plant Population Density and Rectangularity on the Growth and Yield of Poppies, Journal of Agri. Science, (1990) 115, pp. 239-245.
Wold, J. and Laane, M., Increase in Thebaine Content of Papaver Bracteatum Lindl. After Colchidcine Treatment of Seeds, Acta. Pharm. Nord. 4(1) 31-34 (1992).

Ghiorghita, G. et al., Gamma Irradiation Ethyl Methanesulfonate and Di Ethyl Sulfate Treatments Induced Changes in Morphine Content and Other Biochemical Parameters in Papaver-Somniferum, Revue Roumaine de Biologie Serie de Biologie Vegetable, vol. 27, No. 2 (1982) pp. 121-126 (XP008041209) (ISSN: 0250-5517).
Nyman, U. And Hanssen, B., Morphine Content Variation in Papaver Somniferum L. as Affected by the Presence of Some Isoquinoline Akaloids, Hereditas 88, 17-26 (1978).
UPOV: General Introduction to the Examination of Distinctness, Uniformity and Stability and the Development of Harmonized Descriptions of New Varieties of Plants, TG/1/3, Apr. 19, 2002, Chapter 2, pp. 6-7.
UPOV: Guidelines for the Conduct of Tests for Distinctness, Uniformity and Stability. Opium/Seed Poppy (*Papaver somniferum* L.), TG/166/3, 1999.
Milford, M. Norman Conquest, Alumni & Foundation News, Nov. 2002.
N. N., 2000, Agricultural R&D Quarterly Report, pp. 2-3.
N.N., 2000, Agricultural R&D Quarterly Report, p. 23, Nov. 2003.
Multilingual Dictionary of Narcotic Drugs and Psychotropic Substances under International Control. United Nations, New York 1983: p. 39.
United Nations Single Convention on Narcotic Drugs 1961: Article 1.
Manual on Mutation Breeding, Second Edition, I.A.EA, Vienna 1977, pp. 213-219.
Fist, A., and Hallam, P., Tasmanian Alkaloids, Identification of Seven New Mutant Poppy Lines, Agricultural R&D Report Apr. 2009.
Khanna and Khanna 1976, Ind J. Exp. Biol. 14,628.
Chauhan & Patra (1993) Plant Breeding 110:342-345.
Facchini, P.J. And De Luca V., "Opium Poppy and Madagascar periwinkle: model non-model systems to investigate alkaloid biosynthesis in plants," The Plant Journal, (2008) 54, pp. 763-784.
Facchini J., et al., "Opium poppy: blueprint for an alkaloid factory," Phytochem Rev (2007) 6 pp. 97-124.
M.F. Roberts, Production of alkaloids in plant cell culture. In Alkaloids, Biochemistry, Ecology, and Medicinal Applications, Edited by Roberts and Wink, Plenum Press, New York 1998, pp. 159-197.
Yoshimatsu and Shimomura (1992) "Transformation of opium poppy (*Papaver somniferum* L.) with Agrobacterium rhizogenes MAFF 03-01724", Plant Cell Reports 11, 132-136.
Facchini, et al, "Opium Poppy: a model system to investigate alkaloid biosynthesis in plants", Can J. Bot. 83: 1189-1206 (2005).
Tookey, H.L. et al., "Codeine and morphine in Papaver Somniferum grown in a controlled environment", Planta Medica, vol. 30. (1976).
Gumuscu, et al., "Evaluation of selected poppy (*Papaver Somniferum* L.) lines by their morphine and other alkaloids contents", Eur. Food Res Technol (2008) 226:1213-1220.
Leary, S., "New strain of poppy could transform industry", Burnie Advocate, Mar. 20, 2009, p. 5.
Williams, R., "Codeine poppy crop grown for first time", The Launceston Examiner, Mar. 20, 2009, p. 21.
"New Poppy Strain Revolutionizes", the Burnie Advocate, Mar. 26, 2009, p. 31.
"Poppies: no bed of roses", The Furrow, Australian + New Zealand Edition, 2006; p. 30.
Submission dated Jan. 5, 2009 by Appellant (Tasmanian Alkaloids).
Submission dated May 26, 2009 on behalf of Opponent I (in French).
Martine Dubedoubt—Rapport de DEA, 1986.
Submission dated May 26, 2009 on behalf of Opponent II.
Submission dated Apr. 12, 2012 on behalf of Opponent I (in French).
Submission dated Apr. 13, 2012 on behalf of Appellant.
Stoltenberg, Genetica, 1997, 99:89-96.
ATCC 97652 Deposit Receipt—Papaver somniferum Norman D233 seed deposit Minutes and Decision of the Technical Board of Appeal dated Jun. 20, 2012 (Appeal No: 2054/08-3.3.04).
European Search Report dated Jan. 18, 2005.
Official communication (Examiner's Report) dated Mar. 7, 2006.

(56) References Cited

OTHER PUBLICATIONS

Official communication (Examiner's Report) dated Jan. 31, 2008.
Official communication (Examiner's Report) dated Oct. 12, 2009.
Official communication (Examiner's Report) dated May 4, 2011.
Allen, R.S., et al, "Metabolic engineering of morphinan alkaloids by over-expression and RNAi suppression of salutaridinol 7-O-acetyltransferase in opium poppy" Plant Biotechnology Journal; Jan. 2008, vol. 6, pp. 22-30.
Patra, N.K. and Chavhan S.P., "Morphophysiology and genetics of induced mutants expressed in the M1 generation in opium poppies," The Journal of Heredity (1990); 81(5) pp. 347-350.
Crane, F.A. and Fairburn J.W., "Alkaloids in the germinating seedling of poppy", Transactions of the Illinois State Academy of Science. (1970) vol. 63, No. 1, 11 pp. 86-92.
Kutchan, T.M. And Dittrich H., "Characterization and mechanism of the berberine bridge enzyme, a covalently flaviuated oxidase of benzophenanthridine alkaloid biosynthesis in plants," (1995) vol. 270, No. 41 Issue Oct. 13; pp. 24475-24481.
Facchini, P.J. et al., "Molecular characterization of berberine bridge enzyme genes from opium poppy," (1996) Plant Physiol. 112: pp. 1669-1677.
De-Eknamkul W. and Zenk M.H., "Enzymatic formulation of (R)—reticuline from 1,2-dehydroreticuline in the opium poppy plant," (1990) Tetrahedron Lett 31(34), 4855-8.
De-Eknamkul W. and Zenk M.H., "Homogeneous 1,2-dehydroreticuline reductase from the opium popply plant," (1991). Microb. Util. Renewable resour. Volume Date 1990, 7:87-98.
Brochmann-Hannsen, et al., "(+)—Reticuline—A new opium alkaloid," (1965) Tetrahedron Letters No. 18, pp. 1271-1274.
Wieczorek, et al., "Radioimmunoassay determination of six opium alkaloids and its application of plant screening," 1986. Phytochemistry. vol. 25. No. 11, pp. 2639-2646.
Page, J.E., "Silencing natures narcotics: metabolic engineering of the opium poppy," Trends in Biotechnology. (2005) vol. 23, No. 7, pp. 331-333.
Ziegler J., et al., "Comparative transcript and alkaloid profiling in Papaver species identifies a short chain dehydrogenase/reductase involved in morphine biosynthesis," (2006). The Plant Journal. 48: pp. 177-192.
Brochmann-Hanssen E. and Furuya T.A. "A new opium alkaloid. Isolation and characterization of(+)-1-(3'-hydroxyl-4' methoxybenzyl)-2-methyl-6-methoxy-7-hydroxyl-1,2,3,4-tetrahydroisoquinoline [(+)-eticuline]", School of Pharmacy, University of California, Planta Med, 12(3): pp. 328-333, May 1964.
Bare, C.E, Coffman C.B. and Gentner W.A. "Growth, development and thebaine content of papaver bracteatum Lindl. In relation to spacing," (1987) Agron J. 79 pp_ 935-937.
Levy, A., "A shattering-resistant mutant of Papaver Bracteatum Lindi. Characterization and inheritance," (1985) Euphytica 34 pp. 811-815.
Nyman, U. and Bruhn, J.G., Feb. 1979 J. Med. Plant Res., vol. 35, No. 2, pp. 97-117.
Jonsson, R., Sveridges Utsadesforenings Tidskrift (1986), 96, pp. 243-249.
Ivanova, R.M. "The use of experimental mutagenesis in the breeding of the opium poppy". Sov Genet. 1972 (Translat. 1974). 8(1): 21-26.
Ghiorghita, G.I., Elvira, V., Toth, E.T., Sava, I.R. "The morphine content of third generation Papaver somniferum plants after a successive treatment with gamma rays and alkylating agents in the first and second generations". Rev. Roum. Biochim. (1993), 20(3), pp. 161-168.
Floria, F., Gillie, E. and Miriciouiu, E. "The influence of some successive mutagenic treatments on the capsules dimensions and the morphine content of Papaver somniferum L". Rev. Roum. Biochim. (1986), 23(4), pp. 285-92.
Singh, U.P. "Study of some genetic factors leading to increased opium and morphine yield in opium poppy". Adv. Biosci. (Oxford) (1989), 75 (Prof. Opioid Res.), pp. 379-82.

Chitty et al., Functional Plant Biology, 2003, 30, pp. 1045-1058 (O16).
Unterlinner et al., The Plant Journal, 1999, 18(5), pp. 465-475 (O17).
Allen et al., Nature Biotechnology, Dec. 2004, 22(12), pp. 1559-1566 (O18).
E. Brochmann-Hanssen "A second pathway for the terminal steps in the biosynthesis of morphine". Planta Medica, 1984. 50, pp. 343-345.
Lenz, R. and Zenk, M.H. Eur J. Biochem, 1995. 233, 1, 132-139 (O11).
Akhila, A. and Uniyal G.C. "Quantitative estimation of opium alkaloids". Indian J. Pharm Sci., Sep.-Oct. 1983, pp. 236-239 (O12).
Fairbairn, J.W. and Helliwell, K., "Papaver bracteatum Lindley: thebaine content in relation to plant development", I. Pharm. Pharmac., 1977, 29, pp. 65-69.
Seddigh, Majid, Jolliff, Gary D., Calhoun, Wheller, and Crane, Jimmie M., "Papaver bracteatum, Potential Commercial Source of Codeine", Economic Botany, 36, 1982, pp. 433-441.
Duke, James A., "Utilization of Papaver", Economic Botany, 27, 390-400, Oct.-Dec. 1974.
Fairburn, J.W., DSc, PhD, Sc, FPS, Dpharn., "Phytovavailability and some of its problems", The Pharmaceutical Journal, Jan. 10, 1976, pp. 29-31.
Popov, P., Dimitrov, J., Georgi EV, S. and Den Eva, T., "Radiosensitivity of Opium Poppy (*Papaver Somniferum* I.) and Morphine Content in the Dry Capsules of M1 As Influenced by CS137 Gamma Irradiation", Genetics and Plant Breeding, vol. 7, No. 4, pp. 251-257, 1974.
Sudhair, Shukla and Khasma K.R., "A Study of Gene Action for Opium Yield and Morphine Content in Papaver Somniferum l.",Indian J. Agric. Res. 29 (3), 116-120, 1995.
Pareek, S.K., Srivastava, V.K., Maheshwarj, M.L. and Gupta, R., "Performance of Advance Opium Poppy Selections for Latex, Morphine, and Seed Yields", Indian Journal of Agricultural Sciences 65 (7) pp. 498-502, Jul. 1995.
Caporale, Lynn Helena, "Chemical ecology: A View From the pharmaceutical industry", Proc. Natl. Acad. Sci. USA, vol. 92, pp., 75-82, Jan. 1995.
Villalobos, Maria Jesus Pascual; Robbelen, Gerhard and Correal Enrique, "Production and evaluation of indehiscent mutant genotypes in Euphorbia lagascae", Industrial Crops and Products 3 (1994) pp. 129-143.
Lavanua, U.C. and Snvastiava, Sangeeta, "Autotetraploid and triploid meiosis in Papaver somniferum show reduction in bound arm associations and enhanced bivalent pairing over generations", Current Research on Medicinal and Aromatic Plants, 17, (1995) pp. 10-13.
Thierfelder, A., Luhs, W., and Friedt, W., "Breeding of industrial oil crops with the aid of biotechnology: a review", Industrial Crops and Products, 1 (1993) pp. 261-271.
Ben-Salah, H., Roath, W.W., "Somaclonal variation in Cuphea viscosissima Jacq. For plant improvement", Industrial Crops and Products, 2, (1994) pp. 239-244.
Green, A.G., "Genetic control of polyunsaturated fatty acid biosynthesis in flax (*Linum usitatissimum*) seed oil", Theor Appl Genet 72, (1986) pp. 654-661.
English translation dated Sep. 4, 2001 of Jonsson B. And Jönsson R, Sveriges Utsädesförenings Tidskrift, 96, 1986, pp. 243-249.
European Patent Application No. 09718439.4, Extended European Search Report, dated Feb. 24, 2011, including the European Supplementary Search Report dated Feb. 17, 2011, and European Search Opinion for EP 09718439.4, 6 pages.
Facchini, Peter J., et al., "Differentrial and Tissue-specific Expression of a Gene Family for Tyrosine/Dopa Decarboxylase in Opium Poppy." Journal of Biological Chemistry, 1994, vol. 269, No. 43, Issue of Oct. 28, pp. 26684-26690.
Indian Application 6425/DELNP/2010, Examiner's Report, dated Mar. 29, 2017, 12 pages.
Indian Application 6425/DELNP/2010, Hearing Notice, dated Jun. 25, 2018, 3 pages.

(56) References Cited

OTHER PUBLICATIONS

Indian Application 6425/DELNP/2010, Order No. 108/2018 of the Assistant Controller of Patents & Designs in the Patent Office at Chennai, dated Dec. 20, 2018, 1 page.
International Appliction No. PCT/AU2009/000270, International Search Report, dated Apr. 14, 2009, 3 pages.
International Appliction No. PCT/AU2009/000270, Written Opinion, dated Apr. 14, 2009, 4 pages.
Li, Xin, et al., "Deleteagene: A Fast Neutron Deletion Mutagenesis-Based Gene Knockout System for Plants." Comparative and Functional Genomics, 2002, vol. 3, pp. 158-160.
Millgate, Anthony G., et al., "Morphine-Pathway Block in Top1 Poppies." Nature, vol. 431, Sep. 23, 2004, pp. 413-414, with supplementary methods (7 pages).
Prajapati, Seema, et al., "Alkaloid Profiles of the Indian Land Races of the Opium Poppy Papaver Somniferum L." Genetic Resources and Crop Evolution, 2002, 00: 1-0, 6 pages.

\* cited by examiner

PAPAVER SOMNIFERUM STRAIN WITH HIGH CONCENTRATION OF THEBAINE

CROSS-REFERENCE TO RELATED APPLICATIONS

This application is a continuation of U.S. patent application Ser. No. 14/816,639, filed Aug. 3, 2015, which is a Divisional application of U.S. patent application Ser. No. 12/398,245, filed Mar. 5, 2009 (issued on Sep. 15, 2015 as U.S. Pat. No. 9,131,649), which claims priority to U.S. Provisional Application Ser. No. 61/034,583, filed Mar. 7, 2008, 61/088,903, filed Aug. 14, 2008, and 61/089,163, filed Aug. 15, 2008, the contents of each of which are hereby incorporated by reference in their entireties.

FIELD OF THE INVENTION

The present invention is directed to the improved production of thebaine. More particularly, the present invention relates to the use of a mutagenized *Papaver somniferum* poppy plant to produce thebaine in higher yield.

BACKGROUND OF THE INVENTION

The 14-hydroxymorphinans, such as, oxycodone, naloxone, naltrexone, naltrexone methobromide, nalbuphine and nalmefene are important opiate derivatives due to their behavior as potent analgesics and/or narcotic antagonists. The most practical synthetic routes to the preparation of these pharmaceuticals have utilized the alkaloid, thebaine, as a starting material. Other important opiate derivatives such as hydrocodone and the ring-C bridged compounds buprenorphine and etorphine are also most practically prepared from thebaine.

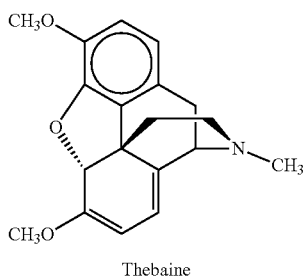
Thebaine

In accordance with one conventional process, thebaine is oxidized to 14-hydroxycodeinone by use of m-chloroperbenzoic acid in an acetic acid/trifluoroacetic acid mixture or by a mixture of hydrogen peroxide and formic acid. 14-hydroxycodeinone is catalytically reduced to oxycodone. See Scheme 1. Oxycodone is a product sold for use as an analgesic and its production consumes large amounts of thebaine.

Scheme 1

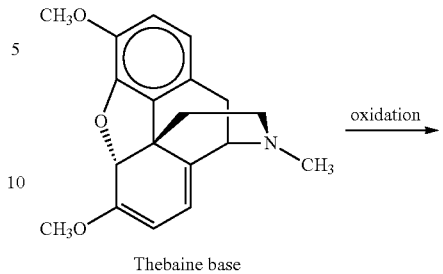
Thebaine base

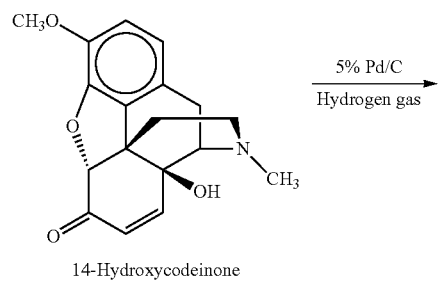
14-Hydroxycodeinone

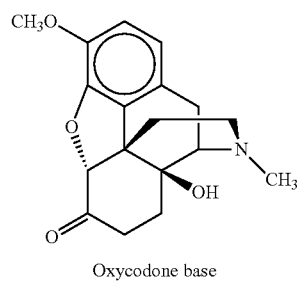
Oxycodone base

Oxycodone can be, in turn, O-demethylated with boron tribromide to yield oxymorphone. After blocking of the hydroxyl groups with a suitable blocking agent, such as, acetyl groups, the oxymorphone derivative can be reacted with cyanogen bromide in a von Braun demethylation to yield an N-cyanodihydronormorphinone derivative that is thereafter hydrolyzed to 14-hydroxydihydronormorphinone (noroxymorphone). Noroxymorphone can be readily converted to nal-compounds by N-alkylation with appropriate alkyl halide, or acylation with appropriate acyl halide or anhydride, followed by reduction. Another process, converts the oxycodone of the above process to noroxycodone by the von Braun N-demethylation followed by conversion to a 3-O-methyl-nal-compound using N-alkylation with an appropriate alkyl halide, or by alkylation with an appropriate alkyl halide, or acylation with appropriate acyl halide or anhydride, followed by reduction. The 3-O-methyl-nal-compound is converted to a nal-compound by O-demethylation.

A synthesis using thebaine to produce the ring-C bridged opiate, buprenorphine, is shown in Scheme 2.

Scheme 2
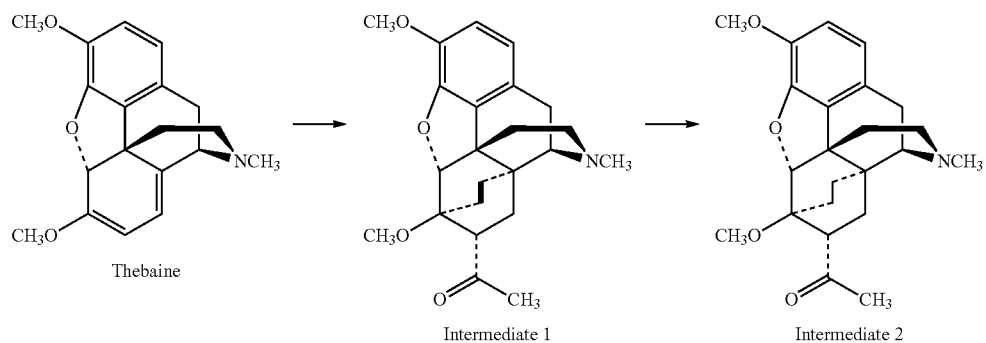
Thebaine → Intermediate 1 → Intermediate 2
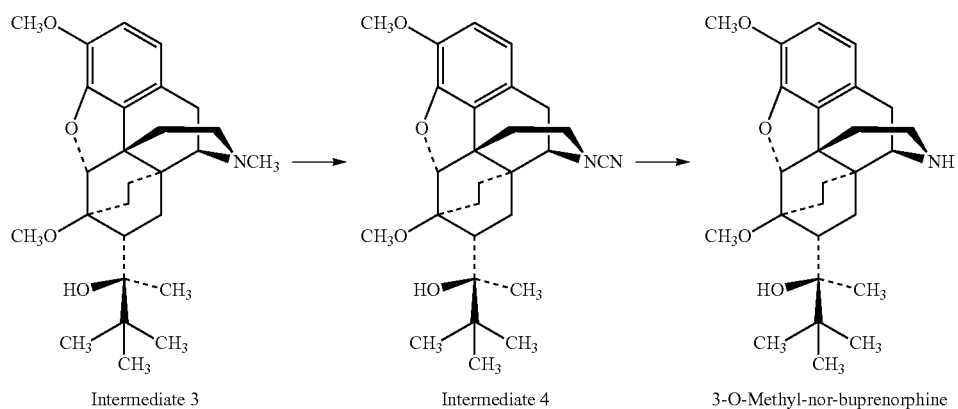
Intermediate 3 → Intermediate 4 → 3-O-Methyl-nor-buprenorphine
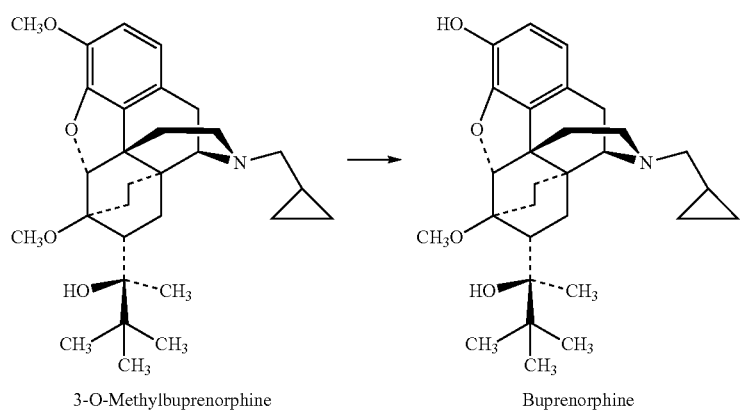
3-O-Methylbuprenorphine → Buprenorphine Another synthesis using thebaine to produce the 14-hydroxymorphinan, naltrexone as representative of the nal-compounds, is shown in Scheme 3.

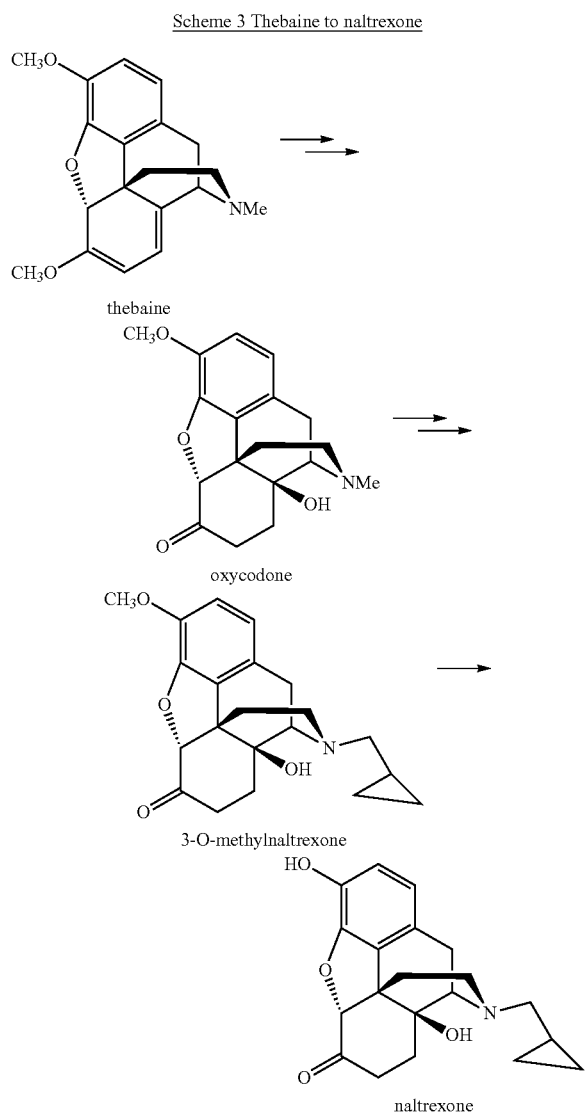

Scheme 3 Thebaine to naltrexone thebaine oxycodone

3-O-methylnaltrexone naltrexone

Another synthesis uses thebaine to produce hydrocodone as set forth in U.S. Pat. No. 3,812,132.

Although these syntheses are effective, the availability of thebaine is limited by its high cost. The high cost of thebaine contributes to the high cost of the 14-hydroxymorphinans derived from it.

One reason for the limited availability of thebaine, and its high cost, is that total synthesis is difficult. U.S. Pat. Nos. 4,613,668 and 4,795,813 discuss the scarcity of thebaine and teach the total synthesis, or alternative synthesis, of the 14-hydroxymorphinans. Yet, the demand for thebaine remains.

A second reason for the limited availability of thebaine, and its high cost, is that the primary source of thebaine is extraction from the poppy plant, *Papaver somniferum*. Morphine is the major alkaloid that accumulates in capsules of *Papaver somniferum*. Thus, the supply of thebaine is to a great degree limited to some fraction of the demand for morphine.

Alkaloids are extracted from the poppy capsules of *Papaver somniferum* by two commercial methods. In one method, the immature capsule is cut and the latex collected from the wound. The air-dried latex is opium which, according to the Merck Index, 11th edition, contains alkaloids in the amounts shown in Table I. In a second method, the mature poppy capsules and the poppy capsule stems are collected, and threshed to remove the seeds and form a straw. When necessary, the straw is dried to a water content below 16%. Solvent or water extraction is employed to remove the alkaloids from the straw. For the varieties of *Papaver somniferum* normally grown, the straw, on a dry basis, contains alkaloids in the amounts shown in Table 1.

TABLE 1

|  | opium | straw |
| --- | --- | --- |
| morphine, % | 10-16 | 1-3 |
| codeine, % | 0.8-2.5 | 0.05-0.3 |
| oripavine, % | 0-0.1 | 0-0.05 |
| thebaine, % | 0.5-2 | 0.15-0.65 |

As can be seen, the yield of thebaine and oripavine is confounded with that of other alkaloids. A poppy producing predominantly thebaine, e.g., as 90% or more of the total alkaloids, would enable a simpler extraction/purification process, resulting in higher yields, better quality and throughput and lower costs.

Where solvent or water or super critical fluid, such as $CO_2$, extraction is employed to remove the alkaloids from the straw, such method, as practiced, involves the production of "Concentrate of Poppy Straw". Concentrate of Poppy Straw (or "CPS") is described as "The material arising when poppy straw has entered into a process for the concentration of its alkaloids, when such material is made available in trade," (Multilingual dictionary of narcotic drugs and psychotropic substances under international control, United Nations, N.Y., 1983). Not inconsistent with the foregoing description, Concentrate of Poppy Straw is described as "the crude extract of poppy straw in either liquid, solid or powder form which contains the phenanthrene alkaloids of the opium poppy," 45 U. S. Federal Register 77466, Nov. 24, 1980. When in liquid form, the liquid is preferably concentrated before entering into commerce. The generally preferred Concentrate of Poppy Straw is the powder form which results from removing the solvent or water following extraction of the poppy straw. According to the United Nations publication "*Narcotic Drugs: Estimated World Requirements for* 2007; *Statistics for* 2005 (E/INCB/2006/2)", Concentrate of Poppy Straw is the dried residue obtained through the extraction of alkaloids from poppy straw. Until the second half of the 1990s, only concentrate of poppy straw containing morphine as the main alkaloid was manufactured. Since then, concentrate of poppy straw containing mainly thebaine or oripavine has started to be manufactured.

More recently, first et al., in U.S. Pat. No. 6,067,749 (the "'749 Patent"), U.S. Pat. Nos. 6,376,221 and 6,723,894, disclosed an improved poppy straw of a stably reproducing *Papaver somniferum* for the extraction of thebaine and/or oripavine (the "Norman" poppy), the threshed straw having thebaine and oripavine constituting about 50% by weight or greater of the alkaloid combination consisting of morphine, codeine, thebaine and oripavine. The Norman poppy straw constituted 1.68% thebaine, 0.74% oripavine, 0.05% codeine and no morphine as a percent by weight of the dry straw. (See, column 15, table III of the '749 Patent). While this alleviated the limited availability and high cost of thebaine to some extent, the problem of producing oripavine concurrently with thebaine contributed significantly to the cost of producing thebaine.

For many years, the perennial poppy *Papaver bracteatum* has been proposed as a source of thebaine. Thebaine is the predominant alkaloid in this species, and in selected strains it can be as high as 98% of the total alkaloids (Palevitch, D and Levy, A 1992 Acta Horticulturae 306, 33-52). Thebaine is present in the roots as well as capsules. Generally two years of growth would be required to obtain a good yield of both roots and capsules. *Papaver bracteatum* does not alleviate the problem of limited availability and high cost of thebaine because of its slow growth, low capsule yield and the problems with harvesting and processing roots.

SUMMARY OF THE INVENTION

The present invention is directed to a poppy straw comprising a poppy straw of a stably reproducing *Papaver somniferum* having thebaine constituting about 90% (preferably, about 95%, more preferably, about 97%) by weight or greater of an alkaloid combination, and having oripavine constituting about 10% (preferably, about 5%, more preferably, about 1%, most preferably, about 0.7%) by weight or less of the alkaloid combination, wherein the alkaloid combination comprises morphine, codeine, thebaine and oripavine; and wherein thebaine constitutes about 3.0% or greater of the poppy straw on a dry weight basis. In a preferred embodiment, thebaine constitutes about 3.5% or greater (preferably, about 4.0% or greater, more preferably, about 4.3% or greater) of the poppy straw on a dry weight basis. In another embodiment, oripavine constitutes about 0.4% or lower (preferably, about 0.2% or lower) of the poppy straw on a dry weight basis. In another embodiment of the invention, oripavine constitutes between 0.01 to 1.0% (preferably, between 0.02% to 0.5%) by weight of the alkaloid combination in the poppy straw.

There is also provided by the present invention a stably reproducing *Papaver somniferum* having two genetic traits controlling the thebaine-only characteristic of the plant, one trait being that described in U.S. Pat. No. 6,067,749, and the second trait regulating the step between thebaine and oripavine, resulting in substantially no oripavine. In an embodiment of the present invention is a *Papaver somniferum* plant having a high thebaine content of over 3% (preferably, over 3.5%, more preferably, over 4.0%, most preferably, over 4.3%) in the straw wherein the high thebaine content is provided by two independent traits, one trait controlling the accumulation of thebaine and oripavine compared with morphine and codeine, and the second trait controlling the accumulation of thebaine compared with oripavine. In still another embodiment of the invention is a *Papaver somniferum* plant having a high thebaine content of over 3% (preferably, over 3.5%, more preferably, over 4.0%, most preferably, over 4.3%) in the straw on a dry weight basis wherein the high thebaine content is provided by two independent genetic changes, one genetic change controlling the accumulation of thebaine and oripavine compared with morphine and codeine, and the second genetic change controlling the accumulation of thebaine compared with oripavine.

There is also provided by the present invention a method to improve the thebaine yield of a stably reproducing *Papaver somniferum* plant, the method comprising the steps of:

a) exposing at least one poppy seed of *Papaver somniferum* to a mutagenizing agent, b) growing at least one poppy seed to produce a plant bearing a leaf or an immature poppy capsule, optionally through multiple self-fertilized generations, c) sampling the leaf or poppy capsule (or any other latex-containing tissue) for the presence of thebaine, oripavine, morphine and codeine, d) repeating steps a) to c) until a poppy plant of *Papaver somniferum* is obtained having thebaine constituting about 90% (preferably, about 95%) by weight or greater, and having oripavine constituting about 10% (preferably, about 5%, more preferably, about 1%) by weight or less, of the alkaloid combination, wherein the alkaloid combination comprises morphine, codeine, thebaine and oripavine; and e) collect the seed from the plant obtained in "d" and grow another generation of plants to ensure that the subsequent generation stably re-produces the high thebaine and low oripavine characteristic. In an embodiment of this method, in step d) the poppy plant obtained has thebaine constituting about 3.0% (preferably, about 3.5%, more preferably, about 4.0%, most preferably, about 4.3%) or greater of the poppy straw, on a dry weight basis, and oripavine constituting about 0.4% (preferably, about 0.2%) or lower of the poppy straw, on a dry weight basis.

There is also provided by the present invention a stably reproducing *Papaver somniferum* plant or a stand of a stably reproducing *Papaver somniferum* plants, in which the production or activity of the enzyme responsible for the conversion of thebaine to oripavine has been substantially inhibited with the result that upon the harvesting of their poppy capsules, the poppy plants will yield a poppy straw having thebaine constituting about 90% (preferably, about 95%, more preferably, about 97%) by weight or greater of the alkaloid combination, and having oripavine constituting about 10% (preferably, about 5%, more preferably, about 1%) by weight or less of the alkaloid combination, and the poppy plants will yield a poppy straw wherein thebaine constitutes about 3.0% or greater (preferably, about 3.5% or greater, more preferably, about 4.0% or greater, most preferably, about 4.3% or greater) of the poppy straw, on a dry weight basis, and oripavine constitutes about 0.4% or lower (preferably, about 0.2% or lower) of the poppy straw, on a dry weight basis.

The present invention also provides a stably reproducing plant of *Papaver somniferum*, which upon the harvesting of their poppy capsules will yield a poppy straw having thebaine constituting about 90% (preferably, about 95%, more preferably, about 97%) by weight or greater of an alkaloid combination, and having oripavine constituting about 10% (preferably, about 5%, more preferably, about 1%, most preferably, about 0.7%) by weight or less of the alkaloid combination, wherein the alkaloid combination comprises morphine, codeine, thebaine and oripavine; and wherein thebaine constitutes about 3.0% or greater of the poppy straw on a dry weight basis. The straw of the stably reproducing *Papaver somniferum* plant of the present invention preferably contains thebaine constituting about 3.5% or greater (preferably, about 4.0% or greater, more preferably, about 4.3% or greater) of the poppy straw, on a dry weight basis, and oripavine constituting about 0.4% or lower (preferably, about 0.2% or lower) of the poppy straw, on a dry weight basis. In another embodiment of the invention, oripavine constitutes between 0.01 to 1.0% (preferably, between 0.02% to 0.5%) by weight of the alkaloid combination in the stably reproducing *Papaver somniferum* plant.

Also included in the invention is a plant comprising a stably reproducing plant of *Papaver somniferum* which upon the harvesting of its poppy capsules will yield a poppy straw having thebaine constituting at least 3% (preferably, at least 3.5%) by weight on a dry basis, and oripavine constituting no more than 0.4% by weight on a dry basis of said straw. Preferably, thebaine constitutes at least 4.0% by weight on a dry basis, and oripavine constitutes no more than 0.2% by weight on a dry basis of said straw of the plant.

The present invention also provides a plant comprising a stably reproducing plant of *Papaver somniferum* which upon the harvesting of its poppy capsules will yield a poppy straw having thebaine constituting at least about 3% (preferably, about 3.5%, more preferably, about 4%, most preferably, about 4.3%) by weight on a dry basis, and oripavine constituting about 0.05 to about 0.5% (preferably, about 0.05 to about 0.2%) by weight on a dry basis of said straw.

Also included in the invention is a seed of any of the stably reproducing poppy plants described above; preferably, the seed is a *Papaver somniferum* seed which is ATCC PTA-9109.

Also included in the invention is a concentrate of poppy straw for the extraction of thebaine comprising a concentrate of poppy straw of any of the stably reproducing poppy plants described above.

Another aspect of the invention is an opium for the extraction of thebaine comprising an opium of any of the stably reproducing poppy plants described above.

Still another aspect of the invention is a poppy straw comprising a poppy straw of any of the stably reproducing poppy plants described above.

Another embodiment of the invention is a method for the production of thebaine which comprises the steps of:
 a) harvesting poppy capsules of any of the stably reproducing poppy plants described above to produce a poppy straw; and
 b) chemically extracting the thebaine from the poppy straw.

Still another embodiment of the invention is a method for the production of thebaine which comprises the steps of:
 a) collecting and drying the latex of the immature poppy capsules of any of the stably reproducing poppy plants described above to produce opium; and
 b) chemically extracting the thebaine from the opium.

Also included in the invention is a stand of any of the stably reproducing *Papaver somniferum* plants described above.

The present invention also provides a poppy straw comprising a poppy straw of a stably reproducing *Papaver somniferum* having thebaine constituting at least about 3% (preferably, about 3.5%, more preferably, about 4%, most preferably, about 4.3%) by weight on a dry basis, and oripavine constituting about 0.05 to about 0.5% (preferably, about 0.05 to about 0.2%) by weight on a dry basis of said straw.

In the poppy straw, opium, and concentrate of poppy straw of the present invention, thebaine preferably constitutes about 96% by weight or greater of the alkaloid combination and oripavine constitutes about 0.8% by weight or less of the alkaloid combination; more preferably, thebaine constitutes about 97% by weight or greater of the alkaloid combination and oripavine constitutes about 0.7% by weight or less of the alkaloid combination. In the most preferred embodiments of the present invention, there is substantially no oripavine, morphine or codeine in the alkaloid combination. In another embodiment of the instant invention, the alkaloid combination further comprises salutaridine, reticuline, laudanine, papaverine and noscapine.

The present invention also provides *Papaver somniferum* plants, and methods for producing such plants, having poppy straw with substantially higher thebaine content, and substantially lower oripavine content, such that thebaine contents in commercially grown and harvested crops are about 3.0% or greater, preferably, about 3.5% or greater, more preferably, 4.0% or greater, most preferably, about 4.3% or greater, and oripavine contents are in the order of about 0.4%, preferably, 0.2%, or lower.

Additional embodiments of the present invention provide poppy straw, concentrate of poppy straw and opium, wherein thebaine constitutes about 95% by weight or greater of the alkaloid combination and oripavine constitutes between about 0.01 to about 1.0% by weight (preferably, between about 0.02% to 0.6% by weight, more preferably, between about 0.02% to 0.5% by weight) of the alkaloid combination.

Exemplifying the invention is a method for producing a poppy plant of *Papaver somniferum* having a stably heritable high thebaine content (that is, the high thebaine content is stably reproducing) and low oripavine content versus morphine and codeine content, the method comprising the steps of:
 a) exposing at least one poppy seed of *Papaver somniferum* to a mutagenizing agent,
 b) growing the at least one poppy seed to produce a plant bearing a leaf or an immature poppy capsule, optionally through multiple self-fertilized generations,
 c) sampling the leaf or poppy capsule for the presence of thebaine, oripavine, morphine and codeine, and
 d) repeating steps b) and c) and optionally step (a) until a poppy plant of *Papaver somniferum* is obtained which yields a poppy straw having thebaine constituting about 90% (preferably, about 95%) by weight or greater of the alkaloid combination consisting of morphine, codeine, thebaine and oripavine, and having oripavine constituting about 10% (preferably, about 5%) by weight or less of the alkaloid combination, and wherein thebaine constitutes about 3.0% (preferably, about 3.5%, more preferably, about 4.0%, most preferably, about 4.3%) or greater of the poppy straw on a dry weight basis.

Preferably, the *Papaver somniferum* seed exposed to the mutagenizing agent in step (a) of this method is a *Papaver somniferum* yielding, upon the harvesting of its poppy capsules, a poppy straw having a thebaine and oripavine content constituting 50% by weight or greater of the alkaloid combination consisting of morphine, codeine, thebaine and oripavine.

In another embodiment of this method, step (b) comprises growing the at least one poppy seed to produce a plant bearing a leaf or an immature poppy capsule, and self-pollinating to produce seed, and taking the seed thereby produced and producing an M2 generation of plants, and step (c) comprises screening the M2 plants and selecting plants which yield a poppy straw having thebaine constituting about 95% by weight or greater of the alkaloid combination consisting of morphine, codeine, thebaine and oripavine, and having oripavine constituting about 5% by weight or less of the alkaloid combination, each on a dry weight basis, and wherein thebaine constitutes about 3.5% (preferably, about 4.0%, more preferably, about 4.3%) or greater of the poppy straw on a dry weight basis, In another aspect of this method, the *Papaver somniferum* seed exposed to the mutagenizing agent in step (a) of this method is seed selected from ATCC PTA-9110 or ATCC PTA-9109.

The present invention is also directed to progeny of *Papaver somniferum* ATCC-9109, said progeny yielding a poppy straw having thebaine constituting about 90% (preferably, about 95%) by weight or greater of an alkaloid combination, and having oripavine constituting about 10% (preferably, about 5%) by weight or less of the alkaloid combination, and wherein thebaine constitutes about 3.0% (preferably, about 3.5%, more preferably, about 4.0%, most preferably, about 4.3%) or greater of the poppy straw on a dry weight basis, wherein the alkaloid combination comprises morphine, codeine, thebaine and oripavine.

Another example of the present invention is a mutant or variant of *Papaver somniferum* ATCC PTA-9109 or ATCC PTA-9110, said mutant or variant yielding a poppy straw having thebaine constituting about 90% (preferably, about 95%) by weight or greater of an alkaloid combination, and having oripavine constituting about 10% (preferably, about 5%) by weight or less of the alkaloid combination, each on a dry weight basis, and wherein thebaine constitutes about 3.0% (preferably, about 3.5%, more preferably, about 4.0%, most preferably, about 4.3%) or greater of the poppy straw on a dry weight basis, wherein the alkaloid combination comprises morphine, codeine, thebaine and oripavine.

DETAILED DESCRIPTION OF THE INVENTION

Figure 1:
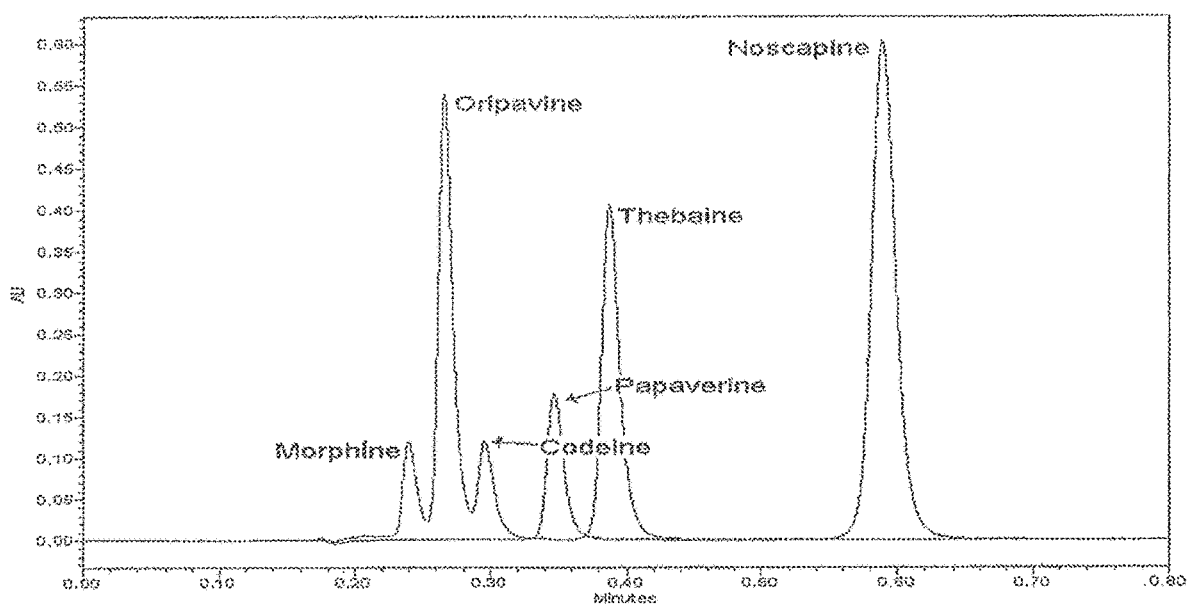
FIG. 1 provides a chromatogram showing separation of the alkaloids using the isocratic UPLC method.

Utilizing the mutagenized plants of *Papaver somniferum* as described herein, persons skilled in the art easily know how to grow them, reproduce them, collect the latex or the dried straw and purify the thebaine. As one enablement of the present invention, seeds to the mutagenized plants of *Papaver somniferum* (FN1-1242-3), as described herein, have been deposited under the Budapest Treaty with the American Type Culture Collection, 10801 University Boulevard, Manassas, Va. 20110-2209, on Mar. 20, 2008, under ATCC® Patent Deposit Designation PTA-9109. All restrictions on access to these deposits will be irrevocably removed at the time a patent issues in the United States on the basis of this application. The availability of these seeds is not to be construed as a license to practice this invention in contravention of rights granted under the authority of any government in accordance with its patent or breeder's rights laws. Regardless of the enablement provided by this deposit, persons skilled in the art of mutagenizing seed, can obtain the seed herein by employing the mutagenesis process as described below.

The production of mutagenized seed is well known in the art. Methods of seed mutagenesis as well as mutagens suitable for use in these methods, such as ethyl methanesulfonate (EMS), are described in the Manual on Mutation Breeding, 2nd ed., I.A.E.A., Vienna 1977 or in Plant Breeding, Principles and Prospects, Chapman and Hall, London 1993. For X-ray mutagenized seeds, hydrated seeds might be treated with 20,000 rads, (30 cm from the source for 45 minutes using a filter). X-ray mutagenesis is described and compared to EMS mutagenesis by Filippetti, A. et al., "Improvement of Seed Yield in *Vicia Faba* L. By Using Experimental Mutagenesis II Comparison of Gamma-Radiation and Ethyl-Methane-Sulphonate (EMS) in Production of Morphological Mutants", Euphytica 35 (1986) 49-59. DEB, diepoxybutane, mutagenized seeds might be obtained by soaking the seeds in water overnight, then soaking in 22 mM DEB for 4 hours, followed by extensive washing. Further mutagens include ethyl-2-chloroethyl sulphide, 2-chloroethyl-dimethylamine, ethylene oxide, ethyleneimine, dimethyl sulphonate, diethyl sulphonate, propane sulphone, beta-propiolactone, diazomethane, N-methyl-N-nitrosourethane, acridine orange and sodium azide.

Mutagenesis utilizing EMS is well described in the literature. The Manual on Mutation Breeding, supra, reports a preferred EMS mutagenesis process for barley seeds as practiced by K. Mikaelson. In this preferred process, the seeds are prepared, pre-soaked, treated with the mutagen and post-washed.

U.S. Pat. No. 6,067,749, incorporated by reference herein in its entirety, describes the use of EMS for the preparation of a *Papaver somniferum* strain with a high concentration of thebaine and oripavine.

Irradiation methods such as fast neutron mutagenesis may also be used to produce mutagenized seed. (See, Li, X. et al., A fast neutron deletion mutagenesis-based reverse genetics system for plants, The Plant Journal 27(3), 235-242 (2001)). Applicants employed and prefer fast neutron mutagenesis ("FNM") as the mutagen herein.

Fast neutron mutagenesis is described by Kodym and Afza (2003), Physical and Chemical Mutagenesis, pp 189-203, in Methods in Molecular Biology, vol 236: Plant Functional Genomics: Methods and Protocols (Ed. E. Grotewold), Humana Press Inc, Totowa, N.J.

Gamma ($\gamma$) Rays are electromagnetic waves of very short wavelengths and are obtained by disintegration of radioisotopes Co or Cs. $\gamma$ sources can be installed in a $\gamma$ cell, a $\gamma$ room, or $\gamma$ field. These are shielded by lead or concrete. Most $\gamma$ sources as suitable for seed irradiation, as long as the size of irradiation space is sufficient and the dose rate allows practical irradiation times.

Fast neutrons are uncharged particles of high kinetic energy and are generated in nuclear reactors or in accelerators. The scientist should assess the feasibility for seed irradiation with the operators, since not all facilities are suitably equipped and can produce fast neutrons at a low degree of contamination with other radiation.

The two radiation types differ in their physical properties and, hence, in their mutagenic activity. $\gamma$ Rays have a lower relative biological effectiveness (RBE) than fast neutrons, which implies that in order to obtain the same biological effect, a higher dose of $\gamma$ radiation must be given. RBE is mainly a function of the linear energy transfer (LET), which is the transfer of energy along the ionizing track. $\gamma$ Rays produce a few ionizations per micron of path (low LET) and belong to the category of sparsely ionizing radiation. Fast neutrons (high LET, densely ionizing radiation) impart some of their high kinetic energy via collisions, largely with protons within the material.

When radiation passes through tissue, physical events such as ionizations (ejection of electrons from molecules) and excitations (process of raising electrons to a higher energy state) occur and lead to effects in the DNA, membranes, lipids, enzymes, etc. Secondly, chemical events are induced that start with the formation of activated molecules, so-called free radicals (OH. and H.) that arise from OH− and H+. If oxygen is present, it reacts readily with radiation-induced free radicals to form peroxyradicals. In the case of low LET radiation, the formation of peroxyradicals is favoured. In high LET radiation, the formation of hydrogen peroxide ($H_2O_2$) by recombination of free radicals is favoured. All radicals and hydrogen peroxide can react with biological molecules. Primary damage caused by radiation occurs randomly and is both physiological and genetic. Physiological recovery and repair of DNA are possible to some extent, as non-damaged molecules may take over metabolic processes and DNA repair mechanisms are activated.

Before starting any mutation induction studies, it is most crucial to select suitable doses. For mutation induction, it is advisable to use two to three doses along with a control. The applicable doses will depend on the breeding or research objective, the radiation type and the particular plant material. It is known that plant genera and species and, to a lesser extent, cultivars differ in their radiosensitivity. Radiosensitivity (radiation sensitivity) is a relative measure that gives an indication of the quantity of recognizable effects of the radiation exposure on the irradiated object. The radiosensitivity is influenced by biological factors (such as genetic differences, nuclear and interphase chromosome vol) and by environmental modifying factors (oxygen, water content, post-irradiation storage, and temperature).

Modifying factors greatly affect mutagenic efficiency and reproducibility of results. Oxygen is the major modifying factor, while moisture content, temperature, and storage appear to be secondary, interacting with the oxygen effect. Oxygen shows synergistic action with sparsely ionizing radiation, but oxygen effects during irradiation and post-irradiation storage can easily be prevented by adjustment of seed water content to 12-14% in cereals and most other seeds. In oilseeds such as poppies, the seed water content should be lower, around 7-8%. The critical region is the embryo, but it can be assumed that the water content of the seed and the embryo of most species will be similar. Environmental factors are less important with densely ionizing radiation; thus, for fast neutron radiation, no seed moisture adjustment is necessary.

Unless data on the radiosensitivity of a given plant are already published or known from experience, the mutation induction program should be preceded by a radiosensitivity test. This is done by irradiating the seeds with a range of doses and by growing out the plants under greenhouse conditions. Radiosensitivity is assessed based on criteria such as reduced seedling height, fertility, and survival in the M1 generation. A seedling height reduction of 30-40% is generally assumed to give a high mutation yield. The usefulness of radiation can be judged by mutagenic efficiency, which is the production of desirable changes free from association with undesirable changes. A high dose will increase mutation frequency (the frequency at which a specific kind of mutation or mutant is found in a population of cells or individuals), but will be accompanied by negative features, such as sterility. When selecting the doses, it will be necessary to find a treatment regime providing high mutagenic efficiency.

For fast neutron radiation, dosimetric measurements have to be done during each radiation treatment, e.g., by performing the sulphur threshold detector method, since the neutron flux in the seed irradiation unit is not constant.

The Gray (symbol Gy), the SI (Systéme Internationale) unit used to quantify the absorbed dose of radiation (1 Gy=1 J/kg) replaced the old unit rad; 1 Gy=100 rads or 1 krad=10 Gy. The absorbed dose rate (Gy/s or Gy/min) indicates how much energy the irradiated material absorbs during a given unit of time. The length of exposure and the dose rate determines the radiation dose. Exposure during short times (s to a few h) at a high dose rate is referred to as acute and is most applied in irradiation programs.

We used the Atomic Energy Research Institute, Konkoly Thebe ut 29/33, X.epulet, H-1121 Budapest, Hungary to irradiate our seeds.

Fast neutrons have been shown to be a very effective mutagen. Kornneef et al. (1982) found that about 2500 lines treated with fast neutron at a does of 60 Gy are required to inactivate a gene once on average (Koornneef, M., Dellaert, L. W. M. and van der Veen, J. H. (1982) EMS- and radiation-induced mutation frequencies at individual loci in *Arabidopsis thaliana* (L.) Heynh. Mutat. Res. 93, 109-123). If the plant genome contains about 25000 genes, it is estimated that about 10 genes are randomly deleted in each line.

FNM offers a number of advantages over using chemical treatment such as EMS. Notably, the treatment is applied to the dried seed, which can be sown at a later date, while with EMS the seed needs either to be sown immediately after treatment, or carefully re-dried for sowing later.

After the seeds have been exposed to the mutagen, the seeds are grown to maturity in controlled conditions and self-pollinated. The seeds from the mature plant are taken and at least one seed is planted to grow an M2 generation. The M2 generation is screened for alkaloid production. Of course, it is possible to screen the M1 generation, but there are several advantages to screening the M2 generation. Firstly, screening the M2 generation insures that the trait resulting from mutagenesis can be inherited. Secondly, by growing the M2 generation, the basic hardiness of the plant is proven before screening. Thirdly, traits resulting from mutagenesis are generally inherited as recessive genes. Typically the mutated gene will be in the heterozygous state in the M1 generation, and thus the mutation will be masked by the dominant (non-mutated) form of the gene. In the M2 generation, however, in a proportion of the plants the gene will be in the homozygous state, and the affect of the mutation apparent. The M2 plants can be grown to produce an immature capsule, but it is possible to save time and labor if the plants are screened at an earlier stage of growth. It is recommended that the plants be screened at a point beginning at the 6 leaf stage, up to the 10 leaf stage. Screening at this early stage allows many plants to be managed in a small space. The screening process itself is the most labor intensive. Thus, to improve return on labor, only plants that appear healthy should be screened.

In the screening process, the objective is to measure each plant for morphine, codeine, thebaine and oripavine content. Additional alkaloids which can also be measured during the screening process include salutaridine, reticuline, laudanine, papaverine and noscapine. This can be accomplished by extracting, for example, a dry leaf into a liquid buffer or by dissolving a latex sample into a buffer. The buffer solutions are placed onto 96 well trays and fed mechanically through any of the high-throughput HPLCs available on the market. In a preferred embodiment, an isocratic Ultra high performance Liquid Chromatography (UPLC) method, as described herein, is utilized which provides very rapid latex screening.

Plants with interesting alkaloid contents are grown further and examined in more detail. According to the procedure herein, a second sample is taken from about 3% of plants to clarify or confirm the results of the initial screen. A more precise gradient UPLC method as described herein is used to obtain more accurate peak identification and quantification. Plants confirmed to have an unusual alkaloid profile are transplanted to 200 mm (approx 8 inch) pots for growing to maturity. Twenty one plants having high thebaine and substantially no oripavine, morphine or codeine were found after screening approximately 34,358 plants.

As used herein, the term "poppy straw" or "straw" shall mean the straw material which results when the mature poppy capsules and the poppy capsule stems of a *Papaver somniferum* plant are collected, and threshed to remove the seeds to form a straw.

The term "opium", as used herein, shall refer to the air-dried, milky exudation (i.e., the latex) from incised, unripe poppy capsules of a *Papaver somniferum* plant.

As used herein, the term "concentrate of poppy straw" or "CPS" shall mean the material arising when poppy straw has entered into a process for the concentration of its alkaloids in either liquid, solid or powder form which contains the phenanthrene alkaloids of the opium poppy.

The phrase "stand of *Papaver somniferum*" or "stand of stably reproducing *Papaver somniferum*", as used herein, refers to a group of two or more *Papaver somniferum* plants or stably reproducing *Papaver somniferum* plants located together.

As used herein, the term "alkaloid combination" shall refer to a combination of alkaloids wherein the alkaloid comprises morphine, codeine, thebaine and oripavine. In another embodiment of the present invention, the alkaloid combination further comprises salutaridine, reticuline, laudanine, papaverine and noscapine in addition to morphine, codeine, thebaine and oripavine.

A "stably reproducing" *Papaver somniferum* poppy plant as described herein refers to a poppy plant that is stably reproducing as required to plant and harvest seed poppy crop over multiple generations where each generation would be suitable, without seed selection, for commercial planting of a field crop or stand of plants exhibiting the desired alkaloid characteristics. A stably reproducing poppy plant contains the desired alkaloid characteristics as described herein, and when self pollinated, or cross pollinated by a plant with the same genes controlling alkaloid content, produces a subsequent generation of plants which substantially all have seed that when grown produces plants with the same desired alkaloid characteristics as the parent plant. Moreover, in the absence of pollination with pollen from other chemotypes (e.g., conventional morphine accumulating plants), the line will continue to produce similar plants over multiple generations, without the need for selection to maintain the desired alkaloid characteristic. An example of a desired alkaloid characteristic which can be passed on to future generations by a stably reproducing *Papaver somniferum* poppy plant includes the improved thebaine characteristics (e.g., wherein thebaine constitutes about 90% (preferably, 95%, more preferably, 96% and most preferably, 97%) by weight or greater, and oripavine constitutes about 10% (preferably, 1%, more preferably, 0.8% and most preferably, 0.7%) by weight or less of the alkaloid combination).

As used herein, the "M1 population" is the seeds and resulting plants exposed to a mutagenic agent, while "M2 population" is the progeny of self-pollinated M1 plants, "M3 population" is the progeny of self-pollinated M2 plants, "M4 population" is the progeny of self-pollinated M3 plants, and generally "Mn population" is the progeny of self-pollinated Mn-1 plants.

As stated above, there is obtained by the present invention, a poppy straw, concentrate of poppy straw or opium having thebaine constituting about 90% by weight or greater and oripavine constituting about 10% by weight or less of an alkaloid combination comprising morphine, codeine, thebaine and oripavine. Preferably, thebaine constitutes about 95% (more preferably, about 96% and most preferably, about 97%) by weight or greater, and oripavine constitutes about 1% (more preferably, about 0.8% and most preferably, about 0.7%) by weight or less of the alkaloid combination comprising morphine, codeine, thebaine and oripavine. In a preferred embodiment, the alkaloid combination further comprises salutaridine, reticuline, laudanine, papaverine and noscapine. More preferably, there is substantially no oripavine, morphine or codeine in the alkaloid combination, and most preferably, there is substantially no oripavine, morphine, codeine, salutaridine, reticuline, laudanine, papaverine or noscapine in the alkaloid combination.

As used herein, the term "substantially no" when referring to oripavine content means that oripavine constitutes less than 0.6% by weight, preferably, less than 0.5% by weight, more preferably, less than 0.4% by weight, and most preferably, between 0% and 0.2% by weight of the alkaloid combination of the poppy straw, concentrate of poppy straw or opium.

The term "substantially no", when referring to morphine, codeine, salutaridine, reticuline, laudanine, papaverine or noscapine, as used herein, means that each of the specified alkaloids constitutes less than 1% by weight, preferably, less than 0.5% by weight, more preferably, less than 0.3% by weight, and most preferably, between 0% and 0.2% by weight of the alkaloid combination of the poppy straw, concentrate of poppy straw or opium.

The term "trait", as used herein, mean a distinct heritable phenotypic characteristic. The desired traits, i.e., high thebaine content versus oripavine, morphine or codeine content, once established are highly heritable. To maintain the desired traits, care should be taken to prevent cross-pollination with normal plants unless such cross-pollination is part of a controlled breeding program.

The desired traits can be transferred into poppy lines having other characteristics (e.g. different height, early or late maturity or having disease resistance) by cross pollinating the high thebaine plant with the second parent plant, collecting F1 seed, growing a F1 plant which is allowed to self-pollinate and collect the F2 seed. The F2 seed would then be grown, and individual plants that have the high thebaine characteristic could be selected according to the methods herein, along with the other desired characteristics such as disease resistance. A skilled operator will be able to apply variations to this method as known in plant breeding.

Conducting test crosses with plants of known genotype can provide information regarding the genetic changes introduced through mutation. The characteristics of the F1 generation produced by crossing to a normal (wild type) parent will indicate whether a trait inherits as a recessive or dominant gene. Self pollinating the F1 plants and determining the phenotypes of the subsequent F2 population of plants will provide information regarding the numbers of genes responsible for particular characteristics.

The theory whereby mutagenesis has been found to be capable of raising the thebaine content of *Papaver somniferum* relative to the oripavine, morphine and codeine content is not capable of a certain or definite explanation at this time. The mutagenesis might have modified the biosynthesis pathway in any number of ways to minimize the production of oripavine. Despite the fact that definite answers are not now available, there are good reasons to believe that the correct answer is known.

*Papaver somniferum* is postulated to have two biosynthetic pathways from thebaine to morphine as shown in Scheme 4. Pathway A via neopinone, codeinone and codeine was proposed by Parker, H. I., J. Am. Chem. Soc., 94, 1276-1282 (1972). Pathway B via oripavine and morphinone was proposed by Brochmann-Hanssen, E., Planta Med., 50, 343-345 (1984). The enzyme codeinone reductase (NADPH) is believed to be active in both pathways, reducing codeinone to codeine and morphinone to morphine. Further, the TOP1 mutation (Millgate et al., Nature, Vol. 431, 413-414, 2004) affects both pathways, preventing thebaine being converted to neopinone in Pathway A, and preventing oripavine being converted to morphinone in Pathway B. The TOP1 mutation appears to block demethylation of the enol ether which converts thebaine to neopinone, as well as the demethylation of the same enol ether in oripavine.

By the methods herein, plants of *Papaver somniferum* were obtained having substantially no oripavine, morphine or codeine. Both Pathway A and Pathway B were inoperative to produce morphine in the parent line using the TOP1 mutation. The most probable step that has been affected by mutation is the phenolic O-demethylation step between thebaine and oripavine. Thus, it is believed, for the *Papaver somniferum* plants described herein, that the production or activity of the phenolic O-demethylase enzyme that converts thebaine to oripavine has been substantially inhibited. Stably reproducing *Papaver somniferum* in accordance with the present invention may also be obtained by recombinant DNA techniques. In particular, after isolation and sequencing of the gene coding for thebaine demethylase, the gene may be modified or deleted to inhibit or prevent the production of thebaine demethylase. Techniques for modifying gene activity such as RNAi, antisense and other techniques are well known to those skilled in the art. Once the gene coding is established, a TILLING technique may be used to more efficiently recover mutants from populations (Henikoff, S., Till, B. J. and Comai, L. (2004) TILLING. Traditional mutagenesis meets functional genomics. Plant Physiology 135, 630-636).

Knowing that there are genetic means of reducing the conversion of thebaine to oripavine in poppies, and that now that we have shown that these poppies are achievable and viable, even conventional breeding approaches may ultimately be used to develop such plants.

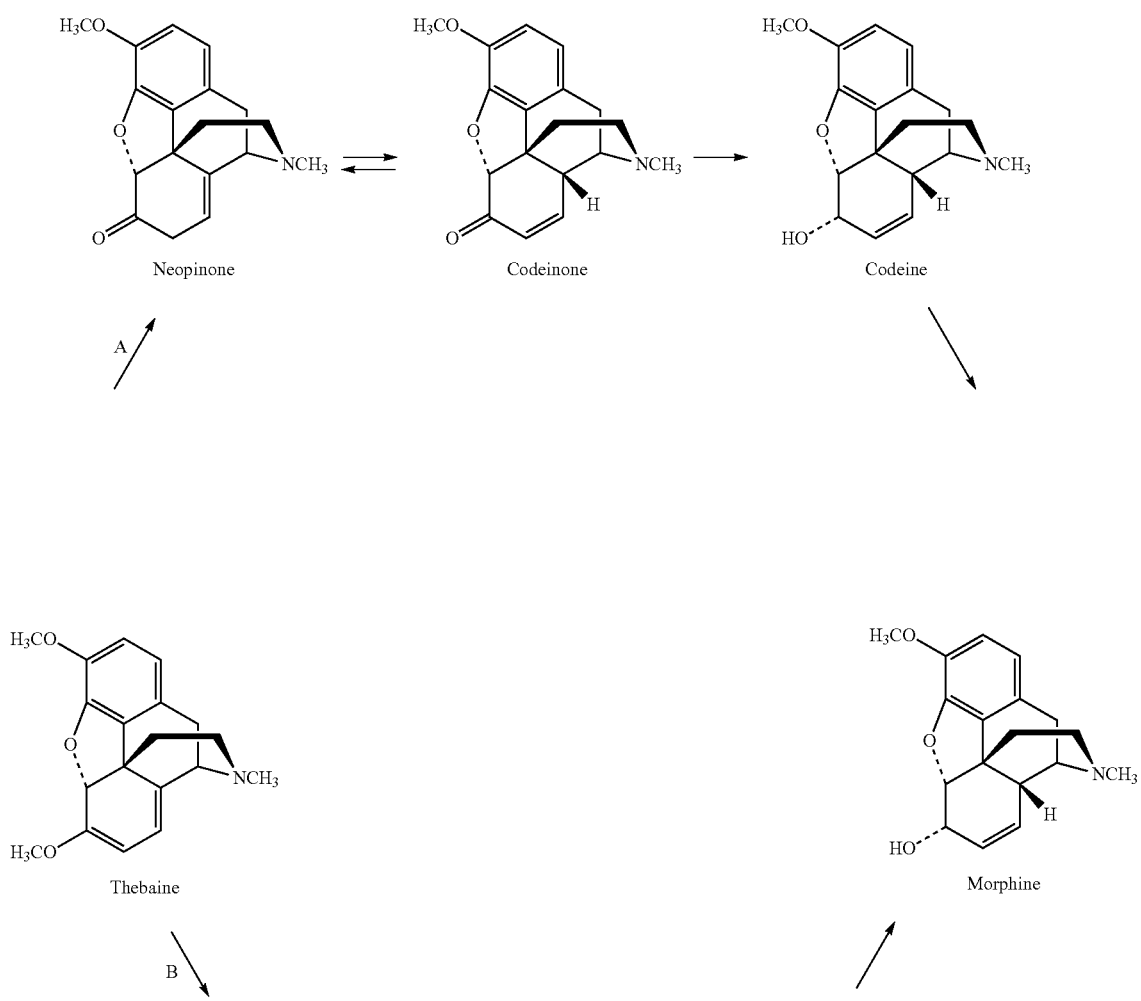

Scheme 4

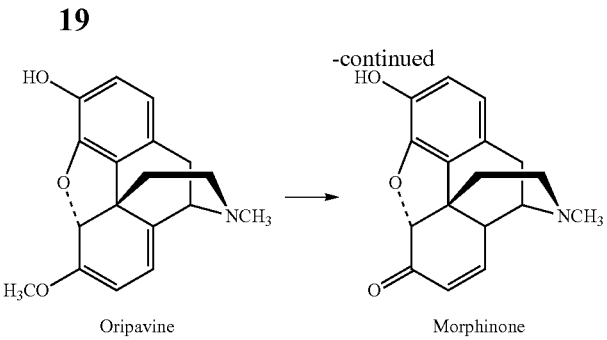

Postulated biosynthetic pathways in Papaver somniferum
A; Parker et al., 1972
B; Brochmann-Hanssen. 1984

Recovering thebaine from either the dried straw or from the opium of *Papaver somniferum* is a process well established in the art. Until now, thebaine has been extracted from this plant species either as a part of the process of extracting morphine and codeine, or more recently as part of the process of extracting thebaine and oripavine.

In one process, the straw is treated with a small amount of lime and water to soften the capsules and to form a free base of the alkaloids. Countercurrent extraction of the softened straw with methanol, ethanol or other suitable solvent forms a solvent/water extract or "miscella" containing the alkaloids, with morphine at a concentration of about 1 g/L where the straw is from standard *Papaver somniferum*. The volume of the miscella is reduced about 30× under vacuum to produce an aqueous concentrate. Thebaine is extracted from aqueous concentrate using a liquid/liquid extraction with toluene, adjusting pH for the best separation of thebaine. The thebaine is recovered from the toluene. Of course, recovering thebaine from the improved *Papaver somniferum* provided herein will be facilitated by the fact that the concentration of the thebaine in the miscella will be much higher than that of other alkaloids and thus can be more easily collected by precipitation. Also, in the substantial absence of oripavine, morphine and codeine, the thebaine might be directly extracted from the straw using toluene, xylene or other organic solvent in which thebaine has solubility.

The following Examples are set forth to aid in the understanding of the invention, and are not intended and should not be construed to limit in any way the invention set forth in the claims which follow thereafter.

Example 1

A selection of *Papaver somniferum* poppy, WF03-0802 is used as the starting material. This line contains the TOP1 mutation and therefore has the characteristics of containing thebaine and oripavine in its poppy straw and opium, and is substantially free of morphine and codeine. Seeds of WF03-0802 have been deposited under the Budapest Treaty with the American Type Culture Collection, 10801 University Boulevard, Manassas, Va. 20110-2209, on Mar. 20, 2008, under ATCC Patent Deposit Designation PTA-9110. All restrictions to the deposited seeds will be irrevocably withdrawn for the enforceable life of the patent and without restriction or condition released to the public upon the issuance of a patent. The availability of these seeds is not to be construed as a license to practice this invention in contravention of rights granted under the authority of any government in accordance with its patent or breeder's rights laws.

Six seed samples each of 10 g were prepared. One sample was retained as a control. After obtaining the necessary inspections and permits, the 5 samples were sent to the Atomic Energy Research Institute, Budapest, Hungary for irradiation. At the Institute, the samples were removed from their vials, packed into plastic bags and cadmium holders and irradiated with fast neutrons. The dose rates and exposure times were as follows:

Treatment 1 10 Gy 13 minutes 17 seconds
Treatment 2 20 Gy 26 minutes 30 seconds
Treatment 3 25 Gy 33 minutes 16 seconds
Treatment 4 35 Gy 46 minutes 27 seconds
Treatment 5 50 Gy 66 minutes 13 seconds The reported parameters of the irradiation were as follows:

Irradiation geometry at BIF of BRR at AERI: 2Y/Cd, rotated

Monitored by U-235, Th-232 fission chambers and GM counter.

The dose homogeneity within one package is better than 1%

The overall dose uncertainty is less than 5%.

Total surface gamma activity of samples after irradiation: ~695 BGND

Total surface gamma activity of samples on 20 Oct. 2005: <2 BGND (1 BGND (background) is ~90 nGy/h)

The seeds were returned to applicants by the Institute, reweighed, and found to have lost an average mass of 1.1%. This is compatible with being transferred into and out of plastic bags, as well as losing some moisture during irradiation.

Samples of the seeds were placed on damp filter paper in a Petri dish. After 3 and 7 days, the seeds were examined. Treatments 1 to 4 germinated well, while treatment 5 had very short radicles and only a small percentage of plants with shoots.

A pot trial was grown to evaluate the effect of the FNM treatment on plant growth. Two pots were sown with 10 seeds from each of treatments 1, 2, 3, 5 and control. These pots were observed for emergence and plant growth. Irradiation reduced plant emergence and survival from a mean of 9 plants per pot in the control treatment to 8.5 plants in Treatment 1, 7.5 plants in treatment 2, 7 plants in treatment 3, and 4 plants in treatment 5. Development was also delayed with increasing dose, and plant height was reduced by about 10% in treatment 1, 20% in treatment 2, and 40% in treatment 3.

The seeds from the treatments 2 and 3 were sown into 200 mm pots filled with potting mix from Forestry Commission Nursery at Perth, Tasmania. 10 seeds were sown per pot, and were covered with vermiculite. The plants were grown through to maturity in a greenhouse. All flowers were self pollinated by transferring pollen from the anthers onto the stigmatic disc. The mature capsules were harvested into large paper bags, labeled with the treatment number, keeping the different treatments separate. Where there were 2 or more capsules on one plant, these were picked into a paper bag so they stayed together. Distinctive plants were harvested into separate bags and notes made on their appearance. The harvested capsules were stored for a week or so to ensure that the seed was air dry.

The seed was separated from the capsules in the laboratory, and weighed into paper envelopes labeled with FN1-X where FN1 refers to Fast Neutron experiment 1, and X is the sequence number of the seed sample. The seed from multiple capsules from the same plant was combined into the one sample.

The seed from a total of 8,495 plants was harvested. 7,280 of these were from radiation treatment 2. The median weight of seeds harvested per M1 plant was 0.41 g.

Growth and Screening of M2 Generation
Plant Growth

M2 plants were grown in a greenhouse in trays each with 288 cells. 12 cells were sown with seed from each M1 plant. Two seeds were sown in each cell, and thinned to one plant per cell after 1-2 weeks. The plants were sown in batches of 4-17 trays each week to spread the workload over 17 weeks.

Leaf Sampling

When the plants were approximately 6 weeks old, they were analysed for alkaloid profile using the latex from the youngest fully expanded leaf (YFEL). 240 µL of latex extraction solution (23 g $NH_4H_2PO_4$ dissolved in 800 mL deionized (Dl) water, made up to 1 L with ethanol) was added to the wells of 96 well filter plates (Pall AcroPrep™ 96 Filter Plate 0.2 µm GHP membrane, natural housing, 350 µL PN S5045, (Pall Corporation, East Hills, N.Y.)). The tip of the YFEL was removed from each plant and placed in a well of the filter plate using fine forceps. Three filter plates were required to sample the plants in one tray. The plates were allowed to stand for about 30 minutes after sampling to allow the latex to bleed out of the leaves into the extraction solution. The solution was then filtered into a 96 well collection plate, which was sealed with an ABgene® Adhesive PCR foil seals (Abgene, part of ThermoFisher Scientific, Rockford, Ill.) to eliminate evaporation.

UPLC Method

The UPLC method used for the first screening stage is described in Example 2. Peak areas were exported to a Excel file (Microsoft Corporation, Seattle, Wash.) for data analysis. No correction was applied for differing UV absorption between the alkaloid peaks. The relative absorption of oripavine and thebaine, the main peaks of interest, were in any case very similar at the wavelength used.

Data Analysis

Relative peak areas were calculated for all identified alkaloids. The Excel data files were then sorted to identify plants having high thebaine content and low oripavine content relative to all identified alkaloids extracted. The chromatograms of plants identified as being of interest were reviewed to ensure that the peaks of interest were correctly integrated.

Confirmation

The plants identified in the first screening were then resampled to provide confirmation of the alkaloid profile, and to ensure that the correct plant was located prior to transplanting. The selected plants were marked with a plastic coated wire when retested so that they could be identified reliably for transplanting. A gradient UPLC system with a 2.5 minute run time (described in Example 2) was used in the confirmation testing in order to obtain more accurate peak identification and integration.

Transplanting

Plants confirmed as being of interest were transplanted into 200 mm pots, and labelled with a code, indicating the M1 seed line from which they were derived. For instance, if two selections were made from the M1 seed sample labelled FN1-1234, these selections were labelled FN1-1234-1, and FN1-1234-2. Up to 5 plants were transplanted into each pot.

Table 2, below, shows the number of plants analysed, the number of selections made, and the number of selections confirmed. Over the project, 34,358 M2 plants (from 4,176 M1 lines) were tested, and 1,049 were selected for further testing. 549 of these were confirmed and transplanted into pots. Of the 549 transplanted, 366 were selected on the basis of high thebaine and low oripavine content.

TABLE 2

| Batch | Irradiation Treatment No. | Tray numbers | Number plants analysed | Selections No. | % selns | Confirmations No. | % of plants | % of selections |
|---|---|---|---|---|---|---|---|---|
| 1 | 2 | 1-4 | 927 | 51 | 5.5 | 23 | 2.5 | 45 |
| 2 | 2 | 5-8 | 856 | 15 | 1.8 | 12 | 1.4 | 80 |
| 3 | 2 | 9-12 | 914 | 29 | 3.2 | 23 | 2.5 | 79 |
| 4 | 2 | 13-16 | 976 | 37 | 3.8 | 27 | 2.8 | 73 |
| 5 | 2 | 17-20 | 924 | 40 | 4.3 | 14 | 1.5 | 35 |
| 6 | 2 | 21-28 | 1900 | 47 | 2.5 | 21 | 1.1 | 45 |
| 7 | 2 | 29-35 | 1670 | 27 | 1.6 | 16 | 1.0 | 59 |
| 8 | 2 | 36-43 | 1746 | 85 | 4.9 | 30 | 1.7 | 35 |
| 9 | 2 | 44-52 | 2134 | 39 | 1.8 | 39 | 1.8 | 100 |
| 10 | 2 | 53-60 | 1890 | 31 | 1.6 | 31 | 1.6 | 100 |
| 11 | 2 | 61-77 | 3524 | 104 | 3.0 | 51 | 1.4 | 49 |
| 12 | 2 | 78-91 | 2737 | 86 | 3.1 | 29 | 1.1 | 34 |
| 13 | 2 | 92-111 | 4591 | 119 | 2.6 | 58 | 1.3 | 49 |
| 14 | 3 | 297-313 | 2808 | 109 | 3.9 | 74 | 2.6 | 68 |
| 15 | 2 | 129-145 | 2108 | 117 | 5.6 | 44 | 2.1 | 38 |

TABLE 2-continued

| Irradiation | | | Number plants | Selections | | Confirmations | | % of |
|---|---|---|---|---|---|---|---|---|
| Batch | Treatment No. | Tray numbers | analysed | No. | % selns | No. | % of plants | selections |
| 16 | 2 | 146-162 | 2467 | 56 | 2.3 | 34 | 1.4 | 61 |
| 17 | 2 | 163-174 | 2186 | 57 | 2.6 | 23 | 1.1 | 40 |
| Totals: | | | 34358 | 1049 | 3.1 | 549 | 1.60 | 52.3 |

Table 3, below, lists the 366 selections made on the basis of high thebaine and low oripavine content in latex from leaf samples. The alkaloid profile is based on peak area, not alkaloid concentration.

TABLE 3

| | M1 | | | Alkaloid profile (percentage of area under peaks) | | | | | | | | | |
|---|---|---|---|---|---|---|---|---|---|---|---|---|---|
| Seln No. | Seed Line | Tray | Plate/ Position | Mor- phine | Oripavine | Saluta- ridine | Codeine | Reticuline | Lauda- nine | Papa- verine | Thebaine | Nos- capine | Selection Name |
| 29 | 105 | 7 | P20 B10 | 2 | 1.7 | 1 | 0 | 0 | 1 | 0 | 94 | 0 | FN1-105-2 |
| 41 | 165 | 9 | P27 B8 | 0 | 4.9 | 1 | 0 | 1 | 2 | 0 | 90 | 1 | FN1-165-1 |
| 42 | 165 | 9 | P27 B9 | 0 | 4.4 | 2 | 0 | 2 | 2 | 0 | 90 | 0 | FN1-165-2 |
| 46 | 183 | 10 | P29 C6 | 0 | 6.5 | 1 | 0 | 1 | 1 | 0 | 91 | 0 | FN1-183-1 |
| 54 | 223 | 12 | P34 B1 | 0 | 5.7 | 2 | 0 | 0 | 2 | 0 | 91 | 0 | FN1-223-1 |
| 64 | 269 | 13 | P39 D9 | 0 | 3.7 | 1 | 0 | 1 | 1 | 0 | 92 | 0 | FN1-269-1 |
| 65 | 270 | 13 | P39 E3 | 0 | 4.5 | 2 | 0 | 1 | 1 | 0 | 90 | 0 | FN1-270-1 |
| 66 | 272 | 13 | P39 G8 | 0 | 2.3 | 1 | 0 | 2 | 1 | 0 | 92 | 0 | FN1-272-1 |
| 68 | 291 | 14 | P42 B12 | 0 | 2.2 | 2 | 0 | 1 | 1 | 0 | 93 | 0 | FN1-291-1 |
| 72 | 300 | 15 | P43 C10 | 0 | 6.3 | 1 | 0 | 1 | 1 | 0 | 90 | 1 | FN1-300-2 |
| 74 | 317 | 15 | P45 D2 | 0 | 2.4 | 1 | 0 | 0 | 0 | 0 | 96 | 0 | FN1-317-1 |
| 77 | 329 | 16 | P46 H2 | 0 | 4.9 | 1 | 0 | 1 | 1 | 0 | 92 | 0 | FN1-329-1 |
| 78 | 333 | 16 | P47 D10 | 0 | 5.4 | 1 | 0 | 1 | 0 | 0 | 93 | 0 | FN1-333-1 |
| 79 | 340 | 16 | P48 C1 | 0 | 5.8 | 0 | 0 | 1 | 1 | 0 | 91 | 1 | FN1-340-1 |
| 80 | 340 | 16 | P48 C2 | 0 | 6.1 | 0 | 0 | 1 | 1 | 0 | 91 | 1 | FN1-340-2 |
| 83 | 340 | 16 | P48 C10 | 1 | 6.4 | 1 | 0 | 1 | 1 | 0 | 90 | 0 | FN1-340-5 |
| 84 | 345 | 16 | P48 H1 | 0 | 2.6 | 1 | 0 | 2 | 1 | 0 | 92 | 1 | FN1-345-1 |
| 85 | 345 | 16 | P48 H5 | 0 | 4.9 | 1 | 0 | 2 | 1 | 0 | 91 | 1 | FN1-345-2 |
| 94 | 399 | 19 | P55 F9 | 0 | 1.5 | 0 | 0 | 1 | 2 | 0 | 92 | 1 | FN1-399-3 |
| 95 | 399 | 19 | P55 F11 | 0 | 2.1 | 0 | 0 | 1 | 0 | 3 | 90 | 0 | FN1-399-4 |
| 96 | 404 | 19 | P56 C5 | 0 | 1.5 | 0 | 0 | 1 | 1 | 0 | 93 | 0 | FN1-404-1 |
| 100 | 461 | 21 | P63 D6 | 0 | 3.6 | 1 | 0 | 1 | 1 | 1 | 92 | 0 | FN1-461-1 |
| 103 | 486 | 22 | P66 D1 | 0 | 3.5 | 1 | 0 | 2 | 2 | 0 | 91 | 1 | FN1-486-1 |
| 106 | 557 | 25 | P75 C1 | 0 | 1.1 | 0 | 0 | 0 | 0 | 0 | 98 | 0 | FN1-557-1 |
| 107 | 593 | 27 | P79 G5 | 0 | 3.9 | 0 | 0 | 1 | 1 | 0 | 94 | 1 | FN1-593-1 |
| 110 | 601 | 27 | P80 G6 | 0 | 0.4 | 0 | 0 | 1 | 0 | 0 | 97 | 1 | FN1-601-1 |
| 111 | 607 | 27 | P81 E12 | 0 | 3.5 | 0 | 0 | 1 | 0 | 0 | 95 | 0 | FN1-607-1 |
| 114 | 622 | 28 | P83 D9 | 0 | 4.3 | 0 | 0 | 1 | 1 | 0 | 93 | 1 | FN1-622-1 |
| 115 | 625 | 28 | P83 G12 | 0 | 3.6 | 0 | 0 | 1 | 1 | 0 | 94 | 0 | FN1-625-1 |
| 117 | 630 | 28 | P84 D11 | 0 | 4.4 | 0 | 0 | 0 | 0 | 0 | 96 | 0 | FN1-630-1 |
| 119 | 633 | 28 | P84 G9 | 0 | 4.3 | 0 | 0 | 2 | 1 | 0 | 92 | 1 | FN1-633-1 |
| 120 | 503 | 23 | P68 E8 | 0 | 3.3 | 1 | 0 | 1 | 0 | 0 | 94 | 0 | FN1-503-1 |
| 122 | 640 | 29 | P85 F8 | 0 | 4.0 | 0 | 0 | 1 | 1 | 0 | 93 | 1 | FN1-640-1 |
| 123 | 658 | 29 | P87 H4 | 0 | 5.8 | 0 | 0 | 2 | 1 | 0 | 90 | 1 | FN1-658-1 |
| 124 | 674 | 30 | P89 H7 | 0 | 2.8 | 0 | 0 | 1 | 1 | 0 | 95 | 1 | FN1-674-1 |
| 125 | 675 | 30 | P90 A10 | 0 | 1.5 | 0 | 0 | 1 | 2 | 0 | 94 | 1 | FN1-675-1 |
| 127 | 736 | 33 | P97 F8 | 0 | 3.9 | 0 | 0 | 1 | 1 | 0 | 93 | 1 | FN1-736-1 |
| 128 | 743 | 33 | P98 E8 | 0 | 4.2 | 0 | 0 | 3 | 1 | 0 | 91 | 1 | FN1-743-1 |
| 129 | 748 | 33 | P99 B7 | 0 | 4.8 | 0 | 0 | 2 | 1 | 0 | 91 | 1 | FN1-748-1 |
| 130 | 754 | 33 | P99 H8 | 0 | 5.6 | 0 | 0 | 2 | 1 | 0 | 91 | 1 | FN1-754-1 |
| 131 | 754 | 33 | P99 H12 | 0 | 4.1 | 0 | 0 | 1 | 1 | 0 | 93 | 1 | FN1-754-2 |
| 132 | 775 | 34 | P102 E8 | 0 | 3.9 | 0 | 0 | 2 | 1 | 0 | 93 | 0 | FN1-775-1 |
| 134 | 695 | 31 | P92 E4 | 0 | 9.0 | 0 | 0 | 0 | 0 | 0 | 90 | 1 | FN1-695-2 |
| 139 | 809 | 36 | P106 G1 | 0 | 1.7 | 0 | 0 | 0 | 8 | 0 | 91 | 0 | FN1-809-1 |
| 140 | 809 | 36 | P106 G2 | 0 | 0.0 | 0 | 0 | 0 | 0 | 4 | 96 | 0 | FN1-809-2 |
| 143 | 841 | 37 | P110 G10 | 4 | 2.1 | 0 | 0 | 0 | 0 | 0 | 94 | 0 | FN1-841-1 |
| 144 | 846 | 37 | P111 D1 | 1 | 2.0 | 0 | 0 | 1 | 1 | 0 | 95 | 0 | FN1-846-1 |
| 145 | 846 | 37 | P111 D2 | 0 | 0.0 | 0 | 0 | 0 | 0 | 0 | 100 | 0 | FN1-846-2 |
| 146 | 846 | 37 | P111 D12 | 0 | 1.1 | 0 | 0 | 2 | 0 | 0 | 97 | 0 | FN1-846-3 |
| 147 | 874 | 38 | P114 H5 | 0 | 1.6 | 0 | 0 | 0 | 0 | 0 | 98 | 0 | FN1-874-1 |
| 148 | 874 | 38 | P114 H6 | 0 | 3.2 | 0 | 0 | 0 | 0 | 0 | 97 | 0 | FN1-874-2 |
| 149 | 875 | 39 | P115 A5 | 0 | 0.0 | 0 | 0 | 0 | 0 | 0 | 100 | 0 | FN1-875-1 |
| 150 | 884 | 39 | P116 B9 | 3 | 2.0 | 0 | 0 | 0 | 0 | 0 | 95 | 0 | FN1-884-1 |
| 153 | 900 | 40 | P118 B1 | 0 | 0.0 | 0 | 0 | 0 | 0 | 0 | 98 | 1 | FN1-900-1 |

TABLE 3-continued

| | M1 | | | Alkaloid profile (percentage of area under peaks) | | | | | | | | |
|---|---|---|---|---|---|---|---|---|---|---|---|---|
| Seln No. | Seed Line | Tray | Plate/ Position | Mor- phine | Oripavine | Saluta- ridine | Codeine | Reticuline | Lauda- nine | Papa- verine | Thebaine | Nos- capine | Selection Name |
| 154 | 900 | 40 | P118 B3 | 0 | 0.5 | 0 | 0 | 0 | 1 | 0 | 97 | 1 | FN1-900-2 |
| 155 | 900 | 40 | P118 B6 | 0 | 0.3 | 0 | 0 | 0 | 0 | 0 | 97 | 1 | FN1-900-3 |
| 156 | 900 | 40 | P118 B8 | 0 | 0.0 | 0 | 0 | 0 | 0 | 0 | 98 | 1 | FN1-900-4 |
| 157 | 900 | 40 | P118 B12 | 0 | 0.0 | 0 | 0 | 1 | 1 | 0 | 98 | 0 | FN1-900-5 |
| 158 | 902 | 40 | P118 D3 | 0 | 1.6 | 0 | 0 | 0 | 0 | 0 | 97 | 0 | FN1-902-1 |
| 159 | 912 | 40 | P119 F4 | 0 | 1.8 | 0 | 0 | 1 | 0 | 1 | 92 | 1 | FN1-912-1 |
| 160 | 915 | 40 | P120 A6 | 0 | 1.9 | 0 | 0 | 0 | 1 | 0 | 93 | 2 | FN1-915-1 |
| 161 | 916 | 40 | P120 B12 | 0 | 1.2 | 0 | 0 | 0 | 1 | 0 | 98 | 0 | FN1-916-1 |
| 162 | 945 | 41 | P123 G8 | 0 | 2.5 | 0 | 0 | 0 | 0 | 0 | 94 | 1 | FN1-945-1 |
| 163 | 945 | 41 | P123 G11 | 0 | 1.6 | 0 | 0 | 0 | 0 | 0 | 96 | 0 | FN1-945-2 |
| 167 | 998 | 44 | P130 D6 | 0 | 0.8 | 0 | 0 | 0 | 0 | 0 | 99 | 0 | FN1-998-1 |
| 168 | 998 | 44 | P130 D8 | 0 | 2.1 | 0 | 0 | 0 | 0 | 0 | 97 | 0 | FN1-998-2 |
| 172 | 1027 | 45 | P134 A4 | 0 | 0.9 | 0 | 0 | 0 | 0 | 0 | 98 | 0 | FN1-1027-1 |
| 173 | 1027 | 45 | P134 A10 | 0 | 1.4 | 0 | 0 | 0 | 0 | 0 | 98 | 0 | FN1-1027-2 |
| 174 | 1050 | 46 | P136 H5 | 0 | 1.6 | 0 | 0 | 0 | 0 | 0 | 98 | 0 | FN1-1050-1 |
| 175 | 1050 | 46 | P136 H11 | 0 | 2.5 | 0 | 0 | 0 | 1 | 0 | 96 | 0 | FN1-1050-2 |
| 176 | 1085 | 47 | P141 C5 | 0 | 2.7 | 0 | 0 | 0 | 0 | 0 | 96 | 0 | FN1-1085-1 |
| 178 | 1108 | 48 | P144 B, 3 | 0 | 0.0 | 3 | 0 | 0 | 0 | 0 | 97 | 0 | FN1-1108-1 |
| 179 | 1116 | 49 | P145 B, 9 | 0 | 3.6 | 0 | 0 | 0 | 0 | 0 | 94 | 1 | FN1-1116-1 |
| 180 | 1123 | 49 | P146 A, 11 | 0 | 3.6 | 0 | 0 | 0 | 0 | 0 | 95 | 0 | FN1-1123-1 |
| 181 | 1133 | 49 | P147 C, 9 | 0 | 1.3 | 0 | 0 | 0 | 1 | 0 | 93 | 2 | FN1-1133-1 |
| 183 | 1139 | 50 | P148 A, 5 | 0 | 2.9 | 0 | 0 | 0 | 0 | 1 | 95 | 1 | FN1-1139-1 |
| 184 | 1139 | 50 | P148 A, 8 | 0 | 3.8 | 0 | 1 | 0 | 0 | 2 | 92 | 0 | FN1-1139-2 |
| 185 | 1141 | 50 | P148 C, 6 | 0 | 0.0 | 1 | 1 | 0 | 0 | 0 | 95 | 1 | FN1-1141-1 |
| 187 | 1149 | 50 | P149 C, 3 | 0 | 1.3 | 0 | 0 | 0 | 0 | 0 | 97 | 2 | FN1-1149-1 |
| 188 | 1153 | 50 | P149 G, 4 | 0 | 0.4 | 0 | 0 | 0 | 0 | 1 | 97 | 0 | FN1-1153-1 |
| 192 | 1170 | 51 | P151 H, 2 | 0 | 3.6 | 0 | 0 | 0 | 0 | 0 | 94 | 1 | FN1-1170-1 |
| 194 | 1176 | 51 | P152 F, 12 | 0 | 3.9 | 0 | 0 | 0 | 0 | 0 | 93 | 1 | FN1-1176-1 |
| 195 | 1180 | 51 | P153 B, 7 | 0 | 0.7 | 0 | 2 | 0 | 1 | 0 | 92 | 2 | FN1-1180-1 |
| 196 | 1180 | 51 | P153 B, 10 | 0 | 2.5 | 0 | 0 | 0 | 0 | 0 | 97 | 0 | FN1-1180-2 |
| 197 | 1183 | 51 | P153 E, 9 | 0 | 0.9 | 0 | 0 | 0 | 0 | 2 | 95 | 1 | FN1-1183-1 |
| 198 | 1183 | 51 | P153 E, 11 | 0 | 0.8 | 0 | 0 | 0 | 0 | 0 | 94 | 3 | FN1-1183-2 |
| 199 | 1185 | 51 | P153 G, 8 | 0 | 0.4 | 0 | 1 | 0 | 0 | 0 | 98 | 0 | FN1-1185-1 |
| 200 | 1186 | 51 | P153 H, 9 | 0 | 2.2 | 0 | 0 | 0 | 0 | 0 | 95 | 1 | FN1-1186-1 |
| 203 | 1201 | 52 | P155 G, 3 | 0 | 3.5 | 0 | 0 | 1 | 0 | 0 | 93 | 1 | FN1-1201-1 |
| 204 | 1204 | 52 | P156 B, 1 | 0 | 3.0 | 0 | 0 | 0 | 0 | 0 | 95 | 1 | FN1-1204-1 |
| 205 | 1211 | 52 | P156 G, 2 | 0 | 2.5 | 0 | 0 | 0 | 0 | 0 | 95 | 0 | FN1-1211-1 |
| 208 | 1242 | 54 | P160 E1 | 0 | 0.0 | 0 | 0 | 0 | 0 | 0 | 100 | 0 | FN1-1242-1 |
| 209 | 1242 | 54 | P160 E8 | 0 | 0.0 | 0 | 0 | 0 | 0 | 0 | 100 | 0 | FN1-1242-2 |
| 210 | 1242 | 54 | P160 E9 | 0 | 0.0 | 0 | 0 | 0 | 0 | 0 | 100 | 0 | FN1-1242-3 |
| 213 | 1270 | 55 | P164 A11 | 0 | 0.0 | 0 | 0 | 0 | 0 | 0 | 100 | 0 | FN1-1270-1 |
| 214 | 1272 | 55 | P164 C6 | 0 | 0.0 | 0 | 0 | 0 | 0 | 0 | 100 | 0 | FN1-1272-1 |
| 216 | 1303 | 56 | P168 B, 2 | 0 | 4.3 | 0 | 0 | 1 | 1 | 0 | 92 | 1 | FN1-1303-1 |
| 217 | 1313 | 57 | P169 D, 8 | 0 | 5.2 | 0 | 0 | 0 | 0 | 1 | 94 | 0 | FN1-1313-1 |
| 218 | 1326 | 57 | P171 A, 5 | 0 | 3.9 | 0 | 0 | 0 | 0 | 0 | 93 | 1 | FN1-1326-1 |
| 219 | 1326 | 57 | P171 A, 11 | 0 | 2.5 | 0 | 1 | 0 | 0 | 1 | 94 | 1 | FN1-1326-2 |
| 220 | 1331 | 57 | P171 F, 7 | 0 | 2.3 | 0 | 0 | 0 | 0 | 0 | 96 | 1 | FN1-1331-1 |
| 224 | 1366 | 59 | P176 3:A, 11 | 0 | 1.9 | 0 | 0 | 0 | 0 | 0 | 98 | 0 | FN1-1366-1 |
| 225 | 1370 | 59 | P176 3:E, 6 | 0 | 2.2 | 0 | 0 | 0 | 0 | 0 | 97 | 0 | FN1-1370-1 |
| 226 | 1373 | 59 | P176 3:H, 11 | 0 | 0.5 | 0 | 0 | 0 | 0 | 0 | 99 | 0 | FN1-1373-1 |
| 227 | 1376 | 59 | P177 4:C, 4 | 0 | 0.0 | 0 | 0 | 0 | 0 | 0 | 98 | 0 | FN1-1376-1 |
| 229 | 1381 | 59 | P177 4:H, 11 | 0 | 2.2 | 0 | 0 | 0 | 0 | 0 | 97 | 1 | FN1-1381-1 |
| 230 | 1387 | 60 | P178 5:F, 1 | 0 | 1.2 | 0 | 0 | 0 | 0 | 0 | 97 | 0 | FN1-1387-1 |
| 232 | 1401 | 60 | P180 7:D, 11 | 0 | 0.0 | 0 | 0 | 0 | 0 | 0 | 95 | 1 | FN1-1401-1 |
| 233 | 1402 | 60 | P180 7:E, 12 | 0 | 0.0 | 0 | 0 | 0 | 0 | 0 | 96 | 3 | FN1-1402-1 |
| 234 | 1403 | 60 | P180 7:F, 1 | 0 | 1.2 | 0 | 0 | 0 | 0 | 0 | 95 | 1 | FN1-14034 |
| 235 | 1405 | 60 | P180 7:H, 5 | 0 | 0.0 | 0 | 0 | 0 | 0 | 0 | 96 | 2 | FN1-1405-1 |
| 236 | 1405 | 60 | P180 7:H, 6 | 0 | 0.0 | 0 | 0 | 0 | 0 | 1 | 97 | 0 | FN1-1405-2 |
| 237 | 1413 | 61 | P181 H4 | 0 | 0.0 | 0 | 0 | 0 | 0 | 0 | 100 | 0 | FN1-1413-1 |
| 238 | 1419 | 61 | P182 F2 | 0 | 0.0 | 0 | 0 | 0 | 0 | 0 | 100 | 0 | FN1-1419-1 |
| 239 | 1432 | 62 | P184 C3 | 0 | 0.0 | 0 | 0 | 0 | 0 | 0 | 100 | 0 | FN1-1432-1 |
| 240 | 1444 | 62 | P185 G1 | 0 | 0.0 | 0 | 0 | 0 | 0 | 0 | 100 | 0 | FN1-1444-1 |
| 241 | 1447 | 62 | P186 B3 | 0 | 0.0 | 0 | 0 | 0 | 0 | 0 | 100 | 0 | FN1-1447-1 |
| 242 | 1474 | 63 | P189 E7 | 0 | 0.0 | 0 | 0 | 0 | 0 | 0 | 100 | 0 | FN1-1474-1 |
| 245 | 1519 | 65 | P195 B6 | 0 | 0.0 | 0 | 0 | 0 | 0 | 0 | 100 | 0 | FN1-1519-1 |
| 246 | 1519 | 65 | P195 B7 | 0 | 0.0 | 0 | 0 | 0 | 0 | 0 | 100 | 0 | FN1-1519-2 |
| 248 | 1533 | 66 | P196 H12 | 0 | 0.0 | 0 | 0 | 0 | 0 | 0 | 100 | 0 | FN1-1533-1 |
| 249 | 1534 | 66 | P197 A5 | 0 | 0.0 | 0 | 0 | 0 | 0 | 0 | 100 | 0 | FN1-1534-1 |
| 250 | 1534 | 66 | P197 A6 | 0 | 0.0 | 0 | 0 | 0 | 0 | 0 | 100 | 0 | FN1-1534-2 |
| 251 | 1535 | 66 | P197 B11 | 0 | 0.0 | 0 | 0 | 0 | 0 | 0 | 100 | 0 | FN1-1535-1 |
| 252 | 1536 | 66 | P197 C7 | 0 | 1.7 | 0 | 0 | 0 | 0 | 0 | 98 | 0 | FN1-1536-1 |
| 254 | 1567 | 67 | P201 B7 | 0 | 0.0 | 0 | 0 | 0 | 0 | 0 | 100 | 0 | FN1-1567-1 |
| 255 | 1571 | 67 | P201 F10 | 0 | 0.0 | 0 | 0 | 0 | 0 | 0 | 100 | 0 | FN1-1571-1 |
| 256 | 1571 | 67 | P201 F11 | 0 | 0.0 | 0 | 0 | 0 | 0 | 0 | 100 | 0 | FN1-1571-2 |
| 257 | 1571 | 67 | P201 F12 | 0 | 0.0 | 0 | 0 | 0 | 2 | 0 | 98 | 0 | FN1-1571-3 |

TABLE 3-continued

| | M1 | | | Alkaloid profile (percentage of area under peaks) | | | | | | | | | |
|---|---|---|---|---|---|---|---|---|---|---|---|---|---|
| Seln No. | Seed Line | Tray | Plate/ Position | Mor- phine | Oripavine | Saluta- ridine | Codeine | Reticuline | Lauda- nine | Papa- verine | Thebaine | Nos- capine | Selection Name |
| 258 | 1571 | 67 | P201 F2 | 0 | 0.0 | 0 | 0 | 0 | 0 | 0 | 100 | 0 | FN1-1571-4 |
| 259 | 1571 | 67 | P201 F3 | 0 | 0.0 | 0 | 0 | 0 | 0 | 0 | 100 | 0 | FN1-1571-5 |
| 260 | 1571 | 67 | P201 F4 | 0 | 0.0 | 0 | 0 | 0 | 0 | 0 | 100 | 0 | FN1-1571-6 |
| 261 | 1571 | 67 | P201 F5 | 0 | 0.0 | 0 | 0 | 0 | 0 | 0 | 100 | 0 | FN1-1571-7 |
| 262 | 1571 | 67 | P201 F7 | 0 | 0.0 | 0 | 0 | 0 | 0 | 0 | 100 | 0 | FN1-1571-8 |
| 263 | 1571 | 67 | P201 F8 | 0 | 0.0 | 0 | 0 | 0 | 0 | 0 | 100 | 0 | FN1-1571-9 |
| 264 | 1571 | 67 | P201 F9 | 0 | 0.0 | 0 | 0 | 0 | 0 | 0 | 100 | 0 | FN1-1571-10 |
| 265 | 1573 | 67 | P201 H12 | 0 | 0.0 | 0 | 0 | 0 | 0 | 0 | 100 | 0 | FN1-1573-1 |
| 268 | 1600 | 69 | P205 C11 | 0 | 0.0 | 0 | 0 | 0 | 0 | 0 | 100 | 0 | FN1-1600-1 |
| 269 | 1621 | 69 | P207 H4 | 0 | 0.0 | 0 | 0 | 0 | 0 | 0 | 100 | 0 | FN1-1621-1 |
| 270 | 1625 | 70 | P208 D2 | 0 | 1.9 | 2 | 0 | 1 | 2 | 0 | 94 | 0 | FN1-1625-1 |
| 271 | 1659 | 71 | P212 F8 | 0 | 1.4 | 0 | 0 | 2 | 0 | 0 | 97 | 0 | FN1-1659-1 |
| 272 | 1660 | 71 | P212 G8 | 0 | 1.9 | 0 | 0 | 1 | 0 | 0 | 97 | 0 | FN1-1660-1 |
| 273 | 1662 | 71 | P213 A11 | 0 | 1.8 | 1 | 0 | 1 | 0 | 0 | 96 | 0 | FN1-1662-1 |
| 274 | 1662 | 71 | P213 A12 | 0 | 1.5 | 0 | 0 | 1 | 0 | 0 | 97 | 0 | FN1-1662-2 |
| 275 | 1701 | 73 | P217 H2 | 0 | 1.0 | 0 | 0 | 0 | 0 | 0 | 99 | 0 | FN1-1701-1 |
| 276 | 1702 | 73 | P218 A11 | 0 | 2.0 | 0 | 0 | 0 | 0 | 0 | 97 | 1 | FN1-1702-1 |
| 277 | 1703 | 73 | P218 B2 | 0 | 1.3 | 0 | 0 | 0 | 0 | 0 | 99 | 0 | FN1-1703-1 |
| 279 | 1719 | 74 | P220 B1 | 0 | 0.0 | 0 | 0 | 0 | 0 | 0 | 100 | 0 | FN1-1719-1 |
| 280 | 1741 | 74 | P222 H8 | 0 | 1.5 | 0 | 0 | 0 | 0 | 0 | 98 | 0 | FN1-1741-1 |
| 281 | 1741 | 74 | P222 H12 | 0 | 0.0 | 0 | 0 | 0 | 0 | 0 | 100 | 0 | FN1-1741-2 |
| 282 | 1744 | 75 | P223 C9 | 0 | 0.0 | 0 | 0 | 0 | 0 | 0 | 100 | 0 | FN1-1744-1 |
| 283 | 1763 | 75 | P225 F8 | 0 | 0.0 | 0 | 0 | 0 | 0 | 0 | 100 | 0 | FN1-1763-1 |
| 284 | 1771 | 76 | P226 F2 | 0 | 0.8 | 1 | 0 | 0 | 0 | 0 | 98 | 0 | FN1-1771-1 |
| 285 | 1771 | 76 | P226 F3 | 0 | 0.0 | 0 | 0 | 0 | 0 | 0 | 100 | 0 | FN1-1771-2 |
| 287 | 1813 | 77 | P231 H11 | 0 | 1.8 | 1 | 0 | 1 | 0 | 0 | 94 | 0 | FN1-1813-1 |
| 290 | 1835 | 78 | P234 C9 | 0 | 1.9 | 0 | 0 | 3 | 3 | 0 | 92 | 0 | FN1-1835-2 |
| 291 | 1835 | 78 | P234 C11 | 0 | 1.8 | 0 | 0 | 4 | 2 | 0 | 92 | 0 | FN1-1835-3 |
| 292 | 1841 | 79 | P235 D8 | 0 | 0.0 | 0 | 0 | 0 | 0 | 0 | 100 | 0 | FN1-1841-1 |
| 295 | 1869 | 80 | P238 H5 | 0 | 0.9 | 0 | 0 | 0 | 0 | 0 | 99 | 0 | FN1-1869-1 |
| 296 | 1869 | 80 | P238 H8 | 0 | 1.4 | 0 | 0 | 0 | 0 | 0 | 98 | 0 | FN1-1869-2 |
| 298 | 1898 | 81 | P242 E5 | 0 | 1.3 | 0 | 0 | 1 | 1 | 0 | 97 | 0 | FN1-1898-1 |
| 299 | 1913 | 82 | P244 D4 | 0 | 0.0 | 0 | 0 | 0 | 0 | 0 | 100 | 0 | FN1-1913-1 |
| 301 | 1944 | 83 | P248 C1 | 0 | 1.6 | 0 | 0 | 1 | 0 | 0 | 97 | 0 | FN1-1944-1 |
| 304 | 2017 | 86 | P257 C12 | 0 | 1.0 | 1 | 0 | 0 | 0 | 0 | 98 | 0 | FN1-2017-1 |
| 307 | 2085 | 89 | P265 G1 | 0 | 2.3 | 0 | 0 | 0 | 0 | 0 | 96 | 0 | FN1-2085-1 |
| 308 | 2085 | 89 | P265 G2 | 0 | 1.4 | 0 | 0 | 0 | 0 | 0 | 99 | 0 | FN1-2085-2 |
| 309 | 2103 | 89 | P267 H2 | 0 | 1.2 | 0 | 0 | 0 | 0 | 0 | 99 | 0 | FN1-2103-1 |
| 310 | 2114 | 90 | P269 C2 | 0 | 0.8 | 1 | 0 | 1 | 0 | 0 | 97 | 0 | FN1-2114-1 |
| 311 | 2115 | 90 | P269 D5 | 0 | 1.0 | 0 | 0 | 0 | 0 | 0 | 99 | 0 | FN1-2115-1 |
| 312 | 2152 | 91 | P273 H3 | 0 | 0.8 | 0 | 0 | 0 | 0 | 0 | 99 | 0 | FN1-2152-1 |
| 313 | 2152 | 91 | P273 H7 | 0 | 0.0 | 0 | 0 | 0 | 0 | 0 | 100 | 0 | FN1-2152-2 |
| 314 | 2152 | 91 | P273 H9 | 0 | 0.8 | 0 | 0 | 0 | 0 | 0 | 99 | 0 | FN1-2152-3 |
| 315 | 2152 | 91 | P273 H11 | 0 | 0.0 | 0 | 0 | 0 | 0 | 0 | 100 | 0 | FN1-2152-4 |
| 317 | 2154 | 92 | P274 B4 | 0 | 4.1 | 0 | 0 | 0 | 0 | 4 | 92 | 0 | FN1-2154-1 |
| 318 | 2172 | 92 | P276 D7 | 0 | 0.0 | 0 | 0 | 0 | 0 | 0 | 100 | 0 | FN1-2172-1 |
| 319 | 2175 | 92 | P276 G8 | 0 | 0.0 | 0 | 0 | 0 | 0 | 0 | 100 | 0 | FN1-2175-1 |
| 321 | 2186 | 93 | P278 B6 | 0 | 2.0 | 0 | 0 | 0 | 0 | 0 | 98 | 0 | FN1-2186-1 |
| 322 | 2186 | 93 | P278 B11 | 0 | 0.0 | 0 | 0 | 0 | 0 | 0 | 98 | 0 | FN1-2186-2 |
| 324 | 2196 | 93 | P279 D5 | 0 | 1.3 | 1 | 0 | 1 | 3 | 0 | 94 | 0 | FN1-2196-1 |
| 325 | 2199 | 93 | P279 G3 | 0 | 0.0 | 0 | 0 | 0 | 0 | 0 | 100 | 0 | FN1-2199-1 |
| 326 | 2199 | 93 | P279 G10 | 0 | 0.0 | 0 | 0 | 0 | 0 | 0 | 100 | 0 | FN1-2199-2 |
| 327 | 2200 | 93 | P279 H1 | 0 | 0.0 | 0 | 0 | 0 | 0 | 0 | 97 | 0 | FN1-2200-1 |
| 330 | 2215 | 94 | P281 G2 | 0 | 0.0 | 0 | 0 | 0 | 0 | 3 | 91 | 0 | FN1-2215-1 |
| 331 | 2215 | 94 | P281 G6 | 0 | 0.0 | 0 | 0 | 0 | 0 | 0 | 97 | 0 | FN1-2215-2 |
| 332 | 2219 | 94 | P282 B2 | 0 | 0.0 | 0 | 0 | 0 | 0 | 0 | 100 | 0 | FN1-2219-1 |
| 333 | 2219 | 94 | P282 B6 | 0 | 0.0 | 0 | 0 | 0 | 0 | 0 | 100 | 0 | FN1-2219-2 |
| 335 | 2221 | 94 | P282 D8 | 0 | 0.0 | 4 | 0 | 0 | 0 | 4 | 93 | 0 | FN1-2221-1 |
| 336 | 2224 | 94 | P282 G4 | 0 | 0.0 | 0 | 0 | 0 | 0 | 0 | 100 | 0 | FN1-2224-1 |
| 337 | 2231 | 95 | P283 F5 | 0 | 0.0 | 0 | 0 | 0 | 0 | 0 | 100 | 0 | FN1-2231-1 |
| 338 | 2231 | 95 | P283 F12 | 0 | 0.0 | 0 | 0 | 0 | 0 | 0 | 100 | 0 | FN1-2231-2 |
| 339 | 2233 | 95 | P283 H7 | 0 | 3.0 | 0 | 0 | 0 | 0 | 0 | 97 | 0 | FN1-2233-1 |
| 340 | 2241 | 95 | P284 H1 | 0 | 0.0 | 0 | 0 | 0 | 0 | 0 | 100 | 0 | FN1-2241-1 |
| 341 | 2241 | 95 | P284 H4 | 0 | 2.7 | 0 | 0 | 0 | 0 | 0 | 97 | 0 | FN1-2241-2 |
| 342 | 2243 | 95 | P285 B9 | 0 | 0.0 | 0 | 0 | 0 | 0 | 0 | 96 | 0 | FN1-2243-1 |
| 343 | 2245 | 95 | P285 C5 | 0 | 0.0 | 0 | 0 | 0 | 0 | 0 | 98 | 0 | FN1-2245-1 |
| 344 | 2245 | 95 | P285 C10 | 0 | 0.0 | 0 | 0 | 0 | 0 | 0 | 100 | 0 | FN1-2245-2 |
| 345 | 2255 | 96 | P286 E9 | 0 | 0.0 | 0 | 0 | 0 | 0 | 0 | 100 | 0 | FN1-2255-1 |
| 346 | 2267 | 96 | P288 A10 | 1 | 0.0 | 1 | 0 | 0 | 0 | 0 | 99 | 0 | FN1-2267-1 |
| 349 | 2280 | 97 | P289 F11 | 0 | 0.0 | 0 | 0 | 0 | 5 | 0 | 91 | 4 | FN1-2280-1 |
| 354 | 2288 | 97 | P290 F9 | 0 | 0.9 | 0 | 0 | 1 | 1 | 0 | 96 | 1 | FN1-2288-1 |
| 355 | 2325 | 99 | P295 C5 | 0 | 0.0 | 0 | 0 | 0 | 0 | 0 | 100 | 0 | FN1-2325-1 |
| 356 | 2329 | 99 | P295 G4 | 0 | 0.0 | 0 | 0 | 2 | 2 | 0 | 97 | 0 | FN1-2329-1 |
| 357 | 2365 | 100 | P300 C9 | 0 | 0.0 | 0 | 0 | 0 | 2 | 0 | 98 | 0 | FN1-2365-1 |
| 358 | 2372 | 101 | P301 B1 | 0 | 0.0 | 0 | 0 | 0 | 0 | 0 | 100 | 0 | FN1-2372-1 |

TABLE 3-continued

| | M1 | | | Alkaloid profile (percentage of area under peaks) | | | | | | | | |
|---|---|---|---|---|---|---|---|---|---|---|---|---|
| Seln No. | Seed Line | Tray | Plate/ Position | Mor- phine | Oripavine | Saluta- ridine | Codeine | Reticuline | Lauda- nine | Papa- verine | Thebaine | Nos- capine | Selection Name |
| 361 | 2412 | 102 | P306 B2  | 0 | 0.7 | 0 | 0 | 0 | 0 | 0 | 99  | 0 | FN1-2412-1 |
| 362 | 2425 | 103 | P307 G8  | 0 | 0.0 | 0 | 0 | 0 | 0 | 0 | 100 | 0 | FN1-2425-1 |
| 363 | 2427 | 103 | P308 A6  | 0 | 0.0 | 0 | 0 | 0 | 0 | 0 | 100 | 0 | FN1-2427-1 |
| 364 | 2437 | 103 | P309 C12 | 0 | 0.0 | 0 | 0 | 0 | 0 | 0 | 100 | 0 | FN1-2437-1 |
| 365 | 2443 | 104 | P310 A1  | 0 | 0.7 | 0 | 0 | 1 | 0 | 0 | 97  | 0 | FN1-2443-1 |
| 367 | 2492 | 106 | P316 A5  | 0 | 0.0 | 0 | 0 | 0 | 1 | 0 | 99  | 0 | FN1-2492-1 |
| 374 | 2604 | 110 | P330 A6  | 0 | 0.0 | 0 | 0 | 0 | 1 | 0 | 99  | 0 | FN1-2604-1 |
| 376 | 7299 | 298 | P892 C2  | 0 | 0.0 | 0 | 0 | 0 | 3 | 0 | 97  | 0 | FN1-7299-2 |
| 377 | 7299 | 298 | P892 C3  | 0 | 0.0 | 0 | 0 | 0 | 2 | 0 | 98  | 0 | FN1-7299-3 |
| 378 | 7299 | 298 | P892 C4  | 0 | 0.5 | 0 | 0 | 0 | 1 | 0 | 98  | 0 | FN1-7299-4 |
| 379 | 7299 | 298 | P892 C10 | 0 | 0.7 | 0 | 0 | 0 | 2 | 0 | 98  | 0 | FN1-7299-5 |
| 380 | 7299 | 298 | P892 C12 | 0 | 0.0 | 0 | 0 | 0 | 3 | 0 | 97  | 0 | FN1-7299-6 |
| 381 | 7303 | 298 | P892 G10 | 0 | 0.0 | 0 | 0 | 0 | 0 | 0 | 100 | 0 | FN1-7303-1 |
| 382 | 7304 | 298 | P892 H2  | 0 | 0.0 | 0 | 0 | 0 | 0 | 0 | 100 | 0 | FN1-7304-1 |
| 383 | 7304 | 298 | P892 H5  | 0 | 0.0 | 0 | 0 | 1 | 1 | 0 | 98  | 0 | FN1-7304-2 |
| 384 | 7306 | 296 | P893 B6  | 0 | 0.0 | 0 | 0 | 0 | 1 | 0 | 98  | 1 | FN1-7306-1 |
| 385 | 7325 | 299 | P895 E10 | 0 | 0.0 | 1 | 0 | 1 | 2 | 0 | 97  | 0 | FN1-7325-1 |
| 386 | 7329 | 299 | P896 A8  | 0 | 0.0 | 0 | 0 | 0 | 0 | 0 | 100 | 0 | FN1-7329-1 |
| 387 | 7329 | 299 | P896 A10 | 0 | 0.0 | 0 | 0 | 0 | 1 | 0 | 99  | 0 | FN1-7329-2 |
| 388 | 7332 | 299 | P896 D3  | 0 | 0.0 | 0 | 0 | 0 | 1 | 0 | 99  | 0 | FN1-7332-1 |
| 389 | 7341 | 299 | P897 E3  | 0 | 0.0 | 0 | 0 | 0 | 0 | 0 | 100 | 0 | FN1-7341-1 |
| 390 | 7342 | 299 | P897 F1  | 0 | 0.0 | 0 | 1 | 0 | 2 | 0 | 97  | 0 | FN1-7342-1 |
| 391 | 7342 | 299 | P897 F9  | 0 | 0.0 | 0 | 1 | 0 | 2 | 0 | 96  | 1 | FN1-7342-2 |
| 393 | 7348 | 300 | P898 D5  | 0 | 1.1 | 0 | 0 | 0 | 0 | 0 | 99  | 0 | FN1-7348-1 |
| 394 | 7353 | 300 | P898 H1  | 0 | 0.6 | 0 | 0 | 0 | 0 | 0 | 99  | 0 | FN1-7353-1 |
| 395 | 7354 | 300 | P899 A3  | 0 | 0.0 | 0 | 0 | 0 | 1 | 0 | 99  | 0 | FN1-7354-1 |
| 396 | 7354 | 300 | P899 A8  | 0 | 0.0 | 0 | 0 | 0 | 1 | 0 | 99  | 0 | FN1-7354-2 |
| 397 | 7355 | 300 | P899 B2  | 0 | 0.0 | 0 | 0 | 0 | 0 | 0 | 100 | 0 | FN1-7355-1 |
| 398 | 7355 | 300 | P899 B5  | 0 | 0.0 | 0 | 0 | 0 | 1 | 0 | 99  | 0 | FN1-7355-2 |
| 399 | 7373 | 301 | P901 C10 | 0 | 1.0 | 0 | 0 | 0 | 0 | 0 | 99  | 0 | FN1-7373-1 |
| 400 | 7378 | 301 | P901 H1  | 0 | 0.0 | 0 | 0 | 1 | 0 | 0 | 99  | 0 | FN1-7378-1 |
| 401 | 7380 | 301 | P902 B9  | 0 | 0.0 | 0 | 0 | 0 | 0 | 0 | 100 | 0 | FN1-7380-1 |
| 402 | 7386 | 301 | P902 H6  | 0 | 0.0 | 0 | 0 | 1 | 1 | 0 | 98  | 0 | FN1-7386-1 |
| 403 | 7386 | 301 | P902 H9  | 0 | 0.0 | 0 | 0 | 0 | 0 | 0 | 100 | 0 | FN1-7386-2 |
| 404 | 7397 | 302 | P904 B1  | 0 | 0.0 | 0 | 0 | 0 | 0 | 0 | 100 | 0 | FN1-7397-1 |
| 405 | 7399 | 302 | P904 D3  | 0 | 0.0 | 0 | 0 | 0 | 3 | 0 | 97  | 0 | FN1-7399-1 |
| 406 | 7400 | 302 | P904 E12 | 0 | 0.0 | 0 | 0 | 0 | 0 | 0 | 100 | 0 | FN1-7400-1 |
| 407 | 7445 | 303 | P909 H12 | 0 | 0.9 | 0 | 0 | 0 | 1 | 0 | 98  | 0 | FN1-7445-1 |
| 408 | 7447 | 304 | P910 B9  | 0 | 0.7 | 0 | 0 | 0 | 0 | 0 | 98  | 0 | FN1-7447-1 |
| 409 | 7448 | 304 | P910 C6  | 0 | 0.0 | 0 | 0 | 0 | 0 | 0 | 98  | 2 | FN1-7448-1 |
| 410 | 7452 | 304 | P910 G1  | 0 | 0.0 | 0 | 0 | 1 | 1 | 0 | 98  | 0 | FN1-7452-1 |
| 411 | 7462 | 304 | P911 H6  | 0 | 0.9 | 0 | 0 | 0 | 0 | 1 | 99  | 0 | FN1-7462-1 |
| 412 | 7467 | 304 | P912 C1  | 0 | 0.6 | 0 | 0 | 0 | 1 | 0 | 97  | 0 | FN1-7467-1 |
| 413 | 7467 | 304 | P912 C2  | 0 | 0.4 | 1 | 0 | 0 | 2 | 0 | 97  | 0 | FN1-7467-2 |
| 414 | 7471 | 304 | P912 G7  | 0 | 1.0 | 0 | 0 | 0 | 0 | 0 | 98  | 1 | FN1-7471-1 |
| 415 | 7472 | 304 | P912 H2  | 0 | 0.0 | 0 | 0 | 0 | 0 | 0 | 95  | 5 | FN1-7472-1 |
| 416 | 7491 | 305 | P914 G8  | 0 | 0.8 | 0 | 0 | 0 | 0 | 0 | 99  | 0 | FN1-7491-1 |
| 417 | 7499 | 305 | P915 F2  | 0 | 1.2 | 0 | 0 | 0 | 0 | 0 | 99  | 0 | FN1-7499-1 |
| 418 | 7506 | 306 | P916 B6  | 0 | 1.1 | 0 | 0 | 1 | 0 | 1 | 97  | 0 | FN1-7506-1 |
| 419 | 7509 | 306 | P916 D1  | 0 | 0.0 | 0 | 0 | 0 | 0 | 0 | 100 | 0 | FN1-7509-1 |
| 420 | 7513 | 306 | P916 H5  | 0 | 1.0 | 0 | 0 | 1 | 1 | 0 | 96  | 1 | FN1-7513-1 |
| 421 | 7525 | 306 | P918 C10 | 0 | 1.3 | 0 | 0 | 1 | 1 | 0 | 95  | 1 | FN1-7525-1 |
| 422 | 7529 | 306 | P918 G11 | 0 | 0.0 | 0 | 0 | 0 | 0 | 0 | 100 | 0 | FN1-7529-1 |
| 423 | 7535 | 307 | P919 E8  | 0 | 0.0 | 0 | 0 | 0 | 0 | 0 | 97  | 3 | FN1-7535-1 |
| 424 | 7536 | 307 | P919 F1  | 0 | 1.2 | 0 | 0 | 2 | 1 | 0 | 96  | 0 | FN1-7536-1 |
| 426 | 7551 | 307 | P921 C5  | 0 | 0.0 | 0 | 0 | 0 | 0 | 0 | 100 | 0 | FN1-7551-1 |
| 427 | 7557 | 308 | P922 A12 | 0 | 0.0 | 0 | 0 | 0 | 0 | 0 | 100 | 0 | FN1-7557-1 |
| 428 | 7558 | 308 | P922 B7  | 0 | 0.0 | 0 | 0 | 0 | 0 | 0 | 100 | 0 | FN1-7558-1 |
| 429 | 7560 | 308 | P922 D8  | 0 | 1.2 | 0 | 0 | 0 | 1 | 0 | 98  | 0 | FN1-7560-1 |
| 430 | 7566 | 308 | P923 B9  | 0 | 0.0 | 0 | 0 | 0 | 0 | 2 | 98  | 0 | FN1-7566-1 |
| 431 | 7579 | 308 | P924 F3  | 0 | 0.8 | 0 | 0 | 3 | 0 | 2 | 92  | 2 | FN1-7579-1 |
| 432 | 7584 | 309 | P925 B3  | 0 | 0.0 | 0 | 0 | 1 | 1 | 0 | 98  | 0 | FN1-7584-1 |
| 433 | 7587 | 309 | P925 E7  | 0 | 0.0 | 0 | 0 | 0 | 0 | 0 | 100 | 0 | FN1-7587-1 |
| 434 | 7592 | 309 | P926 B2  | 0 | 0.0 | 0 | 0 | 0 | 0 | 0 | 100 | 0 | FN1-7592-1 |
| 435 | 7592 | 309 | P926 B4  | 0 | 0.7 | 0 | 0 | 1 | 1 | 0 | 97  | 0 | FN1-7592-2 |
| 436 | 7598 | 309 | P926 H3  | 0 | 0.7 | 0 | 0 | 1 | 2 | 0 | 95  | 1 | FN1-7598-1 |
| 437 | 7598 | 309 | P926 H10 | 0 | 0.7 | 1 | 0 | 1 | 1 | 0 | 96  | 1 | FN1-7598-2 |
| 438 | 7600 | 309 | P927 B1  | 0 | 0.0 | 0 | 0 | 0 | 0 | 0 | 100 | 0 | FN1-7600-1 |
| 439 | 7600 | 309 | P927 B5  | 0 | 0.0 | 0 | 0 | 0 | 0 | 0 | 100 | 0 | FN1-7600-2 |
| 440 | 7629 | 310 | P930 C8  | 0 | 1.1 | 0 | 1 | 0 | 0 | 0 | 95  | 1 | FN1-7629-1 |
| 441 | 7640 | 311 | P931 B4  | 0 | 0.0 | 0 | 1 | 0 | 0 | 0 | 96  | 1 | FN1-7640-1 |
| 442 | 7647 | 311 | P931 F1  | 0 | 0.0 | 0 | 3 | 0 | 0 | 0 | 96  | 0 | FN1-7647-1 |
| 443 | 7656 | 311 | P932 F3  | 0 | 1.7 | 0 | 1 | 0 | 0 | 0 | 94  | 1 | FN1-7656-1 |
| 444 | 7666 | 311 | P933 G8  | 0 | 1.0 | 0 | 1 | 0 | 0 | 0 | 95  | 1 | FN1-7666-1 |
| 445 | 7674 | 312 | P934 F3  | 0 | 1.4 | 0 | 1 | 0 | 0 | 0 | 96  | 1 | FN1-7674-1 |

TABLE 3-continued

| | M1 | | | Alkaloid profile (percentage of area under peaks) | | | | | | | | |
|---|---|---|---|---|---|---|---|---|---|---|---|---|
| Seln No. | Seed Line | Tray | Plate/ Position | Mor- phine | Oripavine | Saluta- ridine | Codeine | Reticuline | Lauda- nine | Papa- verine | Thebaine | Nos- capine | Selection Name |
| 446 | 7686 | 312 | P936 A6 | 0 | 0.0 | 0 | 0 | 0 | 0 | 0 | 100 | 0 | FN1-7686-1 |
| 447 | 7702 | 313 | P937 H8 | 0 | 0.9 | 0 | 0 | 0 | 0 | 0 | 98 | 1 | FN1-7702-1 |
| 448 | 7718 | 313 | P939 G6 | 0 | 0.0 | 0 | 0 | 0 | 1 | 0 | 99 | 0 | FN1-7718-1 |
| 450 | 3122 | 132 | P394 E2 | 0 | 0.0 | 0 | 0 | 0 | 5 | 0 | 95 | 0 | FN1-3122-1 |
| 451 | 3123 | 132 | P394 F12 | 0 | 0.0 | 0 | 0 | 0 | 5 | 0 | 95 | 0 | FN1-3123-1 |
| 452 | 3132 | 132 | P395 G11 | 0 | 0.0 | 0 | 0 | 0 | 6 | 0 | 94 | 0 | FN1-3132-1 |
| 453 | 3141 | 132 | P396 G1 | 0 | 0.8 | 0 | 0 | 1 | 1 | 0 | 96 | 1 | FN1-3141-1 |
| 454 | 3141 | 132 | P396 G10 | 0 | 0.0 | 0 | 0 | 0 | 0 | 4 | 96 | 0 | FN1-3141-2 |
| 455 | 3158 | 133 | P398 G6 | 0 | 0.0 | 0 | 0 | 0 | 3 | 0 | 97 | 0 | FN1-3158-1 |
| 456 | 3176 | 134 | P400 G1 | 0 | 0.9 | 0 | 0 | 3 | 1 | 0 | 95 | 0 | FN1-3176-1 |
| 457 | 3206 | 135 | P404 E3 | 0 | 0.0 | 0 | 0 | 0 | 0 | 4 | 96 | 0 | FN1-3206-1 |
| 458 | 3209 | 135 | P404 H11 | 0 | 0.0 | 0 | 0 | 1 | 0 | 2 | 96 | 1 | FN1-3209-1 |
| 459 | 3215 | 135 | P405 F5 | 0 | 1.0 | 0 | 0 | 1 | 0 | 2 | 95 | 1 | FN1-3215-1 |
| 460 | 3228 | 136 | P407 C8 | 0 | 0.0 | 0 | 0 | 1 | 2 | 0 | 97 | 0 | FN1-3228-1 |
| 461 | 3258 | 137 | P410 G4 | 0 | 0.0 | 0 | 0 | 1 | 0 | 4 | 94 | 1 | FN1-3258-1 |
| 462 | 3270 | 138 | P412 B3 | 0 | 0.0 | 0 | 0 | 0 | 5 | 0 | 95 | 0 | FN1-3270-1 |
| 463 | 3288 | 138 | P414 C7 | 0 | 0.0 | 0 | 0 | 0 | 0 | 3 | 97 | 0 | FN1-3288-1 |
| 464 | 3295 | 139 | P415 A2 | 0 | 0.0 | 0 | 0 | 2 | 4 | 0 | 94 | 0 | FN1-3295-1 |
| 465 | 3296 | 139 | P415 B10 | 0 | 0.0 | 0 | 0 | 0 | 3 | 0 | 97 | 0 | FN1-3296-1 |
| 466 | 3296 | 139 | P415 B12 | 0 | 1.0 | 0 | 0 | 0 | 2 | 0 | 97 | 0 | FN1-3296-2 |
| 467 | 3297 | 139 | P415 C12 | 0 | 0.0 | 0 | 0 | 1 | 0 | 3 | 95 | 0 | FN1-3297-1 |
| 468 | 3299 | 139 | P415 E1 | 0 | 0.0 | 0 | 0 | 0 | 0 | 3 | 96 | 1 | FN1-3299-1 |
| 469 | 3300 | 139 | P415 F2 | 0 | 0.0 | 0 | 0 | 1 | 0 | 3 | 95 | 0 | FN1-3300-1 |
| 472 | 3310 | 139 | P416 H4 | 0 | 0.0 | 0 | 0 | 0 | 2 | 0 | 96 | 1 | FN1-3310-1 |
| 473 | 3320 | 140 | P418 B10 | 0 | 0.6 | 0 | 0 | 1 | 2 | 0 | 96 | 1 | FN1-3320-1 |
| 474 | 3326 | 140 | P418 H2 | 0 | 0.0 | 0 | 0 | 0 | 2 | 0 | 98 | 0 | FN1-3326-1 |
| 475 | 3328 | 140 | P419 B2 | 0 | 0.0 | 0 | 0 | 1 | 1 | 0 | 98 | 1 | FN1-3328-1 |
| 476 | 3328 | 140 | P419 B7 | 0 | 0.0 | 0 | 0 | 0 | 0 | 7 | 91 | 0 | FN1-3328-2 |
| 477 | 3306 | 139 | P416 D7 | 0 | 3.9 | 0 | 0 | 0 | 0 | 1 | 94 | 1 | FN1-3306-1 |
| 478 | 3365 | 141 | P423 F3 | 0 | 0.0 | 0 | 0 | 0 | 7 | 0 | 93 | 0 | FN1-3365-1 |
| 479 | 3368 | 141 | P423 H10 | 0 | 0.0 | 0 | 0 | 0 | 0 | 0 | 100 | 0 | FN1-3368-1 |
| 480 | 3376 | 142 | P424 H9 | 0 | 0.0 | 0 | 0 | 0 | 2 | 0 | 98 | 0 | FN1-3376-1 |
| 481 | 3376 | 142 | P424 H11 | 0 | 0.0 | 0 | 0 | 0 | 2 | 0 | 98 | 0 | FN1-3376-2 |
| 482 | 3383 | 142 | P425 G9 | 0 | 0.0 | 0 | 0 | 0 | 0 | 0 | 100 | 0 | FN1-3383-1 |
| 483 | 3386 | 142 | P426 B9 | 0 | 0.0 | 0 | 0 | 0 | 2 | 0 | 98 | 0 | FN1-3386-1 |
| 484 | 3387 | 142 | P426 C5 | 0 | 0.0 | 0 | 0 | 1 | 1 | 0 | 98 | 0 | FN1-3387-1 |
| 485 | 3387 | 142 | P426 C7 | 0 | 0.0 | 0 | 0 | 0 | 0 | 0 | 98 | 2 | FN1-3387-2 |
| 486 | 3388 | 142 | P426 C7 | 0 | 0.0 | 0 | 0 | 0 | 1 | 0 | 97 | 1 | FN1-3388-1 |
| 487 | 3406 | 143 | P428 F12 | 0 | 0.0 | 0 | 0 | 0 | 0 | 0 | 100 | 0 | FN1-3406-1 |
| 488 | 3408 | 143 | P428 H11 | 0 | 1.0 | 0 | 0 | 1 | 1 | 0 | 97 | 0 | FN1-3408-1 |
| 489 | 3413 | 143 | P429 E2 | 0 | 0.0 | 0 | 0 | 2 | 0 | 0 | 98 | 0 | FN1-3413-1 |
| 491 | 3444 | 145 | P433 C12 | 0 | 0.0 | 0 | 0 | 0 | 0 | 0 | 100 | 0 | FN1-3444-1 |
| 493 | 3488 | 146 | P438 F4 | 0 | 0.0 | 0 | 0 | 2 | 0 | 0 | 98 | 0 | FN1-3488-1 |
| 494 | 3492 | 147 | P439 B4 | 0 | 0.0 | 0 | 0 | 4 | 2 | 0 | 93 | 0 | FN1-3492-1 |
| 495 | 3497 | 147 | P439 G3 | 0 | 0.0 | 0 | 0 | 0 | 0 | 0 | 100 | 0 | FN1-3497-1 |
| 496 | 3497 | 147 | P439 G4 | 0 | 0.0 | 0 | 0 | 0 | 0 | 0 | 100 | 0 | FN1-3497-2 |
| 497 | 3497 | 147 | P439 G11 | 0 | 0.0 | 0 | 0 | 0 | 0 | 0 | 100 | 0 | FN1-3497-3 |
| 498 | 3531 | 148 | P443 H1 | 0 | 0.0 | 0 | 0 | 0 | 0 | 0 | 100 | 0 | FN1-3531-1 |
| 500 | 3608 | 151 | P453 C8 | 0 | 1.1 | 0 | 0 | 1 | 0 | 1 | 97 | 0 | FN1-3608-1 |
| 501 | 3612 | 151 | P453 G6 | 0 | 0.0 | 0 | 0 | 0 | 0 | 0 | 100 | 0 | FN1-3612-1 |
| 503 | 3635 | 152 | P456 F1 | 0 | 1.1 | 0 | 0 | 1 | 1 | 0 | 96 | 1 | FN1-3635-1 |
| 504 | 3635 | 152 | P456 F2 | 0 | 0.0 | 0 | 0 | 0 | 0 | 0 | 98 | 0 | FN1-3635-2 |
| 505 | 3635 | 152 | P456 F4 | 0 | 0.7 | 0 | 0 | 0 | 0 | 0 | 95 | 0 | FN1-3635-3 |
| 506 | 3635 | 152 | P456 F9 | 0 | 0.5 | 0 | 0 | 0 | 0 | 0 | 99 | 0 | FN1-3635-4 |
| 507 | 3635 | 152 | P456 F10 | 0 | 0.0 | 0 | 0 | 0 | 0 | 0 | 100 | 0 | FN1-3635-5 |
| 508 | 3635 | 152 | P456 F11 | 0 | 0.2 | 0 | 0 | 0 | 0 | 0 | 99 | 0 | FN1-3635-6 |
| 509 | 3679 | 154 | P461 G5 | 0 | 0.6 | 0 | 0 | 0 | 1 | 0 | 98 | 0 | FN1-3679-1 |
| 510 | 3708 | 155 | P465 D2 | 0 | 0.0 | 0 | 0 | 0 | 0 | 0 | 100 | 0 | FN1-3708-1 |
| 511 | 3710 | 155 | P465 F5 | 0 | 0.0 | 0 | 0 | 0 | 0 | 0 | 100 | 0 | FN1-3710-1 |
| 512 | 3718 | 156 | P466 F5 | 0 | 0.0 | 0 | 0 | 0 | 0 | 0 | 100 | 0 | FN1-3718-1 |
| 513 | 3718 | 156 | P466 F7 | 0 | 1.0 | 0 | 0 | 0 | 0 | 0 | 98 | 1 | FN1-3718-2 |
| 514 | 3770 | 158 | P473 B8 | 0 | 1.6 | 0 | 0 | 1 | 0 | 0 | 97 | 0 | FN1-3770-1 |
| 516 | 3794 | 159 | P476 A7 | 0 | 0.4 | 0 | 0 | 0 | 0 | 0 | 100 | 0 | FN1-3794-1 |
| 517 | 3799 | 159 | P476 F4 | 0 | 0.9 | 0 | 0 | 1 | 0 | 0 | 97 | 1 | FN1-3799-1 |
| 518 | 3803 | 159 | P477 B9 | 0 | 0.9 | 0 | 0 | 1 | 0 | 0 | 98 | 1 | FN1-3803-1 |
| 519 | 3804 | 159 | P477 C6 | 0 | 1.0 | 0 | 0 | 1 | 0 | 0 | 96 | 1 | FN1-3804-1 |
| 520 | 3805 | 159 | P477 D12 | 0 | 1.0 | 0 | 0 | 1 | 0 | 0 | 98 | 1 | FN1-3805-1 |
| 521 | 3817 | 160 | P478 H11 | 0 | 0.0 | 0 | 0 | 0 | 0 | 0 | 100 | 0 | FN1-3817-1 |
| 522 | 3821 | 160 | P479 D1 | 0 | 1.1 | 0 | 0 | 1 | 0 | 0 | 98 | 0 | FN1-3821-1 |
| 523 | 3821 | 160 | P479 D3 | 0 | 1.4 | 0 | 0 | 0 | 0 | 0 | 98 | 1 | FN1-3821-2 |
| 524 | 3821 | 160 | P479 D10 | 0 | 0.0 | 0 | 0 | 0 | 0 | 0 | 100 | 0 | FN1-3821-3 |
| 525 | 3827 | 160 | P480 B6 | 0 | 0.7 | 0 | 0 | 0 | 0 | 0 | 99 | 0 | FN1-3827-1 |
| 526 | 3841 | 161 | P481 H3 | 0 | 0.0 | 0 | 0 | 3 | 0 | 0 | 96 | 1 | FN1-3841-1 |
| 528 | 3978 | 166 | P498 H2 | 0 | 0.0 | 0 | 0 | 0 | 0 | 0 | 100 | 0 | FN1-3978-1 |
| 529 | 3995 | 167 | P501 A5 | 0 | 0.0 | 0 | 0 | 0 | 0 | 0 | 100 | 0 | FN1-3995-1 |

TABLE 3-continued

| | M1 | | | Alkaloid profile (percentage of area under peaks) | | | | | | | | | |
|---|---|---|---|---|---|---|---|---|---|---|---|---|---|
| Seln No. | Seed Line | Tray | Plate/ Position | Mor- phine | Oripavine | Saluta- ridine | Codeine | Reticuline | Lauda- nine | Papa- verine | Thebaine | Nos- capine | Selection Name |
| 531 | 4027 | 169 | P505 A6 | 0 | 0.0 | 0 | 0 | 0 | 0 | 0 | 100 | 0 | FN1-4027-1 |
| 532 | 4027 | 169 | P505 A5 | 0 | 0.6 | 0 | 0 | 0 | 0 | 0 | 99 | 0 | FN1-4027-2 |
| 534 | 4050 | 169 | P507 H3 | 0 | 0.4 | 0 | 0 | 1 | 0 | 0 | 99 | 0 | FN1-4050-1 |
| 535 | 4053 | 170 | P508 C9 | 0 | 0.7 | 0 | 0 | 0 | 0 | 0 | 99 | 0 | FN1-4053-1 |
| 537 | 4093 | 171 | P513 C5 | 0 | 1.0 | 0 | 0 | 2 | 1 | 0 | 94 | 1 | FN1-4093-1 |
| 541 | 4121 | 172 | P516 G9 | 0 | 1.2 | 0 | 0 | 0 | 0 | 0 | 97 | 1 | FN1-4121-1 |
| 542 | 4124 | 173 | P517 B2 | 0 | 0.7 | 0 | 0 | 1 | 1 | 0 | 97 | 1 | FN1-4124-1 |
| 543 | 4128 | 173 | P517 F6 | 1 | 1.3 | 0 | 0 | 1 | 0 | 0 | 94 | 0 | FN1-4128-1 |
| 546 | 4144 | 173 | P519 F12 | 0 | 0.9 | 0 | 0 | 0 | 0 | 0 | 97 | 0 | FN1-4144-1 |
| 547 | 4145 | 173 | P519 G7 | 0 | 0.7 | 0 | 0 | 0 | 0 | 0 | 99 | 0 | FN1-4145-1 |
| 548 | 4145 | 173 | P519 G11 | 0 | 0.5 | 0 | 0 | 0 | 0 | 0 | 97 | 0 | FN1-4145-2 |
| 549 | 4148 | 174 | P520 B7 | 0 | 0.7 | 0 | 0 | 1 | 1 | 0 | 98 | 0 | FN1-4148-1 |

Testing of Poppy Straw Alkaloid Content in M2 Generation

Capsules were harvested from the greenhouse as they matured. Seed was removed and weighed into seed envelopes. The poppy straw was placed into 50 mL BD Falcon™ tubes (BD Biosciences, San Jose, Calif.) without grinding and dried either on the lab bench for several days at room temperature or in the laboratory oven at 50° C. for 3 hours. Where capsules were large, only a portion of the capsule was used for analysis, the rest being discarded.

For analysis, the poppy straw was weighed, and either 5 mL or 10 mL acid extractant (5% ethanol ("EtOH"), 0.17% phosphoric acid) added, depending on whether the straw samples weighed less or more than 0.2 g respectively. The samples were agitated with a Ratek orbital shaker (Ratek Instruments, *Boronia*, Victoria, Australia) for 3 hours. The liquid phase was then filtered using Pall AcroPrep™ 96 filter plates (PN S5045), and the filtrate was analysed for alkaloids using a Waters Acquity UPLC® system (Waters Corporation, Milford, Mass.). The UPLC method used was the same 2.5 minute method as used for leaf samples. Additional extractant was transferred to 1.2 mL wells in 96 well plates, sealed and frozen in case further analysis was required.

The alkaloid contents and profiles were calculated from the UPLC results and weight data. Where the weight was <0.1 g, the weight was deemed as 0.1 g.

The seeds were allowed to dry on the laboratory bench, catalogued and stored.

Of the 549 M2 plants originally selected, 434 survived to produce at least one capsule for harvest (79%). A further 6 mislabeled capsules were harvested, so their M1 parents were not known. 395 plants produced some seed, although 58 had <0.06 g seed, and only 171 plants produced more than 1 g seed.

Due to the potential lack of accuracy with the alkaloid content data (due to low capsule weights and large particle sizes), this data was analysed further only after conversion to alkaloid profiles: i.e. the alkaloid contents in comparison with the total alkaloid content.

Where multiple capsules were harvested from one plant, the mean was determined using Minitab 14 statistical software (Minitab Inc., State College, Pa.).

Table 4, below, shows the results for 133 M2 selections from 92 independent M1 plants that were high in thebaine (>90% of alkaloids) and low in oripavine (<10%). Thirty six M2 selections from 27 independent M1 plants had more than 95% of the alkaloid in the straw as thebaine. Twenty one selections from 16 independent M1 plants had more than 96% of the alkaloid in the straw as thebaine. Eight selections from 6 independent M1 plants had more than 97% of the alkaloid in the straw as thebaine. One selection, FN1-900-5, was identified that had more than 98% of its alkaloid present as thebaine. It can be seen that the oripavine content in the straw of these plants was very low, with several selections having less than 1% of the alkaloid combination, and some with less than 0.5% of the alkaloid combination. All "thebaine-only" plants however contained a small proportion of oripavine in their poppy straw.

TABLE 4

Alkaloid profiles (based on alkaloid concentrations in poppy straw) of M2 plants selected for high thebaine and low oripavine. Means are shown where the number of capsules (caps) was more than one.

| Seln no. | Seln name | Caps | Morphine | Oripavine | Codeine | Salutaridine | Reticuline | Laudanine | Papaverine | Thebaine | Noscapine |
|---|---|---|---|---|---|---|---|---|---|---|---|
| 68 | FN1-291-1 | 15 | 0.4 | 4.7 | 0 | 0.2 | 0.9 | 0.1 | 0.2 | 93.3 | 0.2 |
| 106 | FN1-5574 | 1 | 0 | 2.8 | 0 | 0.3 | 6.2 | 0 | 0 | 90.7 | 0 |
| 110 | FN1-601-1 | 1 | 0.1 | 0.4 | 0 | 0 | 1.5 | 0.2 | 0 | 97.6 | 0.1 |
| 139 | FN1-809-1 | 5 | 0 | 1.6 | 0.1 | 0.6 | 4.9 | 0 | 0 | 92.7 | 0 |
| 140 | FN1-809-2 | 2 | 0 | 1.7 | 0.1 | 0.3 | 2.1 | 0 | 0 | 95.6 | 0.2 |
| 144 | FN1-846-1 | 1 | 0 | 0.1 | 0 | 0 | 2.5 | 0.1 | 0 | 97.2 | 0 |
| 145 | FN1-846-2 | 3 | 2.6 | 0.4 | 0 | 0 | 3.1 | 0.2 | 0 | 93.5 | 0.1 |
| 149 | FN1-875-1 | 3 | 1.8 | 3.6 | 0 | 0.1 | 1.9 | 0.1 | 0 | 92.4 | 0.1 |
| 153 | FN1-900-1 | 3 | 6 | 0.6 | 0 | 0.1 | 1.5 | 0.2 | 0 | 97.5 | 0.1 |
| 154 | FN1-900-2 | 3 | 0 | 0.6 | 0 | 0.2 | 1.8 | 0.2 | 0 | 97.1 | 0.1 |
| 155 | FN1-900-3 | 3 | 0.8 | 0.5 | 0 | 0 | 2.3 | 0.2 | 0 | 96.1 | 0.1 |
| 156 | FN1-900-4 | 7 | 2.3 | 0.6 | 0 | 0.2 | 1.5 | 0.2 | 0 | 94.9 | 0.3 |
| 157 | FN1-900-5 | 1 | 0 | 0.6 | 0 | 0.2 | 1 | 0.1 | 0 | 98 | 0.1 |
| 161 | FN1-916-1 | 4 | 0.6 | 5.5 | 0 | 0.1 | 1.3 | 0.1 | 0 | 92.3 | 0.1 |

TABLE 4-continued

Alkaloid profiles (based on alkaloid concentrations in poppy straw) of M2 plants selected for high thebaine and low oripavine. Means are shown where the number of capsules (caps) was more than one.

| Seln no. | Seln name | Caps | Morphine | Oripavine | Codeine | Salutaridine | Reticuline | Laudanine | Papaverine | Thebaine | Noscapine |
|---|---|---|---|---|---|---|---|---|---|---|---|
| 167 | FN1-998-1 | 1 | 1.5 | 1.1 | 0.6 | 0 | 2.4 | 0 | 0 | 91.4 | 3.1 |
| 168 | FN1-998-2 | 2 | 0 | 1 | 0.1 | 0.3 | 2.4 | 0 | 0 | 96.3 | 0 |
| 172 | FN1-1027-1 | 1 | 0 | 2.2 | 0 | 0 | 3.1 | 0 | 0 | 94.7 | 0 |
| 173 | FN1-1027-2 | 4 | 0.3 | 2.6 | 0 | 0.3 | 2 | 0.1 | 0 | 94.6 | 0.2 |
| 174 | FN1-1050-1 | 8 | 3.5 | 1 | 0 | 0.4 | 1.3 | 0 | 0 | 93.7 | 0 |
| 175 | FN1-1050-2 | 2 | 0.2 | 3 | 0 | 0.1 | 1.7 | 0 | 0 | 94.8 | 0.2 |
| 180 | FN1-1123-1 | 2 | 0 | 1 | 0 | 0.4 | 3.6 | 0 | 0 | 95.2 | 0 |
| 184 | FN1-1139-2 | 1 | 0 | 5.7 | 0 | 0.1 | 1.3 | 0.2 | 0 | 92.5 | 0.1 |
| 188 | FN1-1153-1 | 10 | 0.1 | 7.9 | 0 | 0 | 1.3 | 0.1 | 0 | 90.6 | 0 |
| 199 | FN1-1185-1 | 3 | 0 | 2.9 | 0 | 0.1 | 2.7 | 0.2 | 0 | 93.9 | 0.2 |
| 208 | FN1-1242-1 | 3 | 1.2 | 0.6 | 0 | 0.1 | 2.8 | 0.2 | 0 | 95 | 0.1 |
| 209 | FN1-1242-2 | 2 | 0 | 0.3 | 0 | 0 | 2.8 | 0.2 | 0 | 96.7 | 0.1 |
| 210 | FN1-1242-3 | 3 | 0 | 0.4 | 0 | 0.1 | 1.7 | 0.1 | 0 | 97.5 | 0.1 |
| 219 | FN1-1326-2 | 4 | 0.5 | 6.9 | 0 | 0.1 | 1.8 | 0.1 | 0 | 90.6 | 0.1 |
| 240 | FN1-1444-1 | 4 | 0 | 5.2 | 0 | 0 | 1.4 | 0.2 | 0 | 93.2 | 0.2 |
| 249 | FN1-1534-1 | 6 | 0.1 | 0.7 | 0 | 0.5 | 2.6 | 0 | 0 | 96.1 | 0 |
| 250 | FN1-1534-2 | 2 | 0.5 | 1.5 | 0 | 0.5 | 4.9 | 0 | 0 | 92.5 | 0.2 |
| 255 | FN1-1571-1 | 2 | 0.4 | 1.5 | 0 | 0.5 | 5.7 | 0 | 0 | 92 | 0 |
| 256 | FN1-1571-2 | 2 | 0.5 | 1.8 | 0 | 0.7 | 4.2 | 0 | 0 | 93 | 0 |
| 257 | FN1-1571-3 | 3 | 0.6 | 1.5 | 0 | 0.5 | 2.5 | 0 | 0 | 94.7 | 0 |
| 258 | FN1-1571-4 | 2 | 0.7 | 1.9 | 0 | 0.4 | 6.9 | 0.1 | 0 | 90.2 | 0 |
| 259 | FN1-1571-5 | 1 | 0 | 1.5 | 0 | 0.7 | 3.4 | 0 | 0 | 94.3 | 0 |
| 260 | FN1-1571-6 | 4 | 0.1 | 1.2 | 0.1 | 0.5 | 4.9 | 0 | 0 | 93.2 | 0 |
| 261 | FN1-1571-7 | 3 | 0 | 1.3 | 0 | 0.3 | 5 | 0 | 0 | 93.3 | 0 |
| 262 | FN1-1571-8 | 1 | 1 | 1.7 | 0 | 0.8 | 2.3 | 0 | 0 | 94 | 0.2 |
| 263 | FN1-1571-9 | 3 | 0.6 | 1.8 | 0 | 0.8 | 4.6 | 0 | 0.1 | 92.1 | 0 |
| 264 | FN1-1571-10 | 4 | 0.2 | 1.4 | 0.1 | 0.4 | 5 | 0 | 0 | 92.9 | 0 |
| 270 | FN1-1625-1 | 1 | 0 | 2.3 | 0 | 0.3 | 1.2 | 0.3 | 0 | 95.7 | 0.1 |
| 273 | FN1-1662-1 | 1 | 0 | 4.6 | 0 | 0.1 | 1.4 | 0 | 0.6 | 93.1 | 0.3 |
| 275 | FN1-1701-1 | 2 | 0 | 2.9 | 0.1 | 0.1 | 2.2 | 0.2 | 0 | 94.6 | 0.1 |
| 279 | FN1-1719-1 | 4 | 0.2 | 0.3 | 0 | 0 | 2.6 | 0.1 | 0 | 96.6 | 0.1 |
| 280 | FN1-1741-1 | 1 | 0 | 3.1 | 0 | 0 | 3.4 | 0.2 | 0 | 93 | 0.3 |
| 284 | FN1-1771-1 | 3 | 0 | 2 | 0 | 0.3 | 1.1 | 0.1 | 0 | 96.6 | 0.1 |
| 285 | FN1-1771-2 | 2 | 0 | 4.8 | 0 | 0.2 | 1.6 | 0 | 0 | 93.4 | 0.1 |
| 292 | FN1-1841-1 | 1 | 0 | 4.7 | 0 | 0 | 1.3 | 0.3 | 0 | 93.7 | 6 |
| 296 | FN1-1869-2 | 1 | 0 | 2.2 | 0 | 0.4 | 1.7 | 0.1 | 0 | 95.5 | 0.1 |
| 299 | FN1-1913-1 | 3 | 0 | 3 | 0 | 0 | 1.8 | 0 | 0 | 95.1 | 0 |
| 307 | FN2-2085-1 | 1 | 0 | 4 | 0 | 0 | 2.8 | 0.1 | 0 | 93 | 0.1 |
| 309 | FN1-2103-1 | 5 | 0.1 | 6.8 | 0 | 0.1 | 2.1 | 0.2 | 0 | 90.7 | 0 |
| 312 | FN1-2152-1 | 3 | 0 | 2.1 | 0 | 0.1 | 5.6 | 0 | 0 | 92.3 | 0 |
| 313 | FN1-2152-2 | 2 | 0 | 0.9 | 0.2 | 0.6 | 3.6 | 0.1 | 0 | 94.8 | 0 |
| 314 | FN1-2152-3 | 3 | 0 | 1.1 | d | 0.7 | 3.4 | 0 | 0.1 | 94.7 | 0 |
| 315 | FN1-2152-4 | 2 | 0 | 1.2 | 0 | 0.5 | 3.3 | 0 | 0 | 95 | 0 |
| 318 | FN1-2172-1 | 1 | 0 | 4 | 0 | 0 | 4.9 | 0.2 | 0 | 90.8 | 0.1 |
| 319 | FN1-2175-1 | 1 | 0 | 8 | 0 | 0 | 1.2 | 0.1 | 0 | 90.4 | 0.3 |
| 321 | FN1-2186-1 | 2 | 0 | 3.5 | 0.1 | 0.4 | 1.6 | 0 | 0.3 | 94.1 | 0.1 |
| 325 | FN1-2199-1 | 3 | 0 | 0.4 | 0 | 0.1 | 4.3 | 0.2 | 0 | 95 | 0 |
| 326 | FN1-2199-2 | 2 | 0 | 0.3 | 0 | 0.1 | 3.6 | 0.1 | 0 | 95.9 | 0.2 |
| 339 | FN1-2233-1 | 1 | 0 | 2.8 | 0 | 0.1 | 1.4 | 0 | 0 | 95.7 | 0 |
| 343 | FN1-2245-1 | 2 | 0 | 6.1 | 0 | 0.1 | 1.5 | 0.1 | 0 | 92.1 | 0.2 |
| 364 | FN1-2437-1 | 3 | 0 | 0.5 | 0 | 0.1 | 3.1 | 0.2 | 0 | 96.2 | 0 |
| 367 | FN1-2492-1 | 1 | 0 | 5.5 | 0 | 0.1 | 2.2 | 0.1 | 0 | 92.1 | 0.1 |
| 374 | FN1-2604-1 | 3 | 0 | 0.3 | 0.1 | 0.1 | 5.4 | 0.2 | 0 | 93.7 | 0.2 |
| 377 | FN1-7299-3 | 2 | 0 | 2.4 | 0.1 | 0.2 | 1.3 | 0.1 | 0 | 95.8 | 0.2 |
| 378 | FN1-7299-4 | 2 | 0 | 3.3 | 0.1 | 0.2 | 1.7 | 0.2 | 0 | 94.6 | 0.2 |
| 379 | FN1-7299-5 | 1 | 0 | 2.7 | 0.1 | 0.4 | 1.6 | 0.2 | 0 | 94.7 | 0.3 |
| 380 | FN1-7299-6 | 2 | 0 | 2 | 0 | 0.1 | 1 | 0.1 | 0 | 96.8 | 0.1 |
| 384 | FN1-7306-1 | 1 | 0 | 6.8 | 0 | 0 | 0 | 0 | 0 | 93.1 | 0.1 |
| 396 | FN1-7354-2 | 1 | 0 | 0.6 | 0 | 1.2 | 4.3 | 0 | 0 | 93.9 | 0 |
| 400 | FN1-7378-1 | 1 | 0 | 4.4 | 0 | 0.1 | 1.7 | 0 | 0 | 93.5 | 0.3 |
| 404 | FN1-7397-1 | 1 | 0 | 8 | 0 | 0 | 1 | 0 | 0 | 91 | 0 |
| 407 | FN1-7445-1 | 1 | 0 | 5.6 | 0 | 0 | 2.3 | 0.2 | 0 | 91.9 | 0 |
| 408 | FN1-7447-1 | 1 | 0 | 3.3 | 0 | 0.1 | 3.5 | 0.1 | 0 | 92.8 | 0.2 |
| 409 | FN1-7448-1 | 1 | 0 | 5.2 | 0 | 0.1 | 2.7 | 0.1 | 0 | 91.8 | 0.2 |
| 414 | FN1-7471-1 | 1 | 0 | 3.7 | 0.1 | 0 | 3.2 | 0.2 | 0 | 92.3 | 0.4 |
| 416 | FN1-7491-1 | 1 | 0 | 6.9 | 0 | 0.1 | 1.1 | 0.2 | 0 | 91.8 | 0 |
| 417 | FN1-7499-1 | 1 | 0 | 5.4 | 0 | 0 | 1.6 | 0.2 | 0 | 92.6 | 0.3 |
| 421 | FN1-7525-1 | 2 | 0 | 5.5 | 0 | 0.1 | 1.6 | 0 | 0.4 | 92.5 | 0.1 |
| 422 | FN1-7529-1 | 1 | 0 | 6.7 | 0 | 0.1 | 2.2 | 0 | 0.9 | 90 | 0.2 |
| 426 | FN1-7551-1 | 1 | 0 | 4.6 | 0 | 0.1 | 2.3 | 0.1 | 0 | 92.8 | 0.1 |
| 433 | FN1-7587-1 | 1 | 0 | 8.4 | 0 | 0 | 0.6 | 0.1 | 0 | 90.8 | 0 |
| 434 | FN1-7592-1 | 1 | 0.5 | 2 | 0 | 0.6 | 0.5 | 0 | 0 | 96.3 | 0 |
| 436 | FN1-7598-1 | 1 | 0 | 5.7 | 0 | 0.1 | 2.2 | 0.1 | 0 | 91.7 | 0.2 |

TABLE 4-continued

Alkaloid profiles (based on alkaloid concentrations in poppy straw) of M2 plants selected for high thebaine and low oripavine. Means are shown where the number of capsules (caps) was more than one.

| Seln no. | Seln name | Caps | Morphine | Oripavine | Codeine | Salutaridine | Reticuline | Laudanine | Papaverine | Thebaine | Noscapine |
|---|---|---|---|---|---|---|---|---|---|---|---|
| 437 | FN1-7598-2 | 1 | 0 | 4.5 | 0 | 0 | 1.8 | 0 | 0 | 93.5 | 0.3 |
| 443 | FN1-7656-1 | 1 | 0 | 7.7 | 0 | 0.1 | 1.4 | 0 | 0.5 | 90.2 | 0.2 |
| 445 | FN1-7674-1 | 5 | 0 | 2.4 | 0 | 0 | 2.6 | 0.1 | 0.2 | 94.5 | 0.2 |
| 446 | FN1-7686-1 | 2 | 0 | 1.5 | 0 | 0.4 | 4.9 | 0.1 | 0 | 93.3 | 0 |
| 447 | FN1-7702-1 | 1 | 0 | 3.2 | 0 | 0.1 | 2 | 0 | 0 | 94.6 | 0 |
| 453 | FN1-3141-1 | 1 | 0 | 4.6 | 0 | 0.1 | 2.3 | 0.2 | 0 | 92.7 | 0.1 |
| 454 | FN1-3141-2 | 1 | 0 | 8.1 | 0 | 0 | 1.6 | 0.2 | 0 | 90.1 | 0 |
| 455 | FN1-3158-1 | 2 | 0 | 8 | 0 | 0.1 | 1.6 | 0.2 | 0 | 90.2 | 0.1 |
| 458 | FN1-3209-1 | 1 | 0 | 5 | 0 | 0 | 2 | 0.2 | 0 | 92.5 | 0.2 |
| 461 | FN1-3258-1 | 1 | 0.3 | 6.1 | 0 | 0 | 1.8 | 0.2 | 0 | 91.6 | 0 |
| 463 | FN1-3288-1 | 1 | 0 | 5.8 | 0 | 0.1 | 1.8 | 0.2 | 0 | 92.1 | 0.1 |
| 465 | FN1-3296-1 | 1 | 0 | 8.7 | 0 | 0.1 | 1.1 | 0.1 | 0 | 90.1 | 0 |
| 466 | FN1-3296-2 | 1 | 0 | 2.2 | 0.4 | 0.2 | 1.8 | 0.2 | 0 | 95.2 | 0.1 |
| 474 | FN1-3326-1 | 1 | 0 | 7.2 | 0 | 0.1 | 1.6 | 0.2 | 0 | 90.9 | 0.1 |
| 475 | FN1-3328-1 | 2 | 0 | 0.4 | 0 | 0.2 | 6.5 | 0.3 | 0 | 92.7 | 0 |
| 476 | FN1-3328-2 | 1 | 0 | 0.4 | 0 | 0.1 | 2.9 | 0.2 | 0 | 96.3 | 0.1 |
| 477 | FN1-3306-1 | 2 | 0 | 2.8 | 0.1 | 0.1 | 2.5 | 0.1 | 0 | 94.3 | 0.3 |
| 480 | FN1-3376-1 | 1 | 0 | 5 | 0 | 0 | 1.4 | 0.3 | 0 | 93.3 | 0 |
| 483 | FN1-3386-1 | 1 | 0 | 4.6 | 0.1 | 0.1 | 2.6 | 0 | 1.1 | 91.2 | 0.4 |
| 486 | FN1-3388-1 | 1 | 0 | 5.5 | 0 | 0.1 | 3.1 | 0.2 | 0 | 90.8 | 0.3 |
| 489 | FN1-3413-1 | 1 | 0 | 6.3 | 0 | 0.1 | 2.8 | 0.1 | 0 | 90.6 | 0.2 |
| 495 | FN1-3497-1 | 1 | 0 | 1.4 | 0 | 0 | 4 | 0 | 0 | 94.6 | 0 |
| 496 | FN1-3497-2 | 2 | 0 | 1.2 | 0 | 0.2 | 2.8 | 0 | 0 | 96 | 0 |
| 497 | FN1-3497-3 | 2 | 0 | 1.2 | 0 | 0.2 | 4.7 | 0 | 0 | 94 | 0 |
| 503 | FN1-3635-1 | 2 | 0 | 1.2 | 0 | 0.3 | 4 | 0.1 | 0 | 94.3 | 0.2 |
| 504 | FN1-3635-2 | 1 | 0 | 1.3 | 0 | 0 | 2.8 | 0 | 0 | 95.9 | 0 |
| 506 | FN1-3635-4 | 1 | 0 | 1.2 | 0 | 0.4 | 3.6 | 0 | 0 | 94.8 | 0 |
| 507 | FN1-3635-5 | 1 | 0 | 1 | 0 | 0 | 1.9 | 0 | 0 | 97.1 | 0 |
| 508 | FN1-3635-6 | 1 | 0 | 1.3 | 0 | 0 | 2.2 | 0 | 0 | 96.5 | 0 |
| 509 | FN1-3679-1 | 1 | 0 | 3.2 | 0.2 | 0.1 | 4.6 | 0 | 0 | 91.7 | 0.3 |
| 511 | FN1-3710-1 | 1 | 0 | 8.1 | 0 | 0 | 1.3 | 0.2 | 0 | 90.5 | 0 |
| 512 | FN1-3718-1 | 1 | 0 | 4 | 0 | 0.1 | 1.5 | 0.2 | 0 | 94.2 | 0.1 |
| 516 | FN1-3794-1 | 2 | 0 | 0.1 | 0 | 0.1 | 4 | 0.2 | 0 | 95.7 | 0.1 |
| 521 | FN1-3817-1 | 1 | 0 | 7 | 0 | 0 | 1.5 | 0.1 | 0 | 91.4 | 0 |
| 522 | FN1-3821-1 | 1 | 0.9 | 5.9 | 0 | 0 | 2.5 | 0.2 | 0 | 90.3 | 0.3 |
| 523 | FN1-3821-2 | 1 | 0 | 3.3 | 0 | 0.1 | 3.9 | 0.2 | 0 | 92 | 0.4 |
| 524 | FN1-3821-3 | 1 | 0 | 6.7 | 0 | 0 | 2.3 | 0.1 | 0 | 90.9 | 0 |
| 525 | FN1-3827-1 | 1 | 0 | 4.7 | 0 | 0 | 1 | 0.2 | 0 | 94.1 | 0 |
| 528 | FN1-3978-1 | 1 | 0 | 3 | 0 | 0 | 2.7 | 0.3 | 0 | 94 | 0 |
| 529 | FN1-3995-1 | 2 | 0 | 0.8 | 0 | 0.1 | 3.4 | 0.2 | 0 | 95.5 | 0.2 |
| 534 | FN1-4050-1 | 2 | 0 | 0.1 | 0 | 0.1 | 2.7 | 0.1 | 0 | 97 | 0.1 |
| 535 | FN1-4053-1 | 3 | 0 | 5.1 | 0 | 0 | 1.7 | 0.2 | 0 | 93.1 | 0 |
| 541 | FN1-4121-1 | 1 | 0 | 2.2 | 0 | 0 | 1.6 | 0.3 | 0 | 96 | 0 |
| 542 | FN1-4124-1 | 2 | 0 | 6.9 | 0 | 0 | 1.4 | 0.1 | 0 | 91.8 | 0 |
| 546 | FN1-4144-1 | 1 | 0 | 4 | 0 | 0 | 2.9 | 0.3 | 0 | 92.7 | 0 |
| 548 | FN1-4145-2 | 1 | 0 | 1.9 | 0 | 0.5 | 4.1 | 0 | 0 | 93.5 | 0 |

Growing and Evaluation of M3 Generation

Two of the highest thebaine lines were selected for increase in a greenhouse over winter 2007 to provide data to confirm their alkaloid composition and genetic stability. Thus, the plants grown in this experiment were the M3 generation.

The pots were sown in the greenhouse on 11 Apr. 2007 in double rows, with 120 pots in each double row. Each pot was thinned to 6 plants. Greenhouse conditions were as used previously except that high intensity lights were used to maintain light intensities of approximately 9900 lux for 12 hours per day.

At green capsule stage, latex samples were taken from 24 randomly chosen plants from each line. The samples were obtained from the stigmatic discs using the ray-pluck technique. A stigmatic ray was removed from each plant and dropped into acid extraction solution (5% EtOH, 0.17% $H_3PO_4$) in a filter plate (Pall AcroPrep™ 96 Filter Plate 0.2 µm GHP, NTRL, 350 µL). The rest of the procedure was the same as for leaf latex tests. A separate trial established that there was no significant difference in thebaine or oripavine results attributable to using acid extraction solution instead of latex extraction solution as used previously.

Table 5 shows the results of the latex testing at the green capsule stage for the M3 Generation. The number of plants randomly sampled and tested is shown as "N". All plants tested had the same alkaloid profile of high thebaine and substantially no oripavine or morphine.

TABLE 5

Results of the green capsule stage testing. The table shows the percentage of area under chromatogram peaks.

| Selection | N | Thebaine Mean | SE | Oripavine Mean | SE | Morphine Mean | SE | Codeine Mean | SE | Papaverine Mean | SE | Noscapine Mean | SE | Thebaine ratio Mean | SE | Norman ratio Mean | SE |
|---|---|---|---|---|---|---|---|---|---|---|---|---|---|---|---|---|---|
| FN1-900-1 | 23 | 98.0 | 0.1 | 0.5 | 0.1 | 0.2 | 0.0 | 0.7 | 0.0 | 0.6 | 0.0 | 0.0 | 0.0 | 0.995 | 0.001 | 0.99 | 0.00 |
| FN1-1242-3 | 24 | 98.6 | 0.0 | 0.2 | 0.0 | 0.1 | 0.0 | 0.6 | 0.0 | 0.5 | 0.0 | 0.0 | 0.0 | 0.998 | 0.000 | 0.99 | 0.00 |

Thebaine ratio is the thebaine area divided by the total of the thebaine and oripavine areas Norman ratio is the sum of the thebaine and oripavine areas divided by the sum of morphine, oripavine, codeine and thebaine areas When the capsules were dry, the plants were harvested by hand. The harvested capsules were weighed, and then threshed and sieved to separate seed and straw. The straw was sub-sampled and ground to 2 mm.

The straw was extracted using acid extraction solution (5% EtOH, 0.17% $H_3PO_4$), and analysed using Waters Acquity ULPC® for alkaloid content against standard alkaloid solutions on a dry weight basis. The loss on drying (LOD) of the straw was determined by heating a sample at 88° C. for 9 minutes using an infrared (IR) balance (A&D Company Ltd Model AD4717, Japan).

Peak area data was used to calculate alkaloid concentration in the straw according to the following calculation:

$$\text{Alkaloid content}(\%) = \frac{0.1 \times \frac{SPLA \times STDC}{STDA} \times \frac{(EV + LOD\% \times SW)}{100}}{\frac{SW \times (100 - LOD\%)}{100}} \times \frac{STDI}{SPLI}$$

where SPLA is the area under the sample peak of interest

STDC is the concentration of the standard alkaloid in mg/mL

STDA is the area under the standard peak

EV is extractant volume in mL

LOD % is the loss on drying of the straw, expressed as a percentage

SW is straw weight extracted in grams.

STDI is the volume of standard injected in microlitres

SPLI is the volume of sample injected in microlitres

FN1-900-1 had noticeably low vigour compared with the other lines. The vigour of FN1-1242-3 appeared to be normal. The vigour differences became apparent well after establishment, indicating that it was not a seed quality effect.

Table 6 shows the loss on drying of straw and the mean alkaloid content of the duplicate straw samples as determined by UPLC.

TABLE 6

Amount of capsule, straw and seed harvested, loss on drying (LOD) of straw, and alkaloid content determined by UPLC.

| Selection | Yield (kg/line) air dry basis | | | Straw/ Capsule ratio | Straw LOD (%) | Alkaloid content (dry weight basis) | | Total % | Thebaine ratio |
|---|---|---|---|---|---|---|---|---|---|
| | Capsule | Seed | Straw | | | Thebaine % (DWB) | Oripavine % (DWB) | | |
| FN1-900-1 | 2.91 | 1.27 | 1.64 | 0.56 | 7.3 | 3.07 | 0.01 | 3.08 | 1.00 |
| FN-1-1242-3 | 3.33 | 1.22 | 2.11 | 0.63 | 7.8 | 3.23 | 0.02 | 3.25 | 0.99 |

Thebaine ratio is the thebaine content divided by the sum of thebaine content and oripavine content.

The results show that the poppy straw in the two lines FN1-900-1 and FN1-1242-3 are very high in thebaine content, and very low (0.01% and 0.02%, respectively, in oripavine content). There were no other alkaloids (i.e., morphine, codeine, salutaridine, reticuline, laudanine, papaverine and noscapine) detected using the method described.

Growing and Evaluation of M4 Generation

Using seed harvested from the M3 generation, 2 large field plots of FN1-1242-3 and one of FN1-900-1 were grown using commercial equipment and methods. No growth regulator sprays were used. Table 7 summarises the alkaloid contents achieved in these crops. At the first site (Elphinstone, Circular Head district of Tasmania), both selections were grown, along with the Norman parent line, WF03-0802. Hand-picked samples taken from the plots assayed at over 5.0% thebaine, and 0.02% oripavine. Machine harvested samples assayed at 4.65% thebaine and 0.02% oripavine (FN1 lines combined). The Norman parent line in the same paddock assayed at 3.05% thebaine and 0.89% oripavine.

At Roebuck's (Merseylea district of Tasmania), the FN1-1242-3 crop assayed at 4.36% thebaine and 0.02% oripavine, whilst the Norman parent line WF03-0802 assayed at an average of 2.08% thebaine and 0.75% oripavine. This data shows that the thebaine-only trait has been inherited into the M4 generation, and that it enables the plants to accumulate very high contents of thebaine.

The method used for the straw analysis is as follows. Ten gram samples of ground straw were extracted with 100 mL extraction solution. The extraction solution comprised 30% ethanol and 10% glacial acetic acid. The samples were shaken for 25 minutes and then filtered through Whatman No. 6 filter paper. The solutions were analysed using a Waters Alliance HPLC system fitted with a Alltech Platinum C18 column, 7 mm×53 mm, with 3 micron packing.

The mobile phase consisted of 8 mL triethylamine, 125 acetonitrile and 950 mL MilliQ water, adjusted to pH 4.1 with phosphoric acid. The flow rate was 3 mL/minute and the column was maintained at 40 C. The alkaloids were detected using a UV detector at 284 nm.

The loss on drying (LOD) of the straw was determined by heating a sample at 88° C. for 9 minutes using an infrared (IR) balance (A&D Company Ltd Model AD4717, Japan).

Alkaloid concentrations were determined by comparison with standard solutions, and results calculated on a dry weight basis. The thebaine and oripavine peaks in these samples accounted for over 98%, and morphine and codeine accounted for less than 1%, of the alkaloid peak area, indicating that there was substantially no morphine and codeine in these samples.

TABLE 7

Summary of commercial results for thebaine-only lines (M4 generation), compared with parent line.

| Grower/Load No | | Description | Line | Thebaine % | Oripavine % | Total % |
| --- | --- | --- | --- | --- | --- | --- |
| Elphinstone | 1273 | Hand picked samples | FN1-1242-3 | 5.10 | 0.02 | 5.12 |
| | 1274 | | FN1-900-1 | 5.25 | 0.02 | 5.27 |
| | 1302 | Parent line control (machine harvested) | WF03-0802 | 3.05 | 0.89 | 3.94 |
| | 1312 | FN1 lines combined (machine harvested) | FN1-1242-3 FN1-900-1 | 4.65 | 0.02 | 4.67 |
| Roebuck | 1047 | Parent line control | WF03-0802 | 2.07 | 0.77 | 2.84 |
| | 1060 | Parent line control | WF03-0802 | 2.09 | 0.73 | 2.82 |
| | 1115 | FN1 line | FN1-1242-3 | 4.36 | 0.02 | 4.38 |

Growing and Evaluation of M5 Generation

Seeds of the M5 generation of FN1-1242-3 were sown in a field trial at Gawler, Tasmania on 29 Aug. 2008, along with seeds of the parent line WF03-0802. Both lines were sown in three blocked replications in plots 5 m long by 1.6 m wide. Standard commercial practices were used to grow the trial. No growth regulator sprays were used. The trial was harvested on 19 Feb. 2009 by hand picking all the capsules within 2 m$^2$ quadrats within each plot. The samples were threshed and the poppy straw weighed. After grinding to <2 mm, the poppy straw was extracted and analysed using the same method as used for the M3 generation (described above). Table 8 shows the mean alkaloid contents in the straw and the alkaloid yields per hectare. In this example, the thebaine content of the straw of FN1-1242-3 is 96.3% of the total, and oripavine content is 1.47% of the total, where the total is the sum of morphine, codeine, thebaine and oripavine content of the poppy straw.

TABLE 8

Summary of trial results for thebaine-only line FN1-1242-3 (M5 generation), compared with parent line.

| Line | Alkaloid content % (dry weight basis) | | | | | Alkaloid yield (kg/hectare) | | Thebaine ratio |
|---|---|---|---|---|---|---|---|---|
| | Morphine | Codeine | Thebaine | Oripavine | Total | Thebaine | Oripavine | |
| WF03-0802 | 0.13 | 0.00 | 2.54 | 1.71 | 4.38 | 29.0 | 19.6 | 0.60 |
| FN1-1242-3 | 0.09 | 0.00 | 3.92 | 0.06 | 4.07 | 58.6 | 0.95 | 0.98 |

Total is the sum of the contents of morphine, codeine, thebaine and oripavine.
Thebaine ratio is the thebaine content divided by the sum of thebaine content and oripavine content.
Alkaloid yield is obtained by multiplying the alkaloid content by the straw yield.

Example 2

Latex Extraction

Reagent

Latex Extraction Buffer: 23 g of ammonium dihydrogen phosphate was dissolved in approximately 750 mL deionised water and 200 mL of ethanol added, and made up to 1 L with deionised water.

Method

Isocratic Method:

A Pall AcroPrep™ 96 well, 0.2 μm GHP filter plate was placed on a 96 well, 350 μL collection plate. Both filter and collection plate were labeled and 280 μL of buffer pipetted into each well of the filter plate using a multipipette. Using forceps, a leaf tip approx 5 mm×5 mm was torn off from the plant to be tested and added to the extractant. The latex will bleed into the solution over time.

The sample was allowed to incubate at room temperature for at least 30 minutes. The sample was filtered using a vacuum manifold (Pall Corporation product No. 5017). The collection plate was covered with Abgene® adhesive PCR sealing foil (Cat #: AB-0626) to prevent evaporation. The collection plate can be stored in the refrigerator or freezer pending analysis.

Analysis Method

Instrument:
Waters Acquity UPLC®, with Sample Organiser and Tunable Ultra Violet (TUV) detector
Waters Column, Bridged Ethyl Hybrid (BEH) particles, C18, 1.7 μm, 2.1×50 mm
TUV detector, wavelength 284 nm
Reagents:
Mobile Phase A—9% methanol, 0.1% formic acid, adjusted with ammonia to pH=9.6
Mobile phase B—91% methanol, 0.1% formic acid, adjusted with ammonia to pH=9.6
Weak Wash—10% methanol
Strong Wash—100% methanol The Sample Manager option "Load Ahead" was used to save time between samples. With this option, each sample was aspirated ready for injection while the previous one was running.

TABLE 9

| | Mobile phase settings | | | |
|---|---|---|---|---|
| Time (min) | Flow Rate (mL/min) | | % A | % B |
| 0-0.8 | 0.7 | | 35.0 | 65.0 |

The samples were automatically injected (injection volume 2.0 or 3.5 μL) and chromatographed by the Acquity UPLC® along with standard reference alkaloids. After the sample set has been run by the Acquity UPLC®, the peaks were identified by comparison with the standards that were run in the sample set. Typical retention times were as follows:

| Alkaloid | Retention time (minutes) |
|---|---|
| Morphine | 0.24 |
| Oripavine | 0.27 |
| Codeine | 0.31 |
| Papaverine | 0.38 |
| Thebaine | 0.42 |
| Noscapine | 0.68 |

The separations obtained using this method are shown in FIG. 1. Although the peak shapes and separations are not perfect, they are quite adequate for a very rapid screening method.

Empower software (Waters Corporation, Milford, Mass.) was used to identify peaks and calculate peak areas. The data was then exported to an Excel spreadsheet where peak area data was used to determine which poppies had unusual alkaloid profiles.

Figure 2:
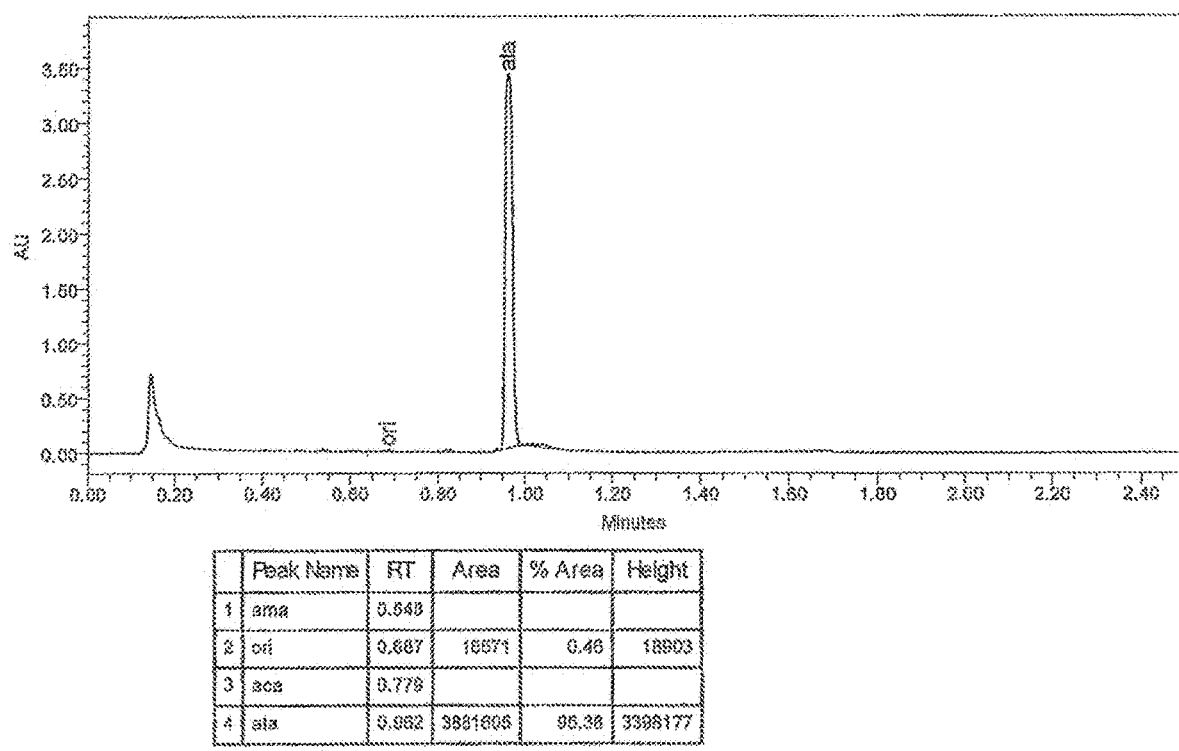
FIG. 2 provides a chromatogram of the poppy straw of the M3 generation of FN1-1242-3. ATA indicates thebaine, ori indicates oripavine peak, AMA represents morphine, and ACA represents codeine.

Gradient Method:

For more accurate repeat analysis of samples, a 2.5 minute gradient UPLC method was used. It is the same as described above, except that the following gradient conditions were used. FIG. 2 provides a chromatogram of the poppy straw of the M3 generation of FN1-1242-3. The injection volume of the sample in FIG. 2 was 2.0 μL. ATA indicates thebaine, ori indicates oripavine peak, AMA represents morphine, and ACA represents codeine.

TABLE 10

Instrument method details for 2.5 min gradient method

| Time (min) | Flow Rate (mL/min) | % A | % B | Curve |
|---|---|---|---|---|
| 0 | 0.8 | 75.0 | 25.0 | |
| 1.4 | 0.8 | 1.0 | 99.0 | 6 |
| 2.5 | 0.8 | 75.0 | 25.0 | 1 |

Example 3

Determination of Genetics of Thebaine-Only Trait

Crosses were conducted between FN1 lines with low content of oripavine (<2% of combination of morphine, codeine, oripavine and thebaine) and normal poppy lines containing morphine. Plants of the first F1 generation all contained morphine, indicating that the genes responsible for the thebaine-only characteristic are recessive. The F1 plants were self pollinated. Seeds were collected from the F1 plants, and sown in trays. When the plants were at the 6-leaf stage, latex testing was conducted to determine the chemotypes of the individual F2 plants.

Latex testing was done according to the method of Example 4 by removing the tip of the youngest fully expanded leaf and placing it in acid extractant buffer in a Pall filter plate. After allowing time for the latex to bleed from the leaf into the buffer, the extractant was vacuum filtered into a 96 well plate and sealed. The samples were analysed by UPLC using the method shown in Example 4.

The alkaloid concentrations were calculated from the peak areas by reference to standard alkaloid solutions, and each alkaloid was converted to a percentage of total morphinan alkaloid (morphine, codeine, thebaine and oripavine) in order to determine the chemotype of the plant. A set of rules incorporated in nested "IF" statements was established to determine chemotype. The rules, applied sequentially, were as follows:

If total concentration of morphine, codeine, thebaine and oripavine is less than 5 ug/mL in injected solution, no result.

If Noscapine percentage >15, chemotype=Noscapine.

If Thebaine percentage >98, chemotype=Thebaine-only.

If Thebaine+Oripavine percentage >95, chemotype=Norman.

If Thebaine+Codeine percentage >96, chemotype=Codeine.

If Morphine percentage >2, chemotype=Morphine.

Otherwise, the chemotype was classified as OCT, which indicates that the plant contained oripavine, codeine and thebaine.

Four chemotypes were identified in the populations:

Morphine: morphine present typically with thebaine and codeine

Norman: thebaine and oripavine both present, substantially no morphine

Thebaine-only: thebaine present, substantially no oripavine and morphine

Codeine: thebaine and codeine present, substantially no morphine

The occasional plant was identified as OCT. These generally were very small plants that fitted into one of the four categories as they further developed. Overall, 0.18% of plants were classified as OCT and 0.03% were classified as noscapine and were ignored in calculation of ratios for this analysis.

Chi square tests were conducted to determine if the observed segregation patterns differed significantly from a 9:3:3:1 segregation of chemotypes (Morphine:codeine:Norman:Thebaine-only respectively).

Table 11 shows the results of the 9 populations derived from FN1 parents having a thebaine-only chemotype. Five of these fit a 9:3:3:1 ratio (P<0.05). Of those that didn't fit the expected ratio, FN1-1242 is notable, in that it had more than the expected number of plants with the codeine chemotype, whilst all other lines that did not fit the ratio had less than expected codeine plants. Further work was conducted with progeny of FN1-1242 in which plants were grown to hook stage, and leaf latex was collected and classified into chemotypes. The distribution was 96:41:42:11, which gives a Chi square test of 3.1 which indicates that there is no significant difference from the expected ratio.

The segregation into 4 chemotypes indicates that two separate genes are involved in the thebaine-only chemotype. One of these is the gene associated with the Norman poppy mutation (described in U.S. Pat. No. 6,067,749). The second gene is responsible for the new low-oripavine or thebaine-only trait, which is responsible for blocking the pathway between thebaine and oripavine. These two genetic changes work together in lines described herein to provide the poppy plants with a high thebaine content and a low oripavine content.

TABLE 11

Segregation patterns for populations using FN1 lines with <2% oripavine in alkaloid profile.

| FN1 line | Alkaloid content in straw of FN1 M2 plant as percentage of sum of morphine, codeine, oripavine and thebaine | | Observed ratio Morphine:codeine:Norman:thebaine-only | Chi square test result (ns indicates no significant difference from 9:3:3:1 ratio) |
|---|---|---|---|---|
| | Oripavine % | Thebaine % | | |
| FN1-846-2 | 0.24 | 98.4 | 39:14:11:4 | 0.39 ns |
| FN1-1719-1 | 0.31 | 99.5 | 45:10:1:0 | 17.9 < 0.001 |
| FN1-2199 | 0.38 | 99.6 | 59:25:18:6 | 1.5 ns |
| FN1-1242 | 0.41 | 99.2 | 271:112:81:16 | 12.81 < 0.01 |
| FN1-900 | 0.58 | 98.8 | 191:73:55:19 | 2.79 ns |
| FN1-2152 | 1.38 | 98.6 | 73:2:28:14 | 26.7 < 0.001 |
| FN1-1571 | 1.63 | 97.9 | 604:58:248:69 | 114.7 < 0.001 |

Example 4

Leaf Latex Analysis

Reagent

Acid Extractant: A 1 L measuring cylinder was half filled with deionised water. 1 mL of conc. phosphoric acid and 50 mL ethanol were added and the volume made up to 1 L with deionised water.

Method

A Pall AcroPrep™ 96 well, 0.2 µm GHP filter plate was placed on a 96 well, 350 µL collection plate. Both filter and collection plate were labeled and 280 µL of acid extractant pipetted into each well of the filter plate using a multipipette. A tip of the youngest fully expanded leaf was torn off each plant to be tested and added to the extractant. The latex bleeds into the solution over time.

The samples were allowed to incubate at room temperature for at least 30 minutes. The samples were filtered using a vacuum manifold (Pall Corporation product No. 5017). The collection plate was covered with ABgene® adhesive PCR sealing foil (Cat #: AB-0626) to prevent evaporation. The collection plate can be stored in the refrigerator or freezer pending analysis.

Analysis Method

The samples were analyzed using the same instrument, reagents and instrument method details (see Table 10) as described for the gradient method in Example 2.

The samples were automatically injected and chromatographed by the Acquity UPLC® along with standard reference alkaloids. After the sample set has been run by the Acquity UPLC®, the peaks were identified by comparison with the standards that were run in the sample set. Empower software (Waters Corporation, Milford, Mass.) was used to identify peaks and calculate peak areas. The data was then exported to an Excel spreadsheet where peak area data was used to determine alkaloid profiles.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A plant comprising a stably reproducing plant of *Papaver somniferum* which upon the harvesting of its poppy capsules will yield a poppy straw having a thebaine fraction constituting about 95% by weight or greater of an alkaloid combination, and an oripavine fraction constituting about 5% by weight or less of the alkaloid combination, wherein the alkaloid combination comprises morphine, codeine, thebaine and oripavine; and wherein thebaine constitutes about 3.0% or greater of the poppy straw on a dry weight basis, the plant being stably reproducing by self pollination in respect of (i) the thebaine and oripavine fractions in the alkaloid combination and (ii) the thebaine content of the poppy straw.

2. The plant of claim 1, wherein the thebaine constitutes at least 3.5% or greater of the poppy straw on a dry weight basis.

3. The plant of claim 1, wherein the thebaine constitutes about 4.0% or greater of the poppy straw on a dry weight basis.

4. The plant of claim 1, wherein thebaine constitutes about 97% by weight or greater of the alkaloid combination and oripavine constitutes about 0.7% by weight or less of the alkaloid combination.

5. The plant of claim 1, wherein there is substantially no morphine and substantially no codeine in the alkaloid combination.

6. The plant of claim 5, wherein there is substantially no oripavine in the alkaloid combination.

7. The plant of claim 1, wherein oripavine constitutes between 0.01 to 1.0% by weight of the alkaloid combination.

8. The plant of claim 1, wherein the high thebaine content is provided by two independent traits, one trait controlling the accumulation of thebaine and oripavine compared with morphine and codeine, and the second trait controlling the accumulation of thebaine compared with oripavine.

9. The plant of claim 1, wherein the high thebaine content is provided by two independent genetic changes, one genetic change controlling the accumulation of thebaine and oripavine compared with morphine and codeine, and the second genetic change controlling the accumulation of thebaine compared with oripavine.

10. A method for producing a mutant poppy plant of *Papaver somniferum* having at least one mutation that produces a stably heritable high thebaine content and low oripavine content, the method comprising the steps of:
   a) exposing at least one poppy seed of *Papaver somniferum* to a mutagenizing agent to produce at least one mutagenized poppy seed, wherein the mutagenizing agent is a chemical agent selected from ethyl methanesulfonate (EMS), diepoxybutane, ethyl-2-chloroethyl sulphide, 2-chloroethyl-dimethylamine, ethylene oxide, ethyleneimine, dimethyl sulphonate, diethyl sulphonate, propane sulphone, beta-propiolactone, diazomethane, N-methyl-N-nitrosourethane, acridine orange, or sodium azide; x-ray irradiation; gamma (γ) ray irradiation; or fast neutron irradiation (FNM),
   b) growing the at least one mutagenized poppy seed to produce a plant bearing a leaf or an immature poppy capsule, optionally through multiple self-fertilized generations,
   c) sampling the leaf or poppy capsule for presence of thebaine, oripavine, morphine and codeine, and
   d) repeating steps b) and c) and optionally step (a) until a poppy plant of *Papaver somniferum* is obtained which yields at least one poppy seed carrying the at least one mutation and a poppy straw having thebaine constituting about 95% by weight or greater of the alkaloid combination consisting of morphine, codeine, thebaine and oripavine, and having oripavine constituting about 5% by weight or less of the alkaloid combination, and wherein thebaine constitutes about 3.0% or greater of the alkaloid content of the poppy straw on a dry weight basis.

11. The method according to claim 10, wherein the *Papaver somniferum* seed exposed to the mutagenizing agent in step (a) is a *Papaver somniferum* yielding, upon the harvesting of its poppy capsules, a poppy straw having a thebaine and oripavine content constituting 50% by weight or greater of the alkaloid combination consisting of morphine, codeine, thebaine and oripavine.

12. The method according to claim 10, wherein step (b) further comprises growing the at least one poppy seed carrying the at least one mutation to produce a plant bearing a leaf or an immature poppy capsule, and self-pollinating to produce seed, and taking the seed thereby produced and producing an M2 generation of plants, and step (c) comprises screening the M2 plants and selecting plants which yield a poppy straw having thebaine constituting about 95% by weight or greater of the alkaloid combination consisting of morphine, codeine, thebaine and oripavine, and having oripavine constituting about 5% by weight or less of the alkaloid combination, and wherein thebaine constitutes about 3.0% or greater of the poppy straw on a dry weight basis.

13. The method according to claim 11, wherein the *Papaver somniferum* seed exposed to the mutagenizing agent in step (a) is seed selected from the group consisting of ATCC PTA-9110 and ATCC PTA-9109.

14. The method according to claim 10, wherein the mutagenizing agent is fast neutron irradiation.

15. A seed, an opium, or a concentrate of poppy straw of the plant of claim 1.

16. A seed, an opium, or a concentrate of poppy straw of the plant of claim 10.

17. An alkaloid combination, wherein thebaine constitutes about 90% by weight or greater of the alkaloid combination, and wherein oripavine constitutes about 10% by weight or less of the alkaloid combination, wherein the alkaloid combination comprises morphine, codeine, thebaine, and oripavine.

18. The alkaloid combination of claim 17, wherein thebaine constitutes about 95% by weight or greater of the alkaloid combination and wherein oripavine constitutes about 5% by weight or less of the alkaloid combination.

19. The alkaloid combination of claim 17, wherein thebaine constitutes about 97% by weight or greater of the alkaloid combination and wherein oripavine constitutes about 3% by weight or less of the alkaloid combination.

20. A poppy straw comprising the alkaloid combination of claim 18, wherein thebaine constitutes about 3.0% or greater of the poppy straw on a dry weight basis.

21. The poppy straw of claim 20, wherein thebaine constitutes about 3.5% or greater of the poppy straw on a dry weight basis.

22. The poppy straw of claim 20, wherein thebaine constitutes about 4% or greater of the poppy straw on a dry weight basis.

23. A seed produced by a poppy plant comprising the alkaloid combination of claim 17.

24. A poppy plant comprising the alkaloid combination of claim 17.

25. An opium comprising the alkaloid combination of claim 17.

26. A concentrate of poppy straw comprising the alkaloid combination of claim 17.

27. Poppy straw of the plant of claim 1.

28. The method of claim 13, wherein the *Papaver somniferum* seed exposed to the mutagenizing agent in step (a) is ATCC PTA-9110.

* * * * *